United States Patent
Taylor et al.

(10) Patent No.: US 12,043,871 B2
(45) Date of Patent: *Jul. 23, 2024

(54) DETECTING NEOPLASM

(71) Applicant: Mayo Foundation for Medical Education and Research, Rochester, MN (US)

(72) Inventors: William R. Taylor, Lake City, MN (US); Jonathan J. Harrington, Madison, WI (US); Patrick S. Quint, Kasson, MN (US); Hongzhi Zou, Middleton, WI (US); Harold R. Bergen, III, Spring Valley, MN (US); David I. Smith, Rochester, MN (US); David A. Ahlquist, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/062,419

(22) Filed: Dec. 6, 2022

(65) Prior Publication Data

US 2023/0272482 A1 Aug. 31, 2023

Related U.S. Application Data

(63) Continuation of application No. 16/738,706, filed on Jan. 9, 2020, now Pat. No. 11,530,449, which is a continuation of application No. 15/724,890, filed on Oct. 4, 2017, now Pat. No. 10,590,489, which is a continuation of application No. 15/467,739, filed on Mar. 23, 2017, now Pat. No. 9,803,249, which is a continuation of application No. 15/197,105, filed on Jun. 29, 2016, now Pat. No. 9,632,093, which is a continuation of application No. 14/827,013, filed on Aug. 14, 2015, now Pat. No. 9,399,800, which is a continuation of application No. 14/168,552, filed on Jan. 30, 2014, now Pat. No. 9,121,070, which is a continuation of application No. 12/866,558, filed as application No. PCT/US2009/033793 on Feb. 11, 2009, now Pat. No. 8,673,555.

(60) Provisional application No. 61/029,221, filed on Feb. 15, 2008.

(51) Int. Cl.
C12Q 1/6886 (2018.01)
C12Q 1/37 (2006.01)
C12Q 1/40 (2006.01)
G01N 33/574 (2006.01)

(52) U.S. Cl.
CPC ............ *C12Q 1/6886* (2013.01); *C12Q 1/37* (2013.01); *C12Q 1/40* (2013.01); *C12Y 302/01001* (2013.01); *C12Y 304/2107* (2013.01); *G01N 33/57407* (2013.01); *G01N 33/57419* (2013.01); *G01N 33/57438* (2013.01); *C12Q 2600/154* (2013.01); *C12Q 2600/156* (2013.01); *C12Q 2600/158* (2013.01); *G01N 2333/928* (2013.01); *G01N 2333/966* (2013.01); *G01N 2560/00* (2013.01)

(58) Field of Classification Search
CPC ..................................................... C12Q 1/6886
USPC ........................................................ 435/6.11
See application file for complete search history.

(56) References Cited

U.S. PATENT DOCUMENTS

| 6,143,529 A | 11/2000 | Lapidus et al. |
|---|---|---|
| 8,673,555 B2 | 3/2014 | Taylor |
| 10,030,272 B2 | 7/2018 | Ahlquist et al. |
| 10,370,726 B2 | 8/2019 | Ahlquist et al. |
| 2007/0054295 A1 | 3/2007 | Spivack |
| 2007/0172823 A1 | 7/2007 | Steinberg |
| 2007/0202513 A1 | 8/2007 | Shuber |
| 2013/0244235 A1 | 9/2013 | Ahlquist et al. |
| 2016/0010081 A1 | 1/2016 | Allawi et al. |
| 2016/0090634 A1 | 3/2016 | Kisiel et al. |
| 2016/0168643 A1 | 6/2016 | Ahlquist |
| 2016/0194721 A1 | 7/2016 | Allawi et al. |
| 2017/0121704 A1 | 5/2017 | Allawi et al. |
| 2017/0321286 A1 | 11/2017 | Allawi et al. |
| 2022/0071605 A1 | 3/2022 | Eisele et al. |
| 2022/0349009 A1 | 11/2022 | Taylor et al. |

FOREIGN PATENT DOCUMENTS

| WO | 2001/042781 | 6/2001 |
|---|---|---|
| WO | 2003/087390 | 10/2003 |
| WO | 2006/094149 | 9/2006 |
| WO | 06/119434 | 11/2006 |
| WO | 2007/134779 | 11/2007 |
| WO | WO 2008/084219 | 7/2008 |
| WO | WO 2010/089538 | 8/2010 |
| WO | WO 2011/119934 | 9/2011 |
| WO | 2011/126768 | 10/2011 |

(Continued)

OTHER PUBLICATIONS

Ahlquist et al., 2000, "Colorectal cancer screening by detection of altered human DNA in stool: feasibility of a multitarget assay panel", Gastroenterology, 119:1219.

Boynton et al., 2003, "DNA integrity as a potential marker for stool-based detection of colorectal cancer", Clin. Chem., 49:1058.

Davies, 2005, "Somatic mutations of the protein kinase gene family in human lung cancer", Cancer Res. 65 (17):7591-5.

Greenman et al., 2007, "Patterns of somatic mutation in human cancer genomes", Nature, 446(7132):153-8.

(Continued)

*Primary Examiner* — Sean E Aeder
(74) *Attorney, Agent, or Firm* — Casimir Jones, S.C.; Peter J. Schlueter

(57) ABSTRACT

This document relates to methods and materials for detecting premalignant and malignant neoplasms. For example, methods and materials for determining whether or not a stool sample from a mammal contains nucleic acid markers or polypeptide markers of a neoplasm are provided.

13 Claims, 12 Drawing Sheets

Specification includes a Sequence Listing.

(56) References Cited

FOREIGN PATENT DOCUMENTS

| WO | WO 2012/106525 | 8/2012 |
|----|----|----|
| WO | 2012/155072 | 11/2012 |
| WO | WO 2013/103889 | 7/2013 |
| WO | WO 2013/142545 | 9/2013 |
| WO | WO 2014/159650 | 10/2014 |
| WO | WO 2014/159652 | 10/2014 |
| WO | WO 2015/066695 | 5/2015 |
| WO | WO 2015/095689 | 6/2015 |
| WO | WO 2015/153283 | 10/2015 |
| WO | WO 2015/153284 | 10/2015 |
| WO | WO 2016/094813 | 6/2016 |
| WO | WO 2016/160454 | 6/2016 |
| WO | WO 2017/040627 | 10/2016 |
| WO | WO 2017/075061 | 3/2017 |
| WO | WO 2017/180886 | 5/2017 |
| WO | WO 2017/192221 | 10/2017 |
| WO | WO 2017/210372 | 12/2017 |
| WO | WO 2018/017740 | 1/2018 |
| WO | WO 2018/045322 | 3/2018 |
| WO | WO 2018/140781 | 8/2018 |
| WO | WO 2018/160576 | 9/2018 |
| WO | WO 2019/108626 | 6/2019 |
| WO | WO 2020/089691 | 5/2020 |
| WO | WO 2020/112869 | 6/2020 |
| WO | WO 2020/118274 | 6/2020 |
| WO | WO 2020/154665 | 7/2020 |
| WO | WO 2020/206256 | 10/2020 |
| WO | WO 2020/236939 | 11/2020 |
| WO | WO 2020/264220 | 12/2020 |
| WO | WO 2021/041726 | 3/2021 |
| WO | WO 2021/076969 | 4/2021 |
| WO | WO 2021/087275 | 5/2021 |
| WO | WO 2021/212031 | 10/2021 |
| WO | WO 2021/226071 | 11/2021 |
| WO | WO 2021/226074 | 11/2021 |
| WO | WO 2022/039904 | 2/2022 |
| WO | WO 2022/040306 | 2/2022 |
| WO | WO 2022/165247 | 8/2022 |
| WO | WO 2022/187227 | 9/2022 |
| WO | WO 2022/187695 | 9/2022 |
| WO | WO 2023/081796 | 5/2023 |

OTHER PUBLICATIONS

Sjoblom et al., 2006, "The consensus coding sequences of human breast and colorectal cancers", Science, 314 (5797):268-74.

Soussi and Lozano, 2005, "p53 mutation heterogeneity in cancer", Biochem. Biophys. Res. Commun. 331 (3):834-42.

Stephens et al., 2005, "A screen of the complete protein kinase gene family identifies diverse patterns of somatic mutations in human breast cancer", Nat. Genet. 37(6):590-2.

Wilm et al., 1996, "Femtomole sequencing of proteins from polyacrylamide gels by nano-electrospray mass spectrometry", Nature, 379:466-469.

Wood et al., 2007, "The genomic landscapes of human breast and colorectal cancers", Science, 318(5853):1108-13.

Zou et al., 2006, "A sensitive method to quantify human long DNA in stool: relevance to colorectal cancer screening", Cancer Epidemiol. Biomarkers Prev, 15(6):1115.

Zou et al., 2007, "Highly methylated genes in colorectal neoplasia: implications for screening", Cancer Epidemiol. Biomarkers Prev, 16(12):2686-2696.

Zou et al., 2008, "High detection rates of colorectal neoplasia by stool DNA testing with a novel digital melt curve assay", Gastroenterology 136(2):459-70.

Cavestro, G., et al., "Role of faecal elastase 1 in pancreatic cancer: A pilot study," Pancreas, Raven press, new York, NY, US, vol. 29, No. 4, Nov. 5, 2004, pp. 349-350.

Shimada, Shimya, et al,."Pancreatic elastase IIIA and its variants are expressed in pancreatic carcinoma cells," International Journal of Molecular Medicine, Spandidos Publications, GR, vol. 10, No. 5, Nov. 1, 2002.

Haug, Ulrike, et al., "Mutant-enriched PCR and allele-specific hybridization reaction to detect K-ras mutations in stool DNA: High prevalence in a large sample of older adults," Clinical Chemistry, vol. 53, No. 4, Apr. 2007.

Naruse, S., et al., "Fecal pancreatic elastase: A reproducible marker for severe exocrine pancreatic insufficiency," Journal of Astroenterolgy 200609 JP LNKD, vol. 41, No. 9, Sep. 2006.

Jiang X, et al., "T1102 Detection of Colorectal Neoplasia by Stool DNA Testing: High Discrimination with Multi-Marker Quantitation," Gastroenterology, Elsevier, Philadelphia, PA, vol. 134, No. 4, Apr. 1, 2008, pp. A-484.

Hanley, Robert, et al., "DNA Integrity Assay: A Plasma-Based Screening Tool for the Detection of Prostate Cancer," Clin. Cancer Res. vol. 12 No. 15 pp. 4569-4574, Aug. 1, 2006.

Koinuma et al. Screening for genomic fragments that are methylated specifically in colorectal carcinoma with a methylated MLH1 promoter (Carcinogenesis, 2005, 26(12): 2078-2085).

Etzioni et al.The Case for Early Detection (Nature Reviews, Apr. 2003, 3: internet pp. 1-10).

Mercer Use of Multiple Markers to Enhance Clinical Utility (Immunol Ser., 1990, 53:39-54).

Wang, et al. Usefulness of p53 gene mutations in the supernatant of bile for diagnosis of biliary tract carcinoma: comparison with K-ras mutation (J. Gastroenterol, 2002, 37:831-839).

Krauzn et al., (British Journal of Cancer, 2005, 93:949-952).

Nelson et al. (Cancert Research, 1999, 59: 4570-4573).

Montiero et al. (J. Clin Microbiol, 1997, 35(4): 995-998).

Dai et al. (Neoplasia, 2001, 3(4): 314-323).

Horikoshi et al. (Leuk Res, 1994, 18(9): Abstract).

Tan et al. "Variable promoter region CpG island methylation of the putative tumor suppressor gene Connexin 26 in breast cancer" Carcinogenesis. 2002 23(2): 231-236.

Jin et al. "A multicenter, Double-blinded Validation study of methylation biomarkers for progression prediction in Barrett's Esophagus" Cancer Research, May 15, 2009, vol. 69, pp. 4112-4115.

Kaz et al. "DNA methylation profiling in Barrett's esophagus and esophageal adenocarcinoma reveals unique methylation signatures and molecular subclasses" Epigenetics, Dec. 1, 2011, vol. 6, pp. 1403-1412.

Zhai et al. "Genome-wide DNA Methylation Profiling of Cell-Free Serum DNA in Esophageal Adenocarcinoma and Barrett Esophagus" Neoplasia, Jan. 11, 2012, vol. 14, No. 1, pp. 29-33.

International Search Report, International Application No. PCT/US2016/023782, mailed Sep. 1, 2016.

Haag S, et al., "Regression of Barrett's esophagus: the role of acid suppression, surgery, and ablative methods." Gastrointest Endosc. Aug. 1999;50(2):229-40.

Supplemental Search Report, EP Patent Application No. 15772326.3, mailed Oct. 6, 2017.

Breivik et al. (Br J Cancer, 1994, 69: 367-371).

Clayton et al. (Clin Chem, 2000, 46(12): 1929-1938).

Machiels et al., BioTechniques, 2000, 28: 286-290.

Deuter et al., Nucleic Acids Research, 1195, 23 (18): 3800-3801.

Belshaw et al., Cancer Epidemiology, Biomarkers & Prevention, 2004, 13(9): 1495-1501.

A. K-ras mutation (5571G>T, 12G>V)

B. APC mutation (102457delC)

SEQUENCE LISTING

```
Sequence total quantity: 222
SEQ ID NO: 1             moltype = DNA  length = 37
FEATURE                  Location/Qualifiers
source                   1..37
                         mol_type = other DNA
                         organism = synthetic construct
SEQUENCE: 1
gtggacgaat atgatccaac aatagaggta aatcttg                              37

SEQ ID NO: 2             moltype = DNA  length = 20
FEATURE                  Location/Qualifiers
source                   1..20
                         mol_type = other DNA
                         organism = synthetic construct
SEQUENCE: 2
aggcctgctg aaaatgactg                                                 20

SEQ ID NO: 3             moltype = DNA  length = 22
FEATURE                  Location/Qualifiers
source                   1..22
                         mol_type = other DNA
                         organism = synthetic construct
SEQUENCE: 3
ttgttggatc atattcgtcc ac                                              22

SEQ ID NO: 4             moltype = DNA  length = 20
FEATURE                  Location/Qualifiers
source                   1..20
                         mol_type = other DNA
                         organism = synthetic construct
SEQUENCE: 4
taaggcctgc tgaaaatgac                                                 20

SEQ ID NO: 5             moltype = DNA  length = 20
FEATURE                  Location/Qualifiers
source                   1..20
                         mol_type = other DNA
                         organism = synthetic construct
SEQUENCE: 5
atcaaagaat ggtcctgcac                                                 20

SEQ ID NO: 6             moltype = DNA  length = 22
FEATURE                  Location/Qualifiers
source                   1..22
                         mol_type = other DNA
                         organism = synthetic construct
SEQUENCE: 6
cgtctgcagt caactggaat tt                                              22

SEQ ID NO: 7             moltype = DNA  length = 22
FEATURE                  Location/Qualifiers
source                   1..22
                         mol_type = other DNA
                         organism = synthetic construct
SEQUENCE: 7
tgtatcgtca aggcactctt gc                                              22

SEQ ID NO: 8             moltype = DNA  length = 20
FEATURE                  Location/Qualifiers
source                   1..20
                         mol_type = other DNA
                         organism = synthetic construct
SEQUENCE: 8
cttaagcgtc gatggaggag                                                 20

SEQ ID NO: 9             moltype = DNA  length = 37
FEATURE                  Location/Qualifiers
source                   1..37
                         mol_type = other DNA
                         organism = synthetic construct
SEQUENCE: 9
ccagacaact gttcaaactg atgggaccca ctccatc                              37

SEQ ID NO: 10            moltype = DNA  length = 20
FEATURE                  Location/Qualifiers
source                   1..20
                         mol_type = other DNA
                         organism = synthetic construct
```

```
SEQUENCE: 10
ccacaaaatg gatccagaca                                              20

SEQ ID NO: 11          moltype = DNA   length = 22
FEATURE                Location/Qualifiers
source                 1..22
                       mol_type = other DNA
                       organism = synthetic construct
SEQUENCE: 11
tgcttgctct gataggaaaa tg                                           22

SEQ ID NO: 12          moltype = DNA   length = 37
FEATURE                Location/Qualifiers
source                 1..37
                       mol_type = other DNA
                       organism = synthetic construct
SEQUENCE: 12
cagatagccc tggacaaacc atgccaccaa gcagaag                           37

SEQ ID NO: 13          moltype = DNA   length = 37
FEATURE                Location/Qualifiers
source                 1..37
                       mol_type = other DNA
                       organism = synthetic construct
SEQUENCE: 13
ttccagcagt gtcacagcac cctagaacca aatccag                           37

SEQ ID NO: 14          moltype = DNA   length = 39
FEATURE                Location/Qualifiers
source                 1..39
                       mol_type = other DNA
                       organism = synthetic construct
SEQUENCE: 14
atgcaaatgg gaatgaaaca gaatcagagc agcctaaag                         39

SEQ ID NO: 15          moltype = DNA   length = 24
FEATURE                Location/Qualifiers
source                 1..24
                       mol_type = other DNA
                       organism = synthetic construct
SEQUENCE: 15
ttcattatca tctttgtcat cagc                                         24

SEQ ID NO: 16          moltype = DNA   length = 20
FEATURE                Location/Qualifiers
source                 1..20
                       mol_type = other DNA
                       organism = synthetic construct
SEQUENCE: 16
cgctcctgaa gaaaattcaa                                              20

SEQ ID NO: 17          moltype = DNA   length = 23
FEATURE                Location/Qualifiers
source                 1..23
                       mol_type = other DNA
                       organism = synthetic construct
SEQUENCE: 17
tgcagggttc tagtttatct tca                                          23

SEQ ID NO: 18          moltype = DNA   length = 20
FEATURE                Location/Qualifiers
source                 1..20
                       mol_type = other DNA
                       organism = synthetic construct
SEQUENCE: 18
ctggcaatcg aacgactctc                                              20

SEQ ID NO: 19          moltype = DNA   length = 20
FEATURE                Location/Qualifiers
source                 1..20
                       mol_type = other DNA
                       organism = synthetic construct
SEQUENCE: 19
caggagaccc cactcatgtt                                              20

SEQ ID NO: 20          moltype = DNA   length = 25
FEATURE                Location/Qualifiers
source                 1..25
                       mol_type = other DNA
```

```
                       organism = synthetic construct
SEQUENCE: 20
tggcaaaatg taataaagta tcagc                                          25

SEQ ID NO: 21          moltype = DNA   length = 20
FEATURE                Location/Qualifiers
source                 1..20
                       mol_type = other DNA
                       organism = synthetic construct
SEQUENCE: 21
catgccacca agcagaagta                                                20

SEQ ID NO: 22          moltype = DNA   length = 20
FEATURE                Location/Qualifiers
source                 1..20
                       mol_type = other DNA
                       organism = synthetic construct
SEQUENCE: 22
cactcaggct ggatgaacaa                                                20

SEQ ID NO: 23          moltype = DNA   length = 20
FEATURE                Location/Qualifiers
source                 1..20
                       mol_type = other DNA
                       organism = synthetic construct
SEQUENCE: 23
gagcctcgat gagccattta                                                20

SEQ ID NO: 24          moltype = DNA   length = 26
FEATURE                Location/Qualifiers
source                 1..26
                       mol_type = other DNA
                       organism = synthetic construct
SEQUENCE: 24
tcaatatcat catcatctga atcatc                                         26

SEQ ID NO: 25          moltype = DNA   length = 20
FEATURE                Location/Qualifiers
source                 1..20
                       mol_type = other DNA
                       organism = synthetic construct
SEQUENCE: 25
gtgaaccatg cagtggaatg                                                20

SEQ ID NO: 26          moltype = DNA   length = 20
FEATURE                Location/Qualifiers
source                 1..20
                       mol_type = other DNA
                       organism = synthetic construct
SEQUENCE: 26
acttctcgct tggtttgagc                                                20

SEQ ID NO: 27          moltype = DNA   length = 20
FEATURE                Location/Qualifiers
source                 1..20
                       mol_type = other DNA
                       organism = synthetic construct
SEQUENCE: 27
catggtttgt ccagggctat                                                20

SEQ ID NO: 28          moltype = DNA   length = 20
FEATURE                Location/Qualifiers
source                 1..20
                       mol_type = other DNA
                       organism = synthetic construct
SEQUENCE: 28
agcatctgga agaacctgga                                                20

SEQ ID NO: 29          moltype = DNA   length = 37
FEATURE                Location/Qualifiers
source                 1..37
                       mol_type = other DNA
                       organism = synthetic construct
SEQUENCE: 29
aagacccagg tccagatgaa gctcccagaa tgccaga                             37

SEQ ID NO: 30          moltype = DNA   length = 20
FEATURE                Location/Qualifiers
source                 1..20
```

```
SEQUENCE: 30
cccttcccag aaaacctacc                                              20

SEQ ID NO: 31         moltype = DNA  length = 20
FEATURE               Location/Qualifiers
source                1..20
                      mol_type = other DNA
                      organism = synthetic construct
SEQUENCE: 31
gccaggcatt gaagtctcat                                              20

SEQ ID NO: 32         moltype = DNA  length = 37
FEATURE               Location/Qualifiers
source                1..37
                      mol_type = other DNA
                      organism = synthetic construct
SEQUENCE: 32
catggccatc tacaagcagt cacagcacat gacggag                           37

SEQ ID NO: 33         moltype = DNA  length = 20
FEATURE               Location/Qualifiers
source                1..20
                      mol_type = other DNA
                      organism = synthetic construct
SEQUENCE: 33
cacttgtgcc ctgactttca                                              20

SEQ ID NO: 34         moltype = DNA  length = 19
FEATURE               Location/Qualifiers
source                1..19
                      mol_type = other DNA
                      organism = synthetic construct
SEQUENCE: 34
aaccagccct gtcgtctct                                               19

SEQ ID NO: 35         moltype = DNA  length = 37
FEATURE               Location/Qualifiers
source                1..37
                      mol_type = other DNA
                      organism = synthetic construct
SEQUENCE: 35
agtggaagga aatttgcgtg tggagtattt ggatgac                           37

SEQ ID NO: 36         moltype = DNA  length = 20
FEATURE               Location/Qualifiers
source                1..20
                      mol_type = other DNA
                      organism = synthetic construct
SEQUENCE: 36
caggcctctg attcctcact                                              20

SEQ ID NO: 37         moltype = DNA  length = 20
FEATURE               Location/Qualifiers
source                1..20
                      mol_type = other DNA
                      organism = synthetic construct
SEQUENCE: 37
cttaacccct cctcccagag                                              20

SEQ ID NO: 38         moltype = DNA  length = 37
FEATURE               Location/Qualifiers
source                1..37
                      mol_type = other DNA
                      organism = synthetic construct
SEQUENCE: 38
atgtgtaaca gttcctgcat gggcggcatg aaccgga                           37

SEQ ID NO: 39         moltype = DNA  length = 20
FEATURE               Location/Qualifiers
source                1..20
                      mol_type = other DNA
                      organism = synthetic construct
SEQUENCE: 39
cttgggcctg tgttatctcc                                              20

SEQ ID NO: 40         moltype = DNA  length = 18
FEATURE               Location/Qualifiers
```

```
source                  1..18
                        mol_type = other DNA
                        organism = synthetic construct
SEQUENCE: 40
gggtcagagg caagcaga                                                         18

SEQ ID NO: 41           moltype = DNA   length = 37
FEATURE                 Location/Qualifiers
source                  1..37
                        mol_type = other DNA
                        organism = synthetic construct
SEQUENCE: 41
cgcacagagg aagagaatct ccgcaagaaa ggggagc                                    37

SEQ ID NO: 42           moltype = DNA   length = 20
FEATURE                 Location/Qualifiers
source                  1..20
                        mol_type = other DNA
                        organism = synthetic construct
SEQUENCE: 42
gggagtagat ggagcctggt                                                       20

SEQ ID NO: 43           moltype = DNA   length = 20
FEATURE                 Location/Qualifiers
source                  1..20
                        mol_type = other DNA
                        organism = synthetic construct
SEQUENCE: 43
gcttcttgtc ctgcttgctt                                                       20

SEQ ID NO: 44           moltype = DNA   length = 21
FEATURE                 Location/Qualifiers
source                  1..21
                        mol_type = other DNA
                        organism = synthetic construct
SEQUENCE: 44
acgcctgtaa tcccagcact t                                                     21

SEQ ID NO: 45           moltype = DNA   length = 19
FEATURE                 Location/Qualifiers
source                  1..19
                        mol_type = other DNA
                        organism = synthetic construct
SEQUENCE: 45
tcgcccaggc tggagtgca                                                        19

SEQ ID NO: 46           moltype = DNA   length = 20
FEATURE                 Location/Qualifiers
source                  1..20
                        mol_type = other DNA
                        organism = synthetic construct
SEQUENCE: 46
tggtgaaacc ccgtctctac                                                       20

SEQ ID NO: 47           moltype = DNA   length = 20
FEATURE                 Location/Qualifiers
source                  1..20
                        mol_type = other DNA
                        organism = synthetic construct
SEQUENCE: 47
ctcactgcaa cctccacctc                                                       20

SEQ ID NO: 48           moltype = DNA   length = 20
FEATURE                 Location/Qualifiers
source                  1..20
                        mol_type = other DNA
                        organism = synthetic construct
SEQUENCE: 48
cgcccggcta atttttgtat                                                       20

SEQ ID NO: 49           moltype = DNA   length = 41
FEATURE                 Location/Qualifiers
source                  1..41
                        mol_type = other DNA
                        organism = synthetic construct
SEQUENCE: 49
atggccatct acaagcagtc atagcacatg acggaggttg t                               41

SEQ ID NO: 50           moltype = DNA   length = 39
```

```
FEATURE              Location/Qualifiers
source               1..39
                     mol_type = other DNA
                     organism = synthetic construct
SEQUENCE: 50
agagtgaacc atgcagtgga aaagtggcat tataagccc                             39

SEQ ID NO: 51        moltype = DNA   length = 37
FEATURE              Location/Qualifiers
source               1..37
                     mol_type = other DNA
                     organism = synthetic construct
SEQUENCE: 51
tttgccaact ggccaagacc taccctgtgc agctgtg                               37

SEQ ID NO: 52        moltype = DNA   length = 40
FEATURE              Location/Qualifiers
source               1..40
                     mol_type = other DNA
                     organism = synthetic construct
SEQUENCE: 52
cagatgctga tactttatta cttttgccac ggaaagtact                            40

SEQ ID NO: 53        moltype = DNA   length = 38
FEATURE              Location/Qualifiers
source               1..38
                     mol_type = other DNA
                     organism = synthetic construct
SEQUENCE: 53
aaagcaccta ctgctgaaag agagtggacc taagcaag                              38

SEQ ID NO: 54        moltype = DNA   length = 38
FEATURE              Location/Qualifiers
source               1..38
                     mol_type = other DNA
                     organism = synthetic construct
SEQUENCE: 54
atgctgcagt tcagaggggt ccaggttctt ccagatgc                              38

SEQ ID NO: 55        moltype = DNA   length = 42
FEATURE              Location/Qualifiers
source               1..42
                     mol_type = other DNA
                     organism = synthetic construct
SEQUENCE: 55
taaagcacct actgctgaaa agagagagtg gacctaagca ag                         42

SEQ ID NO: 56        moltype = DNA   length = 37
FEATURE              Location/Qualifiers
source               1..37
                     mol_type = other DNA
                     organism = synthetic construct
SEQUENCE: 56
cacaggaagc agattctgca ataccctgca aatagca                               37

SEQ ID NO: 57        moltype = DNA   length = 39
FEATURE              Location/Qualifiers
source               1..39
                     mol_type = other DNA
                     organism = synthetic construct
SEQUENCE: 57
ttcagagtga accatgcagg gaatggtaag tggcattat                             39

SEQ ID NO: 58        moltype = DNA   length = 33
FEATURE              Location/Qualifiers
source               1..33
                     mol_type = other DNA
                     organism = synthetic construct
SEQUENCE: 58
tccagatagc cctggataaa ccatgccacc aag                                   33

SEQ ID NO: 59        moltype = DNA   length = 41
FEATURE              Location/Qualifiers
source               1..41
                     mol_type = other DNA
                     organism = synthetic construct
SEQUENCE: 59
ctcaaacagc tcaaaccaag tgagaagtac ctaaaaataa a                          41
```

-continued

```
SEQ ID NO: 60          moltype = DNA   length = 38
FEATURE                Location/Qualifiers
source                 1..38
                       mol_type = other DNA
                       organism = synthetic construct
SEQUENCE: 60
agcagaaata aaagaaaagt tggaactagg tcagctga                              38

SEQ ID NO: 61          moltype = DNA   length = 34
FEATURE                Location/Qualifiers
source                 1..34
                       mol_type = other DNA
                       organism = synthetic construct
SEQUENCE: 61
ctcaaacagc tcaaccagc gagaagtacc taaa                                   34

SEQ ID NO: 62          moltype = DNA   length = 35
FEATURE                Location/Qualifiers
source                 1..35
                       mol_type = other DNA
                       organism = synthetic construct
SEQUENCE: 62
tctggcccct cctcagcgtc ttatccgagt ggaag                                 35

SEQ ID NO: 63          moltype = DNA   length = 35
FEATURE                Location/Qualifiers
source                 1..35
                       mol_type = other DNA
                       organism = synthetic construct
SEQUENCE: 63
cctatgagcc gcctgagatc tggtttgcaa ctggg                                 35

SEQ ID NO: 64          moltype = DNA   length = 35
FEATURE                Location/Qualifiers
source                 1..35
                       mol_type = other DNA
                       organism = synthetic construct
SEQUENCE: 64
atgacagaaa cacttttga catagtgtgg tggtg                                  35

SEQ ID NO: 65          moltype = DNA   length = 35
FEATURE                Location/Qualifiers
source                 1..35
                       mol_type = other DNA
                       organism = synthetic construct
SEQUENCE: 65
gaaacactt tcgacatggt gtggtggtgc cctat                                  35

SEQ ID NO: 66          moltype = DNA   length = 35
FEATURE                Location/Qualifiers
source                 1..35
                       mol_type = other DNA
                       organism = synthetic construct
SEQUENCE: 66
ctgccctcaa caagatgctt tgccaactgg ccaag                                 35

SEQ ID NO: 67          moltype = DNA   length = 35
FEATURE                Location/Qualifiers
source                 1..35
                       mol_type = other DNA
                       organism = synthetic construct
SEQUENCE: 67
aagtctgtga cttgcacagt cagttgccct gaggg                                 35

SEQ ID NO: 68          moltype = DNA   length = 35
FEATURE                Location/Qualifiers
source                 1..35
                       mol_type = other DNA
                       organism = synthetic construct
SEQUENCE: 68
gcatgggcgg catgaactgg aggcccatcc tcacc                                 35

SEQ ID NO: 69          moltype = DNA   length = 35
FEATURE                Location/Qualifiers
source                 1..35
                       mol_type = other DNA
                       organism = synthetic construct
SEQUENCE: 69
tcttttcacc catctaccgt cccccttgcc gtccc                                 35
```

```
SEQ ID NO: 70          moltype = DNA   length = 35
FEATURE                Location/Qualifiers
source                 1..35
                       mol_type = other DNA
                       organism = synthetic construct
SEQUENCE: 70
ccatcatcac actggaatac tccaggtcag gagcc                              35

SEQ ID NO: 71          moltype = DNA   length = 23
FEATURE                Location/Qualifiers
source                 1..23
                       mol_type = other DNA
                       organism = synthetic construct
SEQUENCE: 71
accccgccc gtcacccgcg tcc                                            23

SEQ ID NO: 72          moltype = DNA   length = 35
FEATURE                Location/Qualifiers
source                 1..35
                       mol_type = other DNA
                       organism = synthetic construct
SEQUENCE: 72
ggaacagctt tgaggtgtgt gtttgtgcct gtcct                              35

SEQ ID NO: 73          moltype = DNA   length = 39
FEATURE                Location/Qualifiers
source                 1..39
                       mol_type = other DNA
                       organism = synthetic construct
SEQUENCE: 73
tcagagcagc ctaaagaatg aaatgaaaac caagagaaa                          39

SEQ ID NO: 74          moltype = DNA   length = 35
FEATURE                Location/Qualifiers
source                 1..35
                       mol_type = other DNA
                       organism = synthetic construct
SEQUENCE: 74
cctcaacaag atgtttttcc aactggccaa gacct                              35

SEQ ID NO: 75          moltype = DNA   length = 25
FEATURE                Location/Qualifiers
source                 1..25
                       mol_type = other DNA
                       organism = synthetic construct
SEQUENCE: 75
cctgtcctgg gatagaccgg cgcac                                         25

SEQ ID NO: 76          moltype = DNA   length = 27
FEATURE                Location/Qualifiers
source                 1..27
                       mol_type = other DNA
                       organism = synthetic construct
SEQUENCE: 76
ggagcctcac cactagctgc ccccagg                                       27

SEQ ID NO: 77          moltype = DNA   length = 31
FEATURE                Location/Qualifiers
source                 1..31
                       mol_type = other DNA
                       organism = synthetic construct
SEQUENCE: 77
gtgtttgtgc ctgtcgtggg agagaccggc g                                  31

SEQ ID NO: 78          moltype = DNA   length = 33
FEATURE                Location/Qualifiers
source                 1..33
                       mol_type = other DNA
                       organism = synthetic construct
SEQUENCE: 78
ggaagagaat ctccgctaga aaggggagcc tca                                33

SEQ ID NO: 79          moltype = DNA   length = 41
FEATURE                Location/Qualifiers
source                 1..41
                       mol_type = other DNA
                       organism = synthetic construct
SEQUENCE: 79
```

```
gttaaatatt gtcagtatgc atttgactta aatgtgata g                          41

SEQ ID NO: 80          moltype = DNA  length = 37
FEATURE                Location/Qualifiers
source                 1..37
                       mol_type = other DNA
                       organism = synthetic construct
SEQUENCE: 80
tagtggtaat ctactggaac ggaacagctt tgaggtg                              37

SEQ ID NO: 81          moltype = DNA  length = 33
FEATURE                Location/Qualifiers
source                 1..33
                       mol_type = other DNA
                       organism = synthetic construct
SEQUENCE: 81
cctcctcagc atcttacccg agtggaagga aat                                  33

SEQ ID NO: 82          moltype = DNA  length = 31
FEATURE                Location/Qualifiers
source                 1..31
                       mol_type = other DNA
                       organism = synthetic construct
SEQUENCE: 82
agttcctgca tgggcagcat gaaccggagg c                                    31

SEQ ID NO: 83          moltype = DNA  length = 36
FEATURE                Location/Qualifiers
source                 1..36
                       mol_type = other DNA
                       organism = synthetic construct
SEQUENCE: 83
ctgggcttct tgcattctgg acagccaagt ctgtga                               36

SEQ ID NO: 84          moltype = DNA  length = 21
FEATURE                Location/Qualifiers
source                 1..21
                       mol_type = other DNA
                       organism = synthetic construct
SEQUENCE: 84
tgcccccacc gtgagcgctg c                                               21

SEQ ID NO: 85          moltype = DNA  length = 39
FEATURE                Location/Qualifiers
source                 1..39
                       mol_type = other DNA
                       organism = synthetic construct
SEQUENCE: 85
tcagcatctt atccgagtgt aaggaaattt gcgtgtgga                            39

SEQ ID NO: 86          moltype = DNA  length = 41
FEATURE                Location/Qualifiers
source                 1..41
                       mol_type = other DNA
                       organism = synthetic construct
SEQUENCE: 86
tgcaaatagc agaaataaaa taaaagattg gaactaggtc a                         41

SEQ ID NO: 87          moltype = DNA  length = 39
FEATURE                Location/Qualifiers
source                 1..39
                       mol_type = other DNA
                       organism = synthetic construct
SEQUENCE: 87
ctaaagaatc aaatgaaaaa ccaagagaaa gaggcagaa                            39

SEQ ID NO: 88          moltype = DNA  length = 33
FEATURE                Location/Qualifiers
source                 1..33
                       mol_type = other DNA
                       organism = synthetic construct
SEQUENCE: 88
gtggtagttg gagctgatgg cgtaggcaag agt                                  33

SEQ ID NO: 89          moltype = DNA  length = 35
FEATURE                Location/Qualifiers
source                 1..35
                       mol_type = other DNA
                       organism = synthetic construct
```

```
SEQUENCE: 89
cctcaacaag atgttttacc aactggccaa gacct                                   35

SEQ ID NO: 90          moltype = DNA   length = 37
FEATURE                Location/Qualifiers
source                 1..37
                       mol_type = other DNA
                       organism = synthetic construct
SEQUENCE: 90
cctcctcagc atcttatctg agtggaagga aatttgc                                 37

SEQ ID NO: 91          moltype = DNA   length = 37
FEATURE                Location/Qualifiers
source                 1..37
                       mol_type = other DNA
                       organism = synthetic construct
SEQUENCE: 91
tccactacaa ctacatgtat aacagttcct gcatggg                                 37

SEQ ID NO: 92          moltype = DNA   length = 33
FEATURE                Location/Qualifiers
source                 1..33
                       mol_type = other DNA
                       organism = synthetic construct
SEQUENCE: 92
cactggaaga ctccagatca ggagccactt gcc                                     33

SEQ ID NO: 93          moltype = DNA   length = 25
FEATURE                Location/Qualifiers
source                 1..25
                       mol_type = other DNA
                       organism = synthetic construct
SEQUENCE: 93
ggagaggggg agtgcaggca gcggg                                              25

SEQ ID NO: 94          moltype = DNA   length = 25
FEATURE                Location/Qualifiers
source                 1..25
                       mol_type = other DNA
                       organism = synthetic construct
SEQUENCE: 94
cccaactgcg cctaccccgc cactc                                              25

SEQ ID NO: 95          moltype = DNA   length = 26
FEATURE                Location/Qualifiers
source                 1..26
                       mol_type = other DNA
                       organism = synthetic construct
SEQUENCE: 95
gcccgggagg gctcctggac acgctg                                             26

SEQ ID NO: 96          moltype = DNA   length = 29
FEATURE                Location/Qualifiers
source                 1..29
                       mol_type = other DNA
                       organism = synthetic construct
SEQUENCE: 96
gcccgggagg gcttactgga cacgctggt                                          29

SEQ ID NO: 97          moltype = DNA   length = 44
FEATURE                Location/Qualifiers
source                 1..44
                       mol_type = other DNA
                       organism = synthetic construct
SEQUENCE: 97
caatgggtca tatcacagat tcttttttttt aaattaaagt aaca                        44

SEQ ID NO: 98          moltype = DNA   length = 40
FEATURE                Location/Qualifiers
source                 1..40
                       mol_type = other DNA
                       organism = synthetic construct
SEQUENCE: 98
tcttatctca aagaacaac aaaaaagagg aatcctttag                               40

SEQ ID NO: 99          moltype = DNA   length = 25
FEATURE                Location/Qualifiers
source                 1..25
                       mol_type = other DNA
```

-continued

```
                        organism = synthetic construct
SEQUENCE: 99
gcgcccagcc ctgcgcccat tcctc                                           25

SEQ ID NO: 100          moltype = DNA   length = 39
FEATURE                 Location/Qualifiers
source                  1..39
                        mol_type = other DNA
                        organism = synthetic construct
SEQUENCE: 100
aagtaagtcc agctggcaaa gtgactcagc ctttgactt                            39

SEQ ID NO: 101          moltype = DNA   length = 39
FEATURE                 Location/Qualifiers
source                  1..39
                        mol_type = other DNA
                        organism = synthetic construct
SEQUENCE: 101
aggatgacac ccgggacaat gtttattact atgatgaag                            39

SEQ ID NO: 102          moltype = DNA   length = 36
FEATURE                 Location/Qualifiers
source                  1..36
                        mol_type = other DNA
                        organism = synthetic construct
SEQUENCE: 102
tttttctcc aaaggactga cgctcggcct gaagtg                                36

SEQ ID NO: 103          moltype = DNA   length = 34
FEATURE                 Location/Qualifiers
source                  1..34
                        mol_type = other DNA
                        organism = synthetic construct
SEQUENCE: 103
caagcagaat tgctcacttt cccaactcct ctcc                                 34

SEQ ID NO: 104          moltype = DNA   length = 33
FEATURE                 Location/Qualifiers
source                  1..33
                        mol_type = other DNA
                        organism = synthetic construct
SEQUENCE: 104
ggtcacagcc acagacacgg acgatgatgt gaa                                  33

SEQ ID NO: 105          moltype = DNA   length = 24
FEATURE                 Location/Qualifiers
source                  1..24
                        mol_type = other DNA
                        organism = synthetic construct
SEQUENCE: 105
agccctgcgc ccttcctct cccg                                             24

SEQ ID NO: 106          moltype = DNA   length = 33
FEATURE                 Location/Qualifiers
source                  1..33
                        mol_type = other DNA
                        organism = synthetic construct
SEQUENCE: 106
ttcctcttcc tacagtgctc ccctgccctc aac                                  33

SEQ ID NO: 107          moltype = DNA   length = 33
FEATURE                 Location/Qualifiers
source                  1..33
                        mol_type = other DNA
                        organism = synthetic construct
SEQUENCE: 107
tgctcagata gcgatgatga gcagctgggg ctg                                  33

SEQ ID NO: 108          moltype = DNA   length = 27
FEATURE                 Location/Qualifiers
source                  1..27
                        mol_type = other DNA
                        organism = synthetic construct
SEQUENCE: 108
ggtcggaggc cgagccaggt gggtaga                                         27

SEQ ID NO: 109          moltype = DNA   length = 39
FEATURE                 Location/Qualifiers
source                  1..39
```

```
                        mol_type = other DNA
                        organism = synthetic construct
SEQUENCE: 109
gcttctcttt tcctatccta agtagtggta atctactgg                              39

SEQ ID NO: 110          moltype = DNA  length = 27
FEATURE                 Location/Qualifiers
source                  1..27
                        mol_type = other DNA
                        organism = synthetic construct
SEQUENCE: 110
ttgtgcctgt cctcggagag accggcg                                           27

SEQ ID NO: 111          moltype = DNA  length = 27
FEATURE                 Location/Qualifiers
source                  1..27
                        mol_type = other DNA
                        organism = synthetic construct
SEQUENCE: 111
tgtgcctgtc ctgagagaga ccggcgc                                           27

SEQ ID NO: 112          moltype = DNA  length = 33
FEATURE                 Location/Qualifiers
source                  1..33
                        mol_type = other DNA
                        organism = synthetic construct
SEQUENCE: 112
ttcctcttcc tacagtcctc ccctgccctc aac                                    33

SEQ ID NO: 113          moltype = DNA  length = 37
FEATURE                 Location/Qualifiers
source                  1..37
                        mol_type = other DNA
                        organism = synthetic construct
SEQUENCE: 113
tctacaagca gtcacagctc atgacggagg ttgtgga                                37

SEQ ID NO: 114          moltype = DNA  length = 40
FEATURE                 Location/Qualifiers
source                  1..40
                        mol_type = other DNA
                        organism = synthetic construct
SEQUENCE: 114
aaatgaaaac caagagaaag gcagaaaaaa ctattgattc                             40

SEQ ID NO: 115          moltype = DNA  length = 33
FEATURE                 Location/Qualifiers
source                  1..33
                        mol_type = other DNA
                        organism = synthetic construct
SEQUENCE: 115
cctgccctca acaagacgtt ttgccaactg gcc                                    33

SEQ ID NO: 116          moltype = DNA  length = 41
FEATURE                 Location/Qualifiers
source                  1..41
                        mol_type = other DNA
                        organism = synthetic construct
SEQUENCE: 116
gctcatctct aagctcagga agagttgtgt caaaaatgag a                           41

SEQ ID NO: 117          moltype = DNA  length = 39
FEATURE                 Location/Qualifiers
source                  1..39
                        mol_type = other DNA
                        organism = synthetic construct
SEQUENCE: 117
cggaacagct ttgaggtgca tgtttgtgcc tgtcctggg                              39

SEQ ID NO: 118          moltype = DNA  length = 37
FEATURE                 Location/Qualifiers
source                  1..37
                        mol_type = other DNA
                        organism = synthetic construct
SEQUENCE: 118
tggaaggaaa tttgcgtgtg gagtatttgg atgacag                                37

SEQ ID NO: 119          moltype = DNA  length = 36
FEATURE                 Location/Qualifiers
```

```
source                  1..36
                        mol_type = other DNA
                        organism = synthetic construct
SEQUENCE: 119
tgtcctggga gagactggcg cacagaggaa gagaat                          36

SEQ ID NO: 120          moltype = DNA  length = 38
FEATURE                 Location/Qualifiers
source                  1..38
                        mol_type = other DNA
                        organism = synthetic construct
SEQUENCE: 120
aagaaaagat tggaactaga tcagctgaag atcctgtg                        38

SEQ ID NO: 121          moltype = DNA  length = 30
FEATURE                 Location/Qualifiers
source                  1..30
                        mol_type = other DNA
                        organism = synthetic construct
SEQUENCE: 121
cgcccggcac ccgcttccgc gccatggcca                                 30

SEQ ID NO: 122          moltype = DNA  length = 31
FEATURE                 Location/Qualifiers
source                  1..31
                        mol_type = other DNA
                        organism = synthetic construct
SEQUENCE: 122
gtgtttgtgc ctgtgctggg agagaccggc g                               31

SEQ ID NO: 123          moltype = DNA  length = 37
FEATURE                 Location/Qualifiers
source                  1..37
                        mol_type = other DNA
                        organism = synthetic construct
SEQUENCE: 123
aggttcttcc agatgctgat actttattac attttgc                         37

SEQ ID NO: 124          moltype = DNA  length = 37
FEATURE                 Location/Qualifiers
source                  1..37
                        mol_type = other DNA
                        organism = synthetic construct
SEQUENCE: 124
gcgagaagta cctaaaaata aagcacctac tgctgaa                         37

SEQ ID NO: 125          moltype = DNA  length = 37
FEATURE                 Location/Qualifiers
source                  1..37
                        mol_type = other DNA
                        organism = synthetic construct
SEQUENCE: 125
cagggttcta gtttatctta agaatcagcc aggcaca                         37

SEQ ID NO: 126          moltype = DNA  length = 38
FEATURE                 Location/Qualifiers
source                  1..38
                        mol_type = other DNA
                        organism = synthetic construct
SEQUENCE: 126
ccagatgctg atactttatt ttgccacgga aagtactc                        38

SEQ ID NO: 127          moltype = DNA  length = 38
FEATURE                 Location/Qualifiers
source                  1..38
                        mol_type = other DNA
                        organism = synthetic construct
SEQUENCE: 127
aaagcaccta ctgctgaaag agagtggacc taagcaag                        38

SEQ ID NO: 128          moltype = DNA  length = 20
FEATURE                 Location/Qualifiers
source                  1..20
                        mol_type = other DNA
                        organism = synthetic construct
SEQUENCE: 128
agtactcccc tgccctcaac                                            20

SEQ ID NO: 129          moltype = DNA  length = 20
```

```
FEATURE             Location/Qualifiers
source              1..20
                    mol_type = other DNA
                    organism = synthetic construct
SEQUENCE: 129
tttgagagtc gttcgattgc                                              20

SEQ ID NO: 130      moltype = DNA  length = 20
FEATURE             Location/Qualifiers
source              1..20
                    mol_type = other DNA
                    organism = synthetic construct
SEQUENCE: 130
tccaggttct tccagatgct                                              20

SEQ ID NO: 131      moltype = DNA  length = 20
FEATURE             Location/Qualifiers
source              1..20
                    mol_type = other DNA
                    organism = synthetic construct
SEQUENCE: 131
agctcaaacc aagcgagaag                                              20

SEQ ID NO: 132      moltype = DNA  length = 21
FEATURE             Location/Qualifiers
source              1..21
                    mol_type = other DNA
                    organism = synthetic construct
SEQUENCE: 132
ggacctaagc aagctgcagt a                                            21

SEQ ID NO: 133      moltype = DNA  length = 20
FEATURE             Location/Qualifiers
source              1..20
                    mol_type = other DNA
                    organism = synthetic construct
SEQUENCE: 133
cagacgacac aggaagcaga                                              20

SEQ ID NO: 134      moltype = DNA  length = 20
FEATURE             Location/Qualifiers
source              1..20
                    mol_type = other DNA
                    organism = synthetic construct
SEQUENCE: 134
accacctcct caaacagctc                                              20

SEQ ID NO: 135      moltype = DNA  length = 20
FEATURE             Location/Qualifiers
source              1..20
                    mol_type = other DNA
                    organism = synthetic construct
SEQUENCE: 135
catagtgtgg tggtgcccta                                              20

SEQ ID NO: 136      moltype = DNA  length = 20
FEATURE             Location/Qualifiers
source              1..20
                    mol_type = other DNA
                    organism = synthetic construct
SEQUENCE: 136
gtggaaggaa atttgcgtgt                                              20

SEQ ID NO: 137      moltype = DNA  length = 20
FEATURE             Location/Qualifiers
source              1..20
                    mol_type = other DNA
                    organism = synthetic construct
SEQUENCE: 137
tgttcacttg tgccctgact                                              20

SEQ ID NO: 138      moltype = DNA  length = 20
FEATURE             Location/Qualifiers
source              1..20
                    mol_type = other DNA
                    organism = synthetic construct
SEQUENCE: 138
gtctgggctt cttgcattct                                              20
```

```
SEQ ID NO: 139         moltype = DNA   length = 20
FEATURE                Location/Qualifiers
source                 1..20
                       mol_type = other DNA
                       organism = synthetic construct
SEQUENCE: 139
tggctctgac tgtaccacca                                                   20

SEQ ID NO: 140         moltype = DNA   length = 20
FEATURE                Location/Qualifiers
source                 1..20
                       mol_type = other DNA
                       organism = synthetic construct
SEQUENCE: 140
acctggtcct ctgactgctc                                                   20

SEQ ID NO: 141         moltype = DNA   length = 20
FEATURE                Location/Qualifiers
source                 1..20
                       mol_type = other DNA
                       organism = synthetic construct
SEQUENCE: 141
cctcaccatc atcacactgg                                                   20

SEQ ID NO: 142         moltype = DNA   length = 19
FEATURE                Location/Qualifiers
source                 1..19
                       mol_type = other DNA
                       organism = synthetic construct
SEQUENCE: 142
gtgcagctgt gggttgatt                                                    19

SEQ ID NO: 143         moltype = DNA   length = 20
FEATURE                Location/Qualifiers
source                 1..20
                       mol_type = other DNA
                       organism = synthetic construct
SEQUENCE: 143
ggaagagaat ctccgcaaga                                                   20

SEQ ID NO: 144         moltype = DNA   length = 20
FEATURE                Location/Qualifiers
source                 1..20
                       mol_type = other DNA
                       organism = synthetic construct
SEQUENCE: 144
atgcctccag ttcaggaaaa                                                   20

SEQ ID NO: 145         moltype = DNA   length = 21
FEATURE                Location/Qualifiers
source                 1..21
                       mol_type = other DNA
                       organism = synthetic construct
SEQUENCE: 145
tgccctgact ttcaactctg t                                                 21

SEQ ID NO: 146         moltype = DNA   length = 20
FEATURE                Location/Qualifiers
source                 1..20
                       mol_type = other DNA
                       organism = synthetic construct
SEQUENCE: 146
ctactgggac ggaacagctt                                                   20

SEQ ID NO: 147         moltype = DNA   length = 20
FEATURE                Location/Qualifiers
source                 1..20
                       mol_type = other DNA
                       organism = synthetic construct
SEQUENCE: 147
gcgcacagag gaagagaatc                                                   20

SEQ ID NO: 148         moltype = DNA   length = 20
FEATURE                Location/Qualifiers
source                 1..20
                       mol_type = other DNA
                       organism = synthetic construct
SEQUENCE: 148
aggtggcctg atcttcacaa                                                   20
```

| | | |
|---|---|---|
| SEQ ID NO: 149 | moltype = DNA   length = 22 | |
| FEATURE | Location/Qualifiers | |
| source | 1..22 | |
| | mol_type = other DNA | |
| | organism = synthetic construct | |
| SEQUENCE: 149 | | |
| tttccttact gcctcttgct tc | | 22 |
| | | |
| SEQ ID NO: 150 | moltype = DNA   length = 20 | |
| FEATURE | Location/Qualifiers | |
| source | 1..20 | |
| | mol_type = other DNA | |
| | organism = synthetic construct | |
| SEQUENCE: 150 | | |
| tggccatcta caagcagtca | | 20 |
| | | |
| SEQ ID NO: 151 | moltype = DNA   length = 17 | |
| FEATURE | Location/Qualifiers | |
| source | 1..17 | |
| | mol_type = other DNA | |
| | organism = synthetic construct | |
| SEQUENCE: 151 | | |
| agccagtcag ccgaagg | | 17 |
| | | |
| SEQ ID NO: 152 | moltype = DNA   length = 18 | |
| FEATURE | Location/Qualifiers | |
| source | 1..18 | |
| | mol_type = other DNA | |
| | organism = synthetic construct | |
| SEQUENCE: 152 | | |
| caccctggct ctgaccat | | 18 |
| | | |
| SEQ ID NO: 153 | moltype = DNA   length = 17 | |
| FEATURE | Location/Qualifiers | |
| source | 1..17 | |
| | mol_type = other DNA | |
| | organism = synthetic construct | |
| SEQUENCE: 153 | | |
| gaccccgcca ctctcac | | 17 |
| | | |
| SEQ ID NO: 154 | moltype = DNA   length = 24 | |
| FEATURE | Location/Qualifiers | |
| source | 1..24 | |
| | mol_type = other DNA | |
| | organism = synthetic construct | |
| SEQUENCE: 154 | | |
| atatttcaat gggtcatatc acag | | 24 |
| | | |
| SEQ ID NO: 155 | moltype = DNA   length = 20 | |
| FEATURE | Location/Qualifiers | |
| source | 1..20 | |
| | mol_type = other DNA | |
| | organism = synthetic construct | |
| SEQUENCE: 155 | | |
| gccatgatcg ctcaaataca | | 20 |
| | | |
| SEQ ID NO: 156 | moltype = DNA   length = 18 | |
| FEATURE | Location/Qualifiers | |
| source | 1..18 | |
| | mol_type = other DNA | |
| | organism = synthetic construct | |
| SEQUENCE: 156 | | |
| acttgcgagg gacgcatt | | 18 |
| | | |
| SEQ ID NO: 157 | moltype = DNA   length = 20 | |
| FEATURE | Location/Qualifiers | |
| source | 1..20 | |
| | mol_type = other DNA | |
| | organism = synthetic construct | |
| SEQUENCE: 157 | | |
| cattctgggg attcttggag | | 20 |
| | | |
| SEQ ID NO: 158 | moltype = DNA   length = 20 | |
| FEATURE | Location/Qualifiers | |
| source | 1..20 | |
| | mol_type = other DNA | |
| | organism = synthetic construct | |
| SEQUENCE: 158 | | |

```
ctgtttcttc ggaggagagc                                               20

SEQ ID NO: 159          moltype = DNA   length = 26
FEATURE                 Location/Qualifiers
source                  1..26
                        mol_type = other DNA
                        organism = synthetic construct
SEQUENCE: 159
ttcctactct tcattgtact tcaacc                                        26

SEQ ID NO: 160          moltype = DNA   length = 20
FEATURE                 Location/Qualifiers
source                  1..20
                        mol_type = other DNA
                        organism = synthetic construct
SEQUENCE: 160
cgtttctgga atccaagcag                                               20

SEQ ID NO: 161          moltype = DNA   length = 20
FEATURE                 Location/Qualifiers
source                  1..20
                        mol_type = other DNA
                        organism = synthetic construct
SEQUENCE: 161
ccaggaacct ctgtgatgga                                               20

SEQ ID NO: 162          moltype = DNA   length = 20
FEATURE                 Location/Qualifiers
source                  1..20
                        mol_type = other DNA
                        organism = synthetic construct
SEQUENCE: 162
cacatgacgg aggttgtgag                                               20

SEQ ID NO: 163          moltype = DNA   length = 18
FEATURE                 Location/Qualifiers
source                  1..18
                        mol_type = other DNA
                        organism = synthetic construct
SEQUENCE: 163
ttccaattcc cctgcaaa                                                 18

SEQ ID NO: 164          moltype = DNA   length = 21
FEATURE                 Location/Qualifiers
source                  1..21
                        mol_type = other DNA
                        organism = synthetic construct
SEQUENCE: 164
gggacaggta ggacctgatt t                                             21

SEQ ID NO: 165          moltype = DNA   length = 21
FEATURE                 Location/Qualifiers
source                  1..21
                        mol_type = other DNA
                        organism = synthetic construct
SEQUENCE: 165
tgacaatggg aatgaaacag a                                             21

SEQ ID NO: 166          moltype = DNA   length = 20
FEATURE                 Location/Qualifiers
source                  1..20
                        mol_type = other DNA
                        organism = synthetic construct
SEQUENCE: 166
ccctagaacc aaatccagca                                               20

SEQ ID NO: 167          moltype = DNA   length = 20
FEATURE                 Location/Qualifiers
source                  1..20
                        mol_type = other DNA
                        organism = synthetic construct
SEQUENCE: 167
ctgcagttca gagggtccag                                               20

SEQ ID NO: 168          moltype = DNA   length = 20
FEATURE                 Location/Qualifiers
source                  1..20
                        mol_type = other DNA
                        organism = synthetic construct
```

```
SEQUENCE: 168
tttgccacgg aaagtactcc                                                  20

SEQ ID NO: 169          moltype = DNA   length = 20
FEATURE                 Location/Qualifiers
source                  1..20
                        mol_type = other DNA
                        organism = synthetic construct
SEQUENCE: 169
ctcacaacct ccgtcatgtg                                                  20

SEQ ID NO: 170          moltype = DNA   length = 20
FEATURE                 Location/Qualifiers
source                  1..20
                        mol_type = other DNA
                        organism = synthetic construct
SEQUENCE: 170
ctccgtcatg tgctgtgact                                                  20

SEQ ID NO: 171          moltype = DNA   length = 20
FEATURE                 Location/Qualifiers
source                  1..20
                        mol_type = other DNA
                        organism = synthetic construct
SEQUENCE: 171
tgctggattt ggttctaggg                                                  20

SEQ ID NO: 172          moltype = DNA   length = 20
FEATURE                 Location/Qualifiers
source                  1..20
                        mol_type = other DNA
                        organism = synthetic construct
SEQUENCE: 172
agctgtttga ggaggtggtg                                                  20

SEQ ID NO: 173          moltype = DNA   length = 20
FEATURE                 Location/Qualifiers
source                  1..20
                        mol_type = other DNA
                        organism = synthetic construct
SEQUENCE: 173
gcagcttgct taggtccact                                                  20

SEQ ID NO: 174          moltype = DNA   length = 20
FEATURE                 Location/Qualifiers
source                  1..20
                        mol_type = other DNA
                        organism = synthetic construct
SEQUENCE: 174
acacgcaaat ttccttccac                                                  20

SEQ ID NO: 175          moltype = DNA   length = 20
FEATURE                 Location/Qualifiers
source                  1..20
                        mol_type = other DNA
                        organism = synthetic construct
SEQUENCE: 175
aaccaccctt aaccctcct                                                   20

SEQ ID NO: 176          moltype = DNA   length = 20
FEATURE                 Location/Qualifiers
source                  1..20
                        mol_type = other DNA
                        organism = synthetic construct
SEQUENCE: 176
cagttgcaaa ccagacctca                                                  20

SEQ ID NO: 177          moltype = DNA   length = 18
FEATURE                 Location/Qualifiers
source                  1..18
                        mol_type = other DNA
                        organism = synthetic construct
SEQUENCE: 177
gcaggtcttg gccagttg                                                    18

SEQ ID NO: 178          moltype = DNA   length = 20
FEATURE                 Location/Qualifiers
source                  1..20
                        mol_type = other DNA
```

```
                           organism = synthetic construct
SEQUENCE: 178
ccagtgtgat gatggtgagg                                                  20

SEQ ID NO: 179          moltype = DNA   length = 20
FEATURE                 Location/Qualifiers
source                  1..20
                        mol_type = other DNA
                        organism = synthetic construct
SEQUENCE: 179
ggggacagca tcaaatcatc                                                  20

SEQ ID NO: 180          moltype = DNA   length = 22
FEATURE                 Location/Qualifiers
source                  1..22
                        mol_type = other DNA
                        organism = synthetic construct
SEQUENCE: 180
tttttctgcc tctttctctt gg                                               22

SEQ ID NO: 181          moltype = DNA   length = 18
FEATURE                 Location/Qualifiers
source                  1..18
                        mol_type = other DNA
                        organism = synthetic construct
SEQUENCE: 181
ctgcacaggg caggtctt                                                    18

SEQ ID NO: 182          moltype = DNA   length = 20
FEATURE                 Location/Qualifiers
source                  1..20
                        mol_type = other DNA
                        organism = synthetic construct
SEQUENCE: 182
gcggagattc tcttcctctg                                                  20

SEQ ID NO: 183          moltype = DNA   length = 21
FEATURE                 Location/Qualifiers
source                  1..21
                        mol_type = other DNA
                        organism = synthetic construct
SEQUENCE: 183
ttcttgtcct gcttgcttac c                                                21

SEQ ID NO: 184          moltype = DNA   length = 24
FEATURE                 Location/Qualifiers
source                  1..24
                        mol_type = other DNA
                        organism = synthetic construct
SEQUENCE: 184
tggattcaca cagacactat caca                                             24

SEQ ID NO: 185          moltype = DNA   length = 20
FEATURE                 Location/Qualifiers
source                  1..20
                        mol_type = other DNA
                        organism = synthetic construct
SEQUENCE: 185
cacaaacacg cacctcaaag                                                  20

SEQ ID NO: 186          moltype = DNA   length = 20
FEATURE                 Location/Qualifiers
source                  1..20
                        mol_type = other DNA
                        organism = synthetic construct
SEQUENCE: 186
actgaccgtg caagtcacag                                                  20

SEQ ID NO: 187          moltype = DNA   length = 20
FEATURE                 Location/Qualifiers
source                  1..20
                        mol_type = other DNA
                        organism = synthetic construct
SEQUENCE: 187
ctgctcacca tcgctatctg                                                  20

SEQ ID NO: 188          moltype = DNA   length = 20
FEATURE                 Location/Qualifiers
source                  1..20
```

```
                        mol_type = other DNA
                        organism = synthetic construct
SEQUENCE: 188
ccaaatactc cacacgcaaa                                                    20

SEQ ID NO: 189          moltype = DNA   length = 16
FEATURE                 Location/Qualifiers
source                  1..16
                        mol_type = other DNA
                        organism = synthetic construct
SEQUENCE: 189
gagggctgg ctggtc                                                         16

SEQ ID NO: 190          moltype = DNA   length = 17
FEATURE                 Location/Qualifiers
source                  1..17
                        mol_type = other DNA
                        organism = synthetic construct
SEQUENCE: 190
gggtcgggtg agagtgg                                                       17

SEQ ID NO: 191          moltype = DNA   length = 18
FEATURE                 Location/Qualifiers
source                  1..18
                        mol_type = other DNA
                        organism = synthetic construct
SEQUENCE: 191
cagctcctca gccaggtc                                                      18

SEQ ID NO: 192          moltype = DNA   length = 25
FEATURE                 Location/Qualifiers
source                  1..25
                        mol_type = other DNA
                        organism = synthetic construct
SEQUENCE: 192
tcaaatcagc tataaatacg aaaca                                              25

SEQ ID NO: 193          moltype = DNA   length = 20
FEATURE                 Location/Qualifiers
source                  1..20
                        mol_type = other DNA
                        organism = synthetic construct
SEQUENCE: 193
tctcaggggg ctaaaggatt                                                    20

SEQ ID NO: 194          moltype = DNA   length = 19
FEATURE                 Location/Qualifiers
source                  1..19
                        mol_type = other DNA
                        organism = synthetic construct
SEQUENCE: 194
gaagaaggga agcggtgac                                                     19

SEQ ID NO: 195          moltype = DNA   length = 23
FEATURE                 Location/Qualifiers
source                  1..23
                        mol_type = other DNA
                        organism = synthetic construct
SEQUENCE: 195
ggaaataaac ctcctccatt ttt                                                23

SEQ ID NO: 196          moltype = DNA   length = 20
FEATURE                 Location/Qualifiers
source                  1..20
                        mol_type = other DNA
                        organism = synthetic construct
SEQUENCE: 196
ccgcctcctt cttcatcata                                                    20

SEQ ID NO: 197          moltype = DNA   length = 20
FEATURE                 Location/Qualifiers
source                  1..20
                        mol_type = other DNA
                        organism = synthetic construct
SEQUENCE: 197
tgcaacgtcg ttacgagtca                                                    20

SEQ ID NO: 198          moltype = DNA   length = 20
FEATURE                 Location/Qualifiers
```

```
                         source                  1..20
                                                 mol_type = other DNA
                                                 organism = synthetic construct
                         SEQUENCE: 198
                         gcagctgatg ggaggaataa                                      20

SEQ ID NO: 199          moltype = DNA   length = 20
                         FEATURE                 Location/Qualifiers
                         source                  1..20
                                                 mol_type = other DNA
                                                 organism = synthetic construct
                         SEQUENCE: 199
                         tgaggatggt gtaagcgatg                                      20

SEQ ID NO: 200          moltype = DNA   length = 19
                         FEATURE                 Location/Qualifiers
                         source                  1..19
                                                 mol_type = other DNA
                                                 organism = synthetic construct
                         SEQUENCE: 200
                         gccagttggc aaaacatct                                       19

SEQ ID NO: 201          moltype = DNA   length = 18
                         FEATURE                 Location/Qualifiers
                         source                  1..18
                                                 mol_type = other DNA
                                                 organism = synthetic construct
                         SEQUENCE: 201
                         cccaacgcac cgaatagt                                        18

SEQ ID NO: 202          moltype = DNA   length = 20
                         FEATURE                 Location/Qualifiers
                         source                  1..20
                                                 mol_type = other DNA
                                                 organism = synthetic construct
                         SEQUENCE: 202
                         agctgttccg tcccagtaga                                      20

SEQ ID NO: 203          moltype = DNA   length = 20
                         FEATURE                 Location/Qualifiers
                         source                  1..20
                                                 mol_type = other DNA
                                                 organism = synthetic construct
                         SEQUENCE: 203
                         tcaccatcgc tatctgagca                                      20

SEQ ID NO: 204          moltype = DNA   length = 25
                         FEATURE                 Location/Qualifiers
                         source                  1..25
                                                 mol_type = other DNA
                                                 organism = synthetic construct
                         SEQUENCE: 204
                         ggtccttttc agaatcaata gtttt                                25

SEQ ID NO: 205          moltype = DNA   length = 21
                         FEATURE                 Location/Qualifiers
                         source                  1..21
                                                 mol_type = other DNA
                                                 organism = synthetic construct
                         SEQUENCE: 205
                         ccaaagcatg gctcatctct a                                    21

SEQ ID NO: 206          moltype = DNA   length = 20
                         FEATURE                 Location/Qualifiers
                         source                  1..20
                                                 mol_type = other DNA
                                                 organism = synthetic construct
                         SEQUENCE: 206
                         ctcaggcaag ctgaaaacat                                      20

SEQ ID NO: 207          moltype = DNA   length = 20
                         FEATURE                 Location/Qualifiers
                         source                  1..20
                                                 mol_type = other DNA
                                                 organism = synthetic construct
                         SEQUENCE: 207
                         gtgacactgc tggaacttcg                                      20

SEQ ID NO: 208          moltype = DNA   length = 20
```

```
FEATURE              Location/Qualifiers
source               1..20
                     mol_type = other DNA
                     organism = synthetic construct
SEQUENCE: 208
tgtctgagca ccacttttgg                                                       20

SEQ ID NO: 209       moltype = DNA   length = 20
FEATURE              Location/Qualifiers
source               1..20
                     mol_type = other DNA
                     organism = synthetic construct
SEQUENCE: 209
tttcctgaac tggaggcatt                                                       20

SEQ ID NO: 210       moltype = DNA   length = 20
FEATURE              Location/Qualifiers
source               1..20
                     mol_type = other DNA
                     organism = synthetic construct
SEQUENCE: 210
ctgcagttca gagggtccag                                                       20

SEQ ID NO: 211       moltype = DNA   length = 16
FEATURE              Location/Qualifiers
source               1..16
                     mol_type = other DNA
                     organism = synthetic construct
SEQUENCE: 211
gacagaaaca ctttat                                                           16

SEQ ID NO: 212       moltype = DNA   length = 15
FEATURE              Location/Qualifiers
source               1..15
                     mol_type = other DNA
                     organism = synthetic construct
SEQUENCE: 212
acactttrcg acaag                                                            15

SEQ ID NO: 213       moltype = DNA   length = 14
FEATURE              Location/Qualifiers
source               1..14
                     mol_type = other DNA
                     organism = synthetic construct
SEQUENCE: 213
cctcaacaag atac                                                             14

SEQ ID NO: 214       moltype = DNA   length = 11
FEATURE              Location/Qualifiers
source               1..11
                     mol_type = other DNA
                     organism = synthetic construct
SEQUENCE: 214
gccgcctgaa a                                                                11

SEQ ID NO: 215       moltype = DNA   length = 12
FEATURE              Location/Qualifiers
source               1..12
                     mol_type = other DNA
                     organism = synthetic construct
SEQUENCE: 215
gcggcatgaa at                                                               12

SEQ ID NO: 216       moltype = DNA   length = 13
FEATURE              Location/Qualifiers
source               1..13
                     mol_type = other DNA
                     organism = synthetic construct
SEQUENCE: 216
cccctcctca gag                                                              13

SEQ ID NO: 217       moltype = DNA   length = 12
FEATURE              Location/Qualifiers
source               1..12
                     mol_type = other DNA
                     organism = synthetic construct
SEQUENCE: 217
cggctcatag gg                                                               12
```

```
SEQ ID NO: 218          moltype = DNA  length = 14
FEATURE                 Location/Qualifiers
source                  1..14
                        mol_type = other DNA
                        organism = synthetic construct
SEQUENCE: 218
aaaccagacc tcag                                                               14

SEQ ID NO: 219          moltype = DNA  length = 12
FEATURE                 Location/Qualifiers
source                  1..12
                        mol_type = other DNA
                        organism = synthetic construct
SEQUENCE: 219
cagctgcaca gg                                                                 12

SEQ ID NO: 220          moltype = DNA  length = 13
FEATURE                 Location/Qualifiers
source                  1..13
                        mol_type = other DNA
                        organism = synthetic construct
SEQUENCE: 220
agacccagt tgc                                                                 13

SEQ ID NO: 221          moltype = DNA  length = 15
FEATURE                 Location/Qualifiers
source                  1..15
                        mol_type = other DNA
                        organism = synthetic construct
SEQUENCE: 221
ttccagtgtg atgat                                                              15

SEQ ID NO: 222          moltype = DNA  length = 15
FEATURE                 Location/Qualifiers
source                  1..15
                        mol_type = other DNA
                        organism = synthetic construct
SEQUENCE: 222
cttccactcg gataa                                                              15
```

DETECTING NEOPLASM

CROSS-REFERENCE TO RELATED APPLICATIONS

This application is a continuation of U.S. patent application Ser. No. 16/738,706, filed Jan. 9, 2020, allowed as U.S. Pat. No. 11,530,449, which is a continuation of U.S. patent application Ser. No. 15/724,890, filed Oct. 4, 2017, now U.S. Pat. No. 10,590,489, which is a continuation of U.S. patent application Ser. No. 15/467,739, filed Mar. 23, 2017, now U.S. Pat. No. 9,803,249, which is a continuation of U.S. patent application Ser. No. 15/197,105, filed Jun. 29, 2016, now U.S. Pat. No. 9,632,093, which is a continuation of U.S. patent application Ser. No. 14/827,013, now U.S. Pat. No. 9,399,800, which is a continuation of U.S. patent application Ser. No. 14/168,552, now U.S. Pat. No. 9,121,070, which is a continuation of U.S. patent application Ser. No. 12/866,558, now U.S. Pat. No. 8,673,555, which is a Section 371 U.S. national stage entry of International Patent Application No. PCT/US2009/033793, filed Feb. 11, 2009, which claims priority to expired U.S. Provisional Patent Application No. 61/029,221, filed Feb. 15, 2008, the contents of which are hereby incorporated by reference in their entireties.

SEQUENCE LISTING

The text of the computer readable sequence listing filed herewith, titled "31196-309_SequenceListing", created Dec. 6, 2022, having a file size of 193,000 bytes, is hereby incorporated by reference in its entirety.

BACKGROUND

1. Technical Field

This document relates to methods and materials involved in detecting premalignant and malignant neoplasms (e.g., colorectal and pancreatic cancer).

2. Background Information

About half of all cancer deaths in the United States result from aero-digestive cancer. For example, of the estimated annual cancer deaths, about 25 percent result from lung cancer; about 10 percent result from colorectal cancer; about 6 percent result from pancreas cancer; about 3 percent result from stomach cancer; and about 3 percent result from esophagus cancer. In addition, over 7 percent of the annual cancer deaths result from other aero-digestive cancers such as naso-oro-pharyngeal, bile duct, gall bladder, and small bowel cancers.

SUMMARY

This document relates to methods and materials for detecting premalignant and malignant neoplasms (e.g., colorectal and pancreatic cancer). For example, this document provides methods and materials that can be used to determine whether a sample (e.g., a stool sample) from a mammal contains a marker for a premalignant and malignant neoplasm such as a marker from a colonic or supracolonic aero-digestive neoplasm located in the mammal. The detection of such a marker in a sample from a mammal can allow a clinician to diagnose cancer at an early stage. In addition, the analysis of a sample such as a stool sample can be much less invasive than other types of diagnostic techniques such as endoscopy.

This document is based, in part, on the discovery of particular nucleic acid markers, polypeptide markers, and combinations of markers present in a biological sample (e.g., a stool sample) that can be used to detect a neoplasm located, for example, in a mammal's small intestine, gall bladder, bile duct, pancreas, liver, stomach, esophagus, lung, or naso-oro-pharyngeal airways. For example, as described herein, stool can be analyzed to identify mammals having cancer. Once a particular mammal is determined to have stool containing a neoplasm-specific marker or collection of markers, additional cancer screening techniques can be used to identify the location and nature of the neoplasm. For example, a stool sample can be analyzed to determine that the patient has a neoplasm, while magnetic resonance imaging (MRI), endoscopic analysis, and tissue biopsy techniques can be used to identify the location and nature of the neoplasm. In some cases, a combination of markers can be used to identify the location and nature of the neoplasm without additional cancer screening techniques such as MRI, endoscopic analysis, and tissue biopsy techniques.

In general, one aspect of this document features a method of detecting pancreatic cancer in a mammal. The method comprises, or consists essentially of determining the ratio of an elastase 3A polypeptide to a pancreatic alpha-amylase polypeptide present within a stool sample. The presence of a ratio greater than about 0.5 indicates that the mammal has pancreatic cancer. The presence of a ratio less than about 0.5 indicates that the mammal does not have pancreatic cancer.

In another aspect, this document features a method of detecting pancreatic cancer in a mammal. The method comprises or consists essentially of determining the level of an elastase 3A polypeptide in a stool sample from the mammal. The presence of an increased level of an elastase 3A polypeptide, when compared to a normal control level, is indicative of pancreatic cancer in the mammal.

In another aspect, this document features a method of detecting pancreatic cancer in a mammal. The method comprises, or consists essentially of, determining the level of a carboxypeptidase B polypeptide in a stool sample from the mammal. An increase in the level of a carboxypeptidase B polypeptide, when compared to a normal control level, is indicative of pancreatic cancer in the mammal.

In another aspect, this document features a method of detecting pancreatic cancer in a mammal. The method comprises, or consists essentially of, determining whether or not a stool sample from the mammal comprises a ratio of a carboxypeptidase B polypeptide to a carboxypeptidase A2 polypeptide that is greater than about 0.5. The presence of the ratio greater than about 0.5 indicates that the mammal has pancreatic cancer.

In another aspect, this document features a method of detecting cancer or pre-cancer in a mammal. The method comprises, or consists essentially of, determining whether or not a stool sample from the mammal has an increase in the number of DNA fragments less than 200 base pairs in length, as compared to a normal control. The presence of the increase in the number of DNA fragments less than 200 base pairs in length indicates that the mammal has cancer or pre-cancer. The DNA fragments can be less than 70 base pairs in length.

In another aspect, this document features a method of detecting colorectal cancer or pre-cancer in a mammal. The method comprises, or consists essentially of, determining whether or not a stool sample from the mammal has an elevated K-ras (Kirsten rat sarcoma-2 viral (v-Ki-ras2) oncogene homolog (GenBank accession no. NM_033360; gi|34485724|)) mutation score, an elevated BMP3 (bone morphogenetic protein 3 (GenBank accession no. M22491; gi|179505)) methylation status, and an elevated level of human DNA as compared to a normal control. The presence of the elevated K-ras mutation score, elevated BMP3 methylation status, and elevated level of human DNA level indicates that the mammal has colorectal cancer or pre-cancer. The K-ras mutation score can be measured by digital melt curve analysis. The K-ras mutation score can be measured by quantitative allele specific PCR.

In another aspect, this document features a method of detecting aero-digestive cancer or pre-cancer in a mammal. The method comprises, or consists essentially of, determining whether or not a stool sample from the mammal has an elevated K-ras mutation score, an elevated BMP3 methylation status, and an elevated level of human DNA as compared to a normal control. The presence of the elevated K-ras mutation score, elevated BMP3 methylation status, and elevated level of human DNA level indicates that the mammal has aero-digestive cancer or pre-cancer. The K-ras mutation score can be measured by digital melt curve analysis. The K-ras mutation score can be measured by quantitative allele-specific PCR. The method can further comprise determining whether or not a stool sample from the mammal has an elevated APC mutation score. The APC mutation score can be measured by digital melt curve analysis.

In another aspect, this document features a method of detecting aero-digestive cancer or pre-cancer in a mammal. The method comprises, or consists essentially of, determining whether or not the mammal has at least one mutation in six nucleic acids selected from the group consisting of p16, p53, k-ras, APC (adenomatosis polyposis coli tumor suppressor (GenBank accession no. NM_00038; gi|189011564)), SMAD4 (SMAD family member 4 (GenBank accession no. NM_005359; gi|195963400)), EGFR (epidermal growth factor receptor (GenBank accession no. NM_005228; gi|413277371)), CTNNB1 (catenin (cadherin-associated protein), beta 1 (88 kD) (GenBank accession no. X87838; gi|1154853|)), and BRAF (B-Raf proto-oncogene serine/threonine-protein kinase (p94) (GenBank accession no. NM_004333; gi|187608632|)) nucleic acids. The presence of at least one mutation in each of the six nucleic acids indicates that the mammal has aero-digestive cancer or pre-cancer. The method can further comprise determining whether or not a stool sample from the mammal has an elevated level of a carboxypeptidase B polypeptide as compared to a normal control. The presence of the elevated level of a caboxypeplidase B polypeptide indicates that the mammal has aero-digestive cancer or pre-cancer in the mammal. The method can further comprise determining whether or not a stool sample from the mammal has an elevated amount of DNA fragments less than 70 base pairs in length as compared to a normal control. The presence of the elevated amount of DNA fragments less than 70 base pairs in length indicates that the mammal has aero-digestive cancer or pre-cancer. The method can further comprise determining whether or not a stool sample from the mammal has an elevated amount of DNA fragments greater than 100 base pairs in length as compared to normal controls. The presence of the elevated amount of DNA fragments greater than 100 base pairs in length indicates that the mammal has aero-digestive cancer or pre-cancer. The method can further comprise determining whether or not a stool sample from the mammal has an elevated BMP3 methylation status. The elevated BMP3 methylation status level indicates that the mammal has aero-digestive cancer or pre-cancer. The determining step can comprise using digital melt curve analysis.

In another aspect, this document features a method of detecting aero-digestive cancer or pre-cancer in a mammal. The method comprises, or consists essentially of, measuring mutations in a matrix marker panel in a stool sample. The marker panel can comprise measuring DNA mutations in p16, p53, k-ras, APC, SMAD4, EGFR, CTNNB1, and BRAF nucleic acids. The presence of a mutation in each of nucleic acids is indicative of the presence of aero-digestive cancer or pre-cancer in a mammal.

In another aspect, this document features a method of detecting aero-digestive cancer in a mammal. The method comprises, or consists essentially of, determining whether or not the methylation status of an ALX4 (aristaless-like homeobox 4 (GenBank accession no. AF294629; gi|108637481)) nucleic acid in a stool sample from the mammal is elevated, as compared to a normal control. The presence of an elevated ALX4 methylation status indicates the presence of aero-digestive cancer in the mammal.

In another aspect, this document features a method of diagnosing pancreatic cancer in a mammal. The method comprises, or consists essentially of, obtaining a stool sample from the mammal, determining the ratio of an elastase 3A poly peptide to a pancreatic alpha-amylase polypeptide present within a stool sample, and communicating a diagnosis of pancreatic cancer if the ratio is greater than about 0.5, thereby diagnosing the mammal with pancreatic cancer.

In another aspect, this document features a method of diagnosing a mammal with pancreatic cancer. The method comprises, or consists essentially of, obtaining a stool sample from the mammal, measuring mutations in a matrix marker panel of nucleic acids present in the sample, determining the ratio of a carboxypeptidase B polypeptide to a carboxypeptidase A2 polypeptide present within the sample, and communicating a diagnosis of pancreatic cancer or pre-cancer if a mutation is detected in each of the marker panel nucleic acids and the ratio is greater than 0.5, thereby diagnosing the mammal. The matrix marker panel comprises or consists essentially of p16, p53, k-ras, APC, SMAD4, EGFR, CTNNB1, and BRAF nucleic acids.

In another aspect, this document features method of diagnosing a mammal with colorectal cancer. The method comprises, or consists essentially of, obtaining a stool sample from the mammal, detecting mutations in a matrix marker panel comprising of p16, p53, k-ras, APC, SMAD4, EGFR, CTNNB1, and BRAF nucleic acids in DNA present within the sample, measuring the level of a serotransferrin polypeptide present within the sample, and communicating a diagnosis of colorectal cancer or pre-cancer if a mutation is detected in each of the nucleic acids and the level of a serotransferrin polypeptide is elevated as compared to a reference level, thereby diagnosing the mammal.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and from the claims.

DETAILED DESCRIPTION

Figure 1:
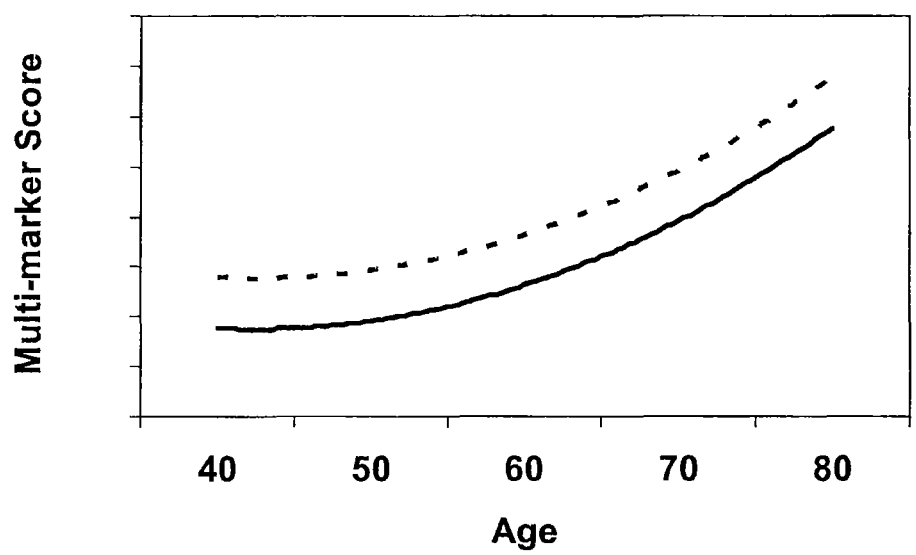
FIG. 1: Adjusted Cut-off Levels with Quantitative Stool Markers to Achieve 95% Specificity across Age and Gender using the Q-LEAD Model. Solid line for women, dotted line for men.

This document provides methods and materials related to detecting a neoplasm in a mammal (e.g., a human). For example, this document provides methods and materials for using nucleic acid markers, polypeptide markers, and combinations of markers present in a biological sample (e.g., a stool sample) to detect a neoplasm in a mammal. Such a neoplasm can be a cancer or precancer in the head and neck, lungs and airways, esophagus, stomach, pancreas, bile ducts, small bowel, or colorectum. It will be appreciated that the methods and materials provided herein can be used to detect neoplasm markers in a mammal having a combination of different neoplasms. For example, the methods and materials provided herein can be used to detect nucleic acid and polypeptide markers in a human having lung and stomach neoplasms.

In some cases, the methods and materials provided herein can be used to quantify multiple markers in biological samples (e.g., stool) to yield high sensitivity for detection of lesions (e.g., neoplasms), while preserving high specificity. Such methods can include, for example, a logistic model that adjusts specificity cut-offs based on age, gender, or other variables in a target population to be tested or screened.

In some cases, the methods and materials provided herein can be used to determine whether a mammal (e.g., a human) has colorectal cancer or pancreatic cancer. For example, serotransferin, methylated BMP3, and mutant BRAF markers in stool can be used to identify a mammal as likely having colorectal cancer, while mutant p16, carboxypeptidase B/A, and elastase 2A markers can be used to identify a mammal as likely having pancreatic cancer.

Any suitable method can be used to detect a nucleic acid marker in a mammalian stool sample. For example, such methods can involve isolating DNA from a stool sample, separating out one or more particular DNAs from the total DNA, subjecting the DNAs to bisulfite treatment, and determining whether the separated DNAs are abnormally methylated (e.g., hypermethylated or hypomethylated). In some cases, such methods can involve isolating DNA from a stool sample and determining the presence or absence of DNA having a particular size (e.g., short DNA). It is noted that a single stool sample can be analyzed for one nucleic acid marker or for multiple nucleic acid markers. For example, a stool sample can be analyzed using assays that detect a panel of different nucleic acid markers. In addition, multiple stool samples can be collected from a single mammal and analyzed as described herein.

Nucleic acid can be isolated from a stool sample using, for example, a kit such as the QIAamp DNA Stool Mini Kit (Qiagen Inc., Valencia, CA). In addition, nucleic acid can be isolated from a stool sample using the following procedure: (1) homogenizing samples in an excess volume (>1:7 w:v) of a stool stability buffer (0.5M Tris pH 9.0, 150 mM EDTA, 10 mM NaCl) by shaking or mechanical mixing; (2) centrifuging a 10 gram stool equivalent of each sample to remove all particulate matter; (3) adding 1 μL of 100 μg/μL RNase A to the supernatant and incubating at 37° C. for 1 hour; (4) precipitating total nucleic acid with 1/10 volume 3M NaAc and an equal volume isopropanol; and (5) centrifuging and then resuspending the DNA pellet in TE (0.01 M Tris pH 7.4, 0.001 M EDTA). U.S. Pat. Nos. 5,670,325; 5,741,650; 5,028,870; 5,952,178, and 6,020,137 also describe various methods that can be used to prepare and analyze stool samples.

One or more specific nucleic acid fragments can be purified from a nucleic acid preparation using, for example, a modified sequence-specific hybrid capture technique (see, e.g., Ahlquist et al. (2000) Gastroenterology, 119:1219-1227). Such a protocol can involve: (1) adding 300 µL of sample preparation to an equal volume of a 6 M guanidine isothiocyanate solution containing 20 pmol biotinylated oligonucleotides (obtained from, for example, Midland Certified Reagent Co., Midland, TX) with sequences specific for the DNA fragments to be analyzed; (2) incubating for two hours at 25° C.; (3) adding streptavidin coated magnetic beads to the solution and incubating for an additional hour at room temperature; (4) washing the bead/hybrid capture complexes four times with IX B+W buffer (1M NaCl, 0.01 M Tris-HCl pH 7.2, 0.001 M EDTA, 0.1% Tween 20); and (5) eluting the sequence specific captured DNA into 35 µL L-TE (1 mM Tris pH 7.4, 0.1 M EDTA) by heat denaturation of the bead/hybrid capture complexes. Any other suitable technique also can be used to isolate specific nucleic acid fragments.

Nucleic acid can be subjected to bisulfite treatment to convert unmethylated cytosine residues to uracil residues, while leaving any 5-methylcytosine residues unchanged. A bisulfite reaction can be performed using, for example, standard techniques: (1) denaturing approximately 1 µg of genomic DNA (the amount of DNA can be less when using micro-dissected DNA specimens) for 15 minutes at 45° C. with 2 N NaOH; (2) incubating with 0.1 M hydroquinone and 3.6 M sodium bisulfite (pH 5.0) at 55° C. for 4-12 hours; (3) purifying the DNA from the reaction mixture using standard (e.g. commercially-available) DNA miniprep columns or other standard techniques for DNA purification; (4) resuspending the purified DNA sample in 55 µL water and adding 5 µl 3 N NaOH for a desulfonation reaction that typically is performed at 40° C. for 5-10 minutes; (5) precipitating the DNA sample with ethanol, washing the DNA, and resuspending the DNA in an appropriate volume of water. Bisulfite conversion of cytosine residues to uracil also can be achieved using other methods (e.g., the CpGenome™ DNA Modification Kit from Serologicals Corp., Norcross, GA).

Any appropriate method can be used to determine whether a particular DNA is hypermethylated or hypomethylated. Standard PCR techniques, for example, can be used to determine which residues are methylated, since unmethylated cytosines converted to uracil are replaced by thymidine residues during PCR. PCR reactions can contain, for example, 10 µL of captured DNA that either has or has not been treated with sodium bisulfate, IX PCR buffer, 0.2 mM dNTPs, 0.5 µM sequence specific primers (e.g., primers flanking a CpG island within the captured DNA), and 5 units DNA polymerase (e.g., Amplitaq DNA polymerase from PE Applied Biosystems, Norwalk, CT) in a total volume of 50 µl. A typical PCR protocol can include, for example, an initial denaturation step at 94° C. for 5 min, 40 amplification cycles consisting of 1 minute at 94° C., 1 minute at 60° C., and 1 minute at 72° C., and a final extension step at 72° C. for 5 minutes.

To analyze which residues within a captured DNA are methylated, the sequences of PCR products corresponding to samples treated with and without sodium bisulfite can be compared. The sequence from the untreated DNA will reveal the positions of all cytosine residues within the PCR product. Cytosines that were methylated will be converted to thymidine residues in the sequence of the bisulfite-treated DNA, while residues that were not methylated will be unaffected by bisulfite treatment.

Purified nucleic acid fragments from a stool sample or samples can be analyzed to determine the presence or absence of one or more somatic mutations. Mutations can be single base changes, short insertion/deletions, or combinations thereof. Methods of analysis can include conventional Sanger based sequencing, pyrosequencing, next generation sequencing, single molecule sequencing, and sequencing by synthesis. In some cases, mutational status can be determined by digital PCR followed by high resolution melting curve analysis. In other cases, allele specific primers or probes in conjunction with amplification methods can be used to detect specific mutations in stool DNA. The mutational signature can comprise not only the event of a base or sequence change in a specific gene, but also the location of the change within the gene, whether it is coding, non-coding, synonymous or non-synonymous, a transversion or transition, and the dinucleotide sequence upstream and downstream from the alteration.

In some cases, a sample can be assessed for the presence or absence of a polypeptide marker. For example, any appropriate method can be used to assess a stool sample for a polypeptide marker indicative of a neoplasm. For example, a stool sample can be used in assays designed to detect one or more polypeptide markers. Appropriate methods such as those described elsewhere (Aebersold and Mann, Nature, 422:198-207 (2003) and McDonald and Yates, Dis. Markers, 18:99-105 (2002)) can be adapted or designed to detect polypeptides in a stool. For example, single-reaction monitoring using a TSQ mass spectrometer can specifically target polypeptides in a stool sample. High resolution instruments like the LTQ-FT or LTQ orbitrap can be used to detect polypeptides present in a stool sample.

The term "increased level" as used herein with respect to the level of an elastase 3A polypeptide is any level that is above a median elastase 3A polypeptide level in a stool sample from a random population of mammals (e.g., a random population of 10, 20, 30, 40, 50, 100, or 500 mammals) that do not have an aero-digestive cancer. Elevated polypeptide levels of an elastase 3A polypeptide can be any level provided that the level is greater than a corresponding reference level. For example, an elevated level of an elastase 3A polypeptide can be 0.5, 1, 2, 3, 4, 5, 6, 7, 8, 9, 10, or more fold greater than the reference level of elastase 3A polypeptide in a normal sample. It is noted that a reference level can be any amount. For example, a reference level for an elastase 3A polypeptide can be zero. In some cases, an increased level of an elastase 3A polypeptide can be any detectable level of an elastase 3A polypeptide in a stool sample.

The term "increased level" as used herein with respect to the level of an carboxypeptidase B polypeptide level is any level that is above a median carboxypeptidase B polypeptide level in a stool sample from a random population of mammals (e.g., a random population of 10, 20, 30, 40, 50, 100, or 500 mammals) that do not have an aero-digestive cancer. Elevated polypeptide levels of carboxypeptidase B poly peptide can be any level provided that the level is greater than a corresponding reference level. For example, an elevated level of carboxypeptidase B polypeptide can be 0.5, 1, 2, 3, 4, 5, 6, 7, 8, 9, 10, or more fold greater than the reference level carboxypeptidase B polypeptide observed in a normal stool sample. It is noted that a reference level can be any amount. For example, a reference level for a carboxypeptidase B polypeptide can be zero. In some cases, an increased level of a carboxypeptidase B polypeptide can be any detectable level of a carboxypeptidase B polypeptide in a stool sample.

The term "increased level" as used herein with respect to the level of DNA fragments less than about 200 or less than about 70 base pairs in length is any level that is above a median level of DNA fragments less than about 200 or less than about 70 base pairs in length in a stool sample from a random population of mammals (e.g., a random population of 10, 20, 30, 40, 50, 100, or 500 mammals) that do not have an aero-digestive cancer. In some cases, an increased level of DNA fragments less than about 200 or less than about 70 base pairs in length can be any detectable level of DNA fragments less than about 200 or less than about 70 base pairs in length in a stool sample.

The term "elevated methylation" as used herein with respect to the methylation status of a BMP3 or ALX nucleic acid is any methylation level that is above a median methylation level in a stool sample from a random population of mammals (e.g., a random population of 10, 20, 30, 40, 50, 100, or 500 mammals) that do not have an aero-digestive cancer. Elevated levels of BMP3 ALX methylation can be any level provided that the level is greater than a corresponding reference level. For example, an elevated level of BMP3 or ALX methylation can be 0.5, 1, 2, 3, 4, 5, 6, 7, 8, 9, 10, or more fold greater than the reference level methylation observed in a normal stool sample. It is noted that a reference level can be any amount.

The term "elevated mutation score" as used herein with respect to detected mutations in a matrix panel of particular nucleic acid markers is any mutation score that is above a median mutation score in a stool sample from a random population of mammals (e.g., a random population of 10, 20, 30, 40, 50, 100, or 500 mammals) that do not have an aero-digestive cancer. An elevated mutation score in a matrix panel of particular nucleic acid markers can be any score provided that the score is greater than a corresponding reference score. For example, an elevated score of K-ras or APC mutations can be 0.5, 1, 2, 3, 4, 5, 6, 7, 8, 9, 10, or more fold greater than the reference score of K-ras or APC mutations observed in a normal stool sample. It is noted that a reference score can be any amount.

In some cases, a ratio of particular polypeptide markers can be determined and used to identify a mammal having an aero-digestive cancer (e.g., a colorectal cancer or a pancreatic cancer). For example, a ratio provided herein (e.g., the ratio of carboxypeptidase B polypeptide levels to carboxypeptidase A2 polypeptide levels) to can be used as described herein to identify a mammal having a particular neoplasm (e.g., pancreatic cancer).

In some cases a matrix marker panel can be used to identify mammals having an aero-digestive cancer a colorectal cancer or a pancreatic cancer). In some cases, such panel also can identify the location of the aero-digestive cancer. Such a panel can include nucleic acid markers, polypeptide markers, and combinations thereof and can provide information about a mutated marker gene, the mutated region of the marker gene, and/or type of mutation. For example, data can be analyzed using a statistical model to predict tumor site (e.g., anatomical location or tissue of origin) based on inputs from sequencing data such as by specific nucleic acid or combination of nucleic acids mutated, specific mutational location on a nucleic acid, and nature of mutation (e.g. insertion, deletion, transition, or transversion) or by any combination thereof) and/or data from polypeptide or other types of markers. For example, a Site of Tumor Estimate (SITE) model can be used to predict tumor site using a matrix panel of markers that are present to variable extent across tumors.

In some cases, data can be analyzed using quantified markers to create a logistic model, which can have both high sensitivity and high specificity. For example, a logistic model can also incorporate population variables like gender and age to adjust cut-off levels for test positivity and thereby optimize assay performance in a screening setting. In some cases, a Quantitative Logistic to Enhance Accurate Detection (Q-LEAD) Model can be used with any marker class or combination of markers as long as they can be quantified.

This document also provides methods and materials to assist medical or research professionals in determining whether or not a mammal has an aero-digestive cancer. Medical professionals can be, for example, doctors, nurses, medical laboratory technologists, and pharmacists. Research professionals can be, for example, principle investigators, research technicians, postdoctoral trainees, and graduate students. A professional can be assisted by (1) determining the ratio of particular polypeptide markers in a stool sample, and (2) communicating information about the ratio to that professional, for example. In some cases, a professional can be assisted by (1) determining the level of human DNA, the methylation status of genes such as BMP3, and the mutation score of genes such as APC and K-ras, and (2) communicating information about the level of DNA, the methylation status of particular genes, and the mutation score of particular genes to the professional. In some cases, a professional can be assisted by (1) detecting mutations in cancer-related genes such as K-ras, p53, APC, p16, EGFR, CTNNB1, BRAF, and SMAD4, as a matrix marker panel, and (2) communicating information regarding the mutations to the professional.

After the ratio of particular polypeptide markers, or presence of particular nucleic acid markers in a stool sample is reported, a medical professional can take one or more actions that can affect patient care. For example, a medical professional can record the results in a patient's medical record. In some cases, a medical professional can record a diagnosis of an aero-digestive cancer, or otherwise transform the patient's medical record, to reflect the patient's medical condition. In some cases, a medical professional can review and evaluate a patient's entire medical record, and assess multiple treatment strategies, for clinical intervention of a patient's condition. In some cases, a medical professional can record a tumor site prediction with the reported mutations. In some cases, a medical professional can request a determination of the ratio of particular polypeptide markers to predict tumor site. In some cases, a medical professional can review and evaluate a patient's entire medical record and assess multiple treatment strategies, for clinical intervention of a patient's condition.

A medical professional can initiate or modify treatment of an aero-digestive cancer after receiving information regarding a ratio of particular polypeptide markers or the presence of nucleic acid markers in a patients stool sample. In some cases, a medical professional can compare previous reports and the recently communicated ratio of particular polypeptide markers, or presence of nucleic acid markers, and recommend a change in therapy. In some cases, a medical professional can enroll a patient in a clinical trial for novel therapeutic intervention of an aero-digestive cancer. In some cases, a medical professional can elect waiting to begin therapy until the patient's symptoms require clinical intervention.

A medical professional can communicate the ratio of particular polypeptide markers to a patient or a patients family. In some cases, a medical professional can provide a patient and/or a patients family with information regarding aero-digestive cancers, including treatment options, prognosis, and referrals to specialists, e.g., oncologists and/or radiologists. In some cases, a medical professional can provide a copy of a patients medical records to communicate the ratio of particular polypeptide markers to a specialist.

A research professional can apply information regarding a subject's ratio of particular polypeptide markers to advance aero-digestive cancer research. For example, a researcher can compile data on the ratio of particular polypeptide markers, and/or presence of particular nucleic acid markers, with information regarding the efficacy of a drug for treatment of aero-digestive cancer to identify an effective treatment. In some cases, a research professional can obtain a subject's ratio of particular polypeptide markers, and/or determine the presence of particular nucleic acid markers to evaluate a subject's enrollment, or continued participation in a research study or clinical trial. In some cases, a research professional can classify the severity of a subjects condition, based on the ratio of particular polypeptide markers and/or the levels of particular nucleic acid markers. In some cases, a research professional can communicate a subject's ratio of particular polypeptide markers, and/or the presence of particular nucleic acid markers to a medical professional. In some cases, a research professional can refer a subject to a medical professional for clinical assessment of an aero-digestive cancer, and treatment of an aero-digestive cancer.

Any appropriate method can be used to communicate information to another person (e.g., a professional). For example, information can be given directly or indirectly to a professional. For example, a laboratory technician can input the ratio of particular polypeptide markers and/or particular nucleic acid markers into a computer-based record. In some cases, information is communicated by making a physical alteration to medical or research records. For example, a medical professional can make a permanent notation or flag a medical record for communicating a diagnosis to other medical professionals reviewing the record. In addition, any type of communication can be used to communicate the information. For example, mail, e-mail, telephone, and face-to-face interactions can be used. The information also can be communicated to a professional by making that information electronically available to the professional. For example, the information can be communicated to a professional by placing the information on a computer database such Mat the professional can access the information. In addition, the information can be communicated to a hospital, clinic, or research facility serving as an agent for the professional.

The invention will be further described in the following examples, which do not limit the scope of the invention described in the claims.

EXAMPLES

Example 1

Multi-Marker Quantitation and a Q-LEAD Model

Most approaches at marker detection in stool have been qualitative. When such qualitative approaches are applied to assay of multiple markers (targeting multiple markers is required with neoplasm detection due molecular heterogeneity), sensitivity is achieved at the expense of compounded non-specificity. Non-specificity can lead to prohibitive programmatic cost with population screening due to the expensive and unnecessary evaluations of false-positive tests. However, if markers are quantified, then a logistic model can be created to achieve both high sensitivity and high specificity. Such a logistic model can also incorporate population variables like gender and age to adjust cut-off levels for test positivity and thereby optimize assay performance in a screening setting (FIG. 1). This Quantitative Logistic to Enhance Accurate Detection (Q-LEAD) Model can be used with any marker class or combination of markers as long as they can be quantified.

A combination of more than one marker was undertaken to achieve the desired sensitivity and specificity for cancer detection. Binary regression methods predicting disease as a function of diagnostic tests estimate the optimal combination of the tests for classifying a subject as diseased or not. McIntosh and Pepe, *Biometrics* 58: 657-664 (2002). A logistic regression model can assess the relationship between a binary dependent response variable such as presence or absence of disease and one or more independent predictor variables. The independent predictors may be qualitative (e.g., binary) or quantitative (e.g., a continuous endpoint). In the Q-LEAD model, the independent predictors can include such biological markers as K-ras, and DNA concentration, and others. Importantly, the model incorporates the demographic variables of gender and age, as we have observed that both age and gender influence molecular marker levels in stool. As average stool marker levels increase with age and male gender, failure to adjust for these variables would yield suboptimal specificity in men and elderly persons tested. Coefficients are estimated from the sample data for each term in the model. The result of the model is a risk score for each subject. Cutoffs for predicting disease state from this risk score can be determined in order to maximize sensitivity and specificity of the marker combinations for predicting disease as desired. The inclusion of demographic variables allows these cutoffs to be determined as a function of age and gender.

As an application of the Q-LEAD Model, the following was performed to evaluate a quantitative stool DNA assay approach targeting three informative markers for the detection of colorectal neoplasia. Subjects included 34 with colorectal cancer, 20 with adenomas >1 cm, and 26 with normal colonoscopy. Subjects added a DNA stabilization buffer with stool collection, and stools were frozen at −80° C. within 72. hours. From thawed stool aliquots, crude DNA was extracted by standard methods, and target genes were enriched by sequence capture K-ras mutation score, methylation of BMP3 gene, and concentration of human DNA (245 bp length) were respectively quantified by a digital melt curve assay, real-time methylation-specific PCR, and real-time Alu PCR, respectively. Assays were performed blinded. A logistic model, which incorporates three markers and gender, was constructed to analyze discrimination by combined markers.

Age medians were 60 for patients with colorectal cancer, 66 for those with adenomas, and 61 for normal controls; and male/female distributions were 23/11, 9/11, and 10/16, respectively. Detection rates of colorectal neoplasms were determined by individual quantitative markers at specificity cutoffs of 96 percent and by combined markers (Table 1). Discrimination by combined markers was calculated using a qualitative binomial method (each marker considered as positive or negative based on individual 96 percent specificity) and by the Q-LEAD model (sensitivity data shown at overall specificity of 96 percent).

TABLE 1

Specificity and sensitivity of cancer markers.

|  | | Sensitivity | |
|---|---|---|---|
| Specificity | Cancers | Adenomas | Both |
| Individual Markers | | | |
| k-ras mutation | 96% | 42% | 32% | 38% |
| BMP3 methylation | 96% | 45% | 32% | 40% |
| DNA concentration | 96% | 65% | 40% | 56% |
| Combined Markers | | | |
| Qualitative method | 88% | 90% | 58% | 78% |
| Q-LEAD Model | 96% | 90% | 47% | 76% |

By quantitative assay and multivariable analysis of an informative marker panel, stool DNA testing can achieve high sensitivity while preserving high specificity for detection of colorectal neoplasia. The particular three-marker combination of mutant K-ras, BMP3 methylation, and human DNA concentration represents a complementary, high-yield panel.

The above data set and additional data were analyzed as follows. A quantitative stool DNA assay approach targeting four informative markers for use in the detection of colorectal cancer and advanced adenoma was evaluated. Subjects comprised 74 patients with colorectal cancer, 27 with an adenoma >1 cm, and 100 with normal colonoscopy. Stools were collected with a stabilization buffer before or >1 week after colonoscopy and were frozen at −80° C. within 24 hours of collection. From thawed stool aliquots, crude DNA was extracted as described above, and target genes were enriched by sequence-specific capture. Human DNA concentration, K-ras and APC mutation scores, and BMP3 methylation were sensitively quantified by real-time Alu PCR, a digital melt curve assay (Zou et al., *Gastroenterology*, "High Detection Rates of Colorectal Neoplasia by Stool DNA Testing With a Novel Digital Melt Curve Assay," (2008)), and real-time methylation-specific PCR, respectively. Assays were performed blindly. Sensitivities and specificities of single makers and their combinations were analyzed.

Age medians were 61 for patients with colorectal cancer, 67 for those with adenomas, and 59 for normal controls; and, male/female ratios were 52/22, 15/12, and 37/63, respectively. The table displays detection rates of colorectal neoplasms by individual quantitative markers at specificities of 90% and by combined markers at two specificities. (Table 2) Data in this table represent a training set and have not been adjusted for age and gender. Yet, it is clear that the full panel of Alu, K-ras, APC, and BMP3 detected more neoplasms than any individual marker, $p<0.05$. At 90% specificity, the full panel detects more adenomas >3 cm (90%, 9/10) than <3 cm (47%, 8/17), $p<0.05$, and more colorectal cancers at stages III-IV (89%, 40/45) than at stages I-II (69%, 20/29) $p<0.05$. Neoplasm detection rates were not affected by tumor location.

TABLE 2

Specificity and sensitivity of a four marker panel

|  | Sensitivity | | | |
|---|---|---|---|---|
|  | Colorectal cancers | | Adenomas | |
| Specificity | I-II | III-IV | ≤3 cm | >3 cm |
| Individual Markers | | | | |
| APC mutation | 90% | 38% | 40% | 47% | 50% |
| k-ras mutation | 90% | 46% | 42% | 24% | 50% |
| BMP3 methylation | 90% | 36% | 38% | 12% | 30% |
| DNA concentration | 90% | 52% | 76% | 41% | 50% |
| Combined Markers | | | | |
|  | 90% | 69% | 89% | 47% | 90% |

In conclusion, a quantitative stool DNA assay system that incorporates a stabilization buffer with specimen collection, high analytical sensitivity, and a panel of broadly informative markers can achieve high detection rates of both colorectal cancers and advanced adenoma.

Example 2

SITE Model and Matrix Marker Panel

A statistical model (Site of Tumor Estimate (SITE)) can be used to predict tumor site (e.g., anatomical location or tissue of origin) based on inputs from sequencing data (such as by specific nucleic acid or combination of nucleic acids mutated, specific mutational location on a nucleic acid, and nature of mutation (e.g. insertion, deletion, transition, or transversion) or by any combination thereof) and/or data from polypeptide or other types of markers.

A matrix marker panel was developed to include eight cancer-related genes: K-ras, p53, APC, p16, EGFR, CTNNB1, BRAF, and SMAD4. The mutation frequencies of these genes were tabulated against the six major aerodigestive cancers based on literature or public database reviews and on actual sequencing observations (Table 3). Literature frequencies were derived from the COSMIC somatic mutation database, review articles, and texts.

TABLE 3

Matrix Panel of Markers by Tumor Site

| AD Cancer Site | N | p16 | p53 | K-ras | APC | SMAD4 | EGFR | CTNNB1 | BRAF | Total Unique |
|---|---|---|---|---|---|---|---|---|---|---|
| Literature | | | | | | | | | | |
| Colorectal |  | <5% | 50-75% | 40% | 85% | 14% | NA | 13% | 20% |  |
| Pancreatic |  | 85-100% | 50-60% | 80-90% | 10-40% | 30% | NA | 3-8% | <5% |  |
| Lung |  | 15-25% | 25-75% | 20-40% | 5% | 7% | 30% | 6% | <5% |  |

TABLE 3-continued

Matrix Panel of Markers by Tumor Site

| AD Cancer Site | N | p16 | p53 | K-ras | APC | SMAD4 | EGFR | CTNNB1 | BRAF | Total Unique |
|---|---|---|---|---|---|---|---|---|---|---|
| Bile Duct | | 15-60% | 30-60% | 40% | 30-40% | 17% | NA | 1% | 14% | |
| Gastric | | 5-30% | 20-50% | 10% | 20-60% | NA | <1% | 30-50% | <5% | |
| Esophageal | | 5-90% | 40-90% | 5-12% | 5-60% | NA | NA | 1% | <5% | |
| Actual (non-dbSNP) | | | | | | | | | | |
| Colorectal | 57 | 5% | 47% | 26% | 75% | 25% | 12% | 2% | 30% | 98% |
| Pancreatic | 24 | 29% | 17% | 62% | 54% | 8% | 8% | 4% | 8% | 83% |
| Lung | 56 | 9% | 57% | 9% | 16% | 14% | 14% | 2% | 4% | 77% |
| Bile Duct | 15 | 13% | 27% | 13% | 20% | 13% | 0 | 0 | 7% | 67% |
| Gastric | 23 | 17% | 22% | 4% | 35% | 17% | 4% | 4% | 0 | 65% |
| Esophageal | 24 | 4% | 46% | 4% | 33% | 17% | 4% | 0 | 4% | 79% |

Some of the frequencies include other genetic alterations than simply single base Changes and small insertions/deletions such as methylation events, large homozygous deletions, and copy number changes. Such alterations would not be reflected in the actual frequency table. Actual frequencies were derived by sequencing coding and flanking gene regions from 245 patient tissue samples reflecting the spectrum of aero-digestive cancers. Only non-synonymous and splice site alterations were tabulated. When specific mutational hot-spot sites were able to be identified for particular genes, only those sites were analyzed.

Figure 12:
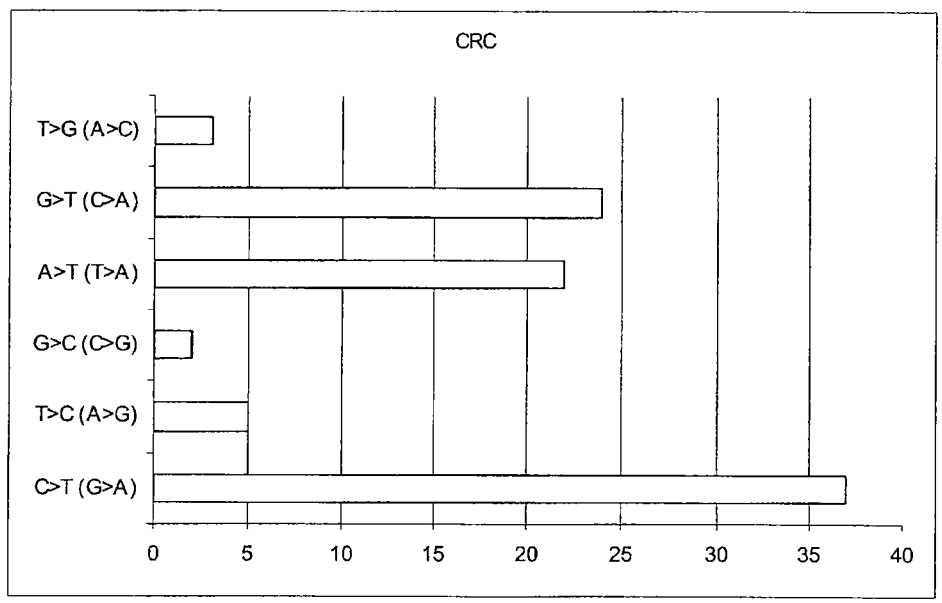
FIG. 12: Frequency of Specific Base Changes in Colorectal Tumors.

The matrix panel includes markers that are present to variable extent across these tumors so that their aggregate use achieves high overall sensitivity and allows prediction of tumor site using the SITE Model. 70% of tumors harbored one or more mutations from the eight gene panel. Some gene mutations, like those associated with p16, are common in tumors above the colon but are rare for those in the colon. Mutant K-ras is frequent with colorectal and pancreatic cancers but infrequent in the other cancers. Mutations in EGFR clustered with lung and colorectal tumors and mutations in SMAD4 clustered with stomach and colorectal tumors. Genes such as p53, are commonly mutated across many different types of cancers, but specific mutational locations or types of mutations within p53 and other genes differ between tumor site (e.g., Greenman et al., Nature, 446(7132):153-8 (2007); Soussi and Lozano, Biochem. Biophys. Res. Commun., 331(3):834-42(2005); Stephens et al., Nat. Genet., 37(6):590-2 (2005); Sjoblom et al., Science, 314(5797):268-74 (2006); Wood et al., Science, 318(5853): 1108-13 (2007); and Davies, Cancer Res., 65(17):7591-5 (2005)) and can be factored in to the SITE Model to predict tumor site. Single base substitutions were the most common type of mutation throughout the panel and those that predicted colorectal tumors included C-G and A-T transversions (FIG. 12). Other tumor sites had similarly unique base change profiles. (Table 4). Insertion/deletions mutations were most common with colorectal tumors, particularly adenomas.

TABLE 4

Specific Base Change Fractions in AD Tumors

| Tumor | C > T (G > A) | T > C (A > G) | G > C (C > G) | A > T (T > A) | G > T (C > A) | T > G (A > C) |
|---|---|---|---|---|---|---|
| Head and Neck | 0.38 | 0.12 | | 0.38 | | 0.12 |
| Esophageal | 0.8 | 0.07 | | | 0.13 | |
| Lung | 0.3 | 0.11 | 0.02 | 0.13 | 0.34 | 0.09 |
| Stomach | 0.5 | 0.25 | | 0.17 | 0.08 | |
| Pancreas | 0.41 | 0.15 | 0.04 | 0.07 | 0.33 | |

TABLE 4-continued

Specific Base Change Fractions in AD Tumors

| Tumor | C > T (G > A) | T > C (A > G) | G > C (C > G) | A > T (T > A) | G > T (C > A) | T > G (A > C) |
|---|---|---|---|---|---|---|
| Bile Duct | 0.5 | | 0.12 | 0.25 | 0.12 | |
| CRA | 0.34 | 0.05 | 0.11 | 0.11 | 0.34 | 0.03 |
| CRC | 0.4 | 0.05 | 0.02 | 0.24 | 0.26 | 0.03 |

Polypeptide markers found in stool, such as by proteomic approaches, can also be used to detect aero-digestive neoplasms and predict tumor site. The following was performed to identify and explore candidate polypeptide markers in stool for the discriminate detection of pancreatic cancer. Subjects included 16 cases with pancreatic cancer, 10 disease controls (colorectal cancer), and 24 healthy controls. Whole stools were collected and frozen promptly in aliquots at −80° C. Thawed aliquots were centrifuged, and the aqueous supernatant from each was analyzed. Polypeptides were separated by 1-D electrophoresis, excised from gels, and digested for mass spectrometric analysis using an LTQ-Orbitrap. Data outputs were searched using Mascot, Sequest, and X! Tandem programs against an updated Swissprot database that included all cataloged species. Unique peptide counts and ratio calculations were performed using Scaffold software.

Figure 2:
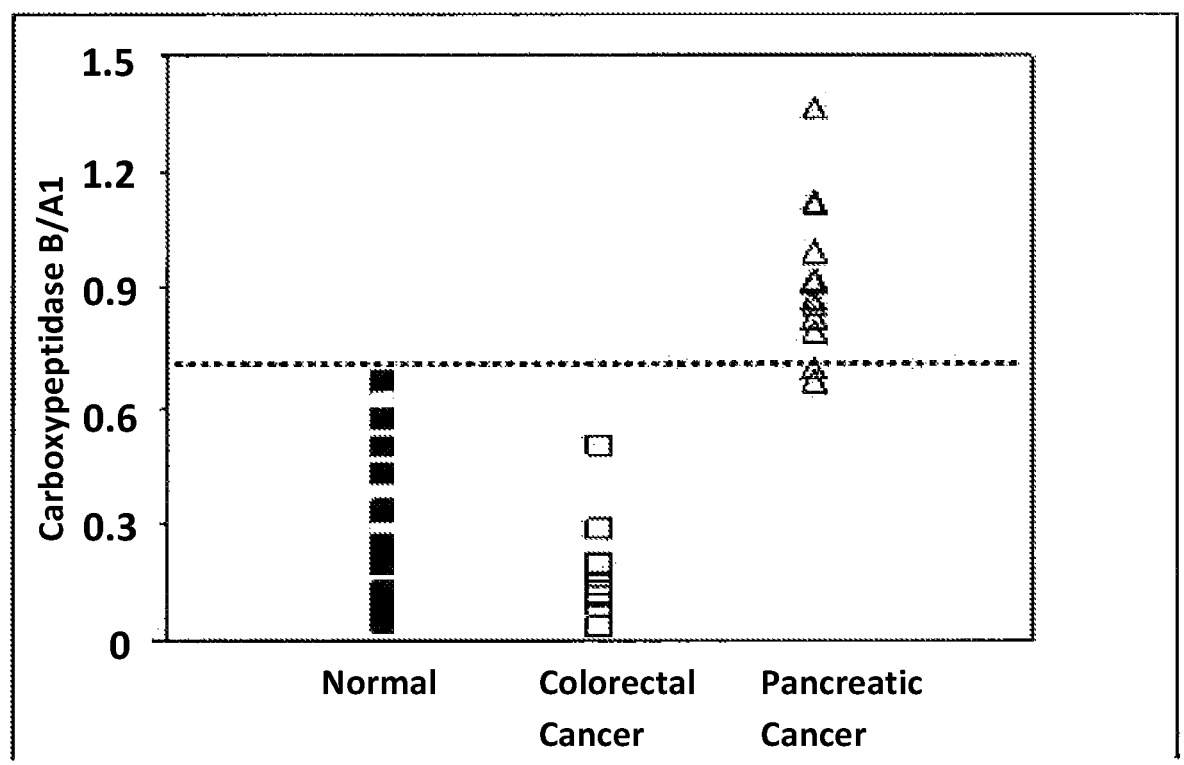
FIG. 2: Sensitive and specific detection of pancreatic cancer by fecal ratio of carboxypeptidase B: carboxypeptidase A2. Note that ratio in stools from patients with colorectal cancer is no different from ratios with healthy controls.

Median age for pancreatic cancer cases was 67, for colorectal cancer controls 63, and for healthy controls 62; and male/female distributions were 9/7, 6/4, and 9/15. respectively. Using shotgun-proteomic techniques on stools, two pancreatic enzymes (carboxypeptidases B and A2) were conspicuous, as unique spectral counts of the former were commonly elevated with pancreatic cancer and of the latter commonly decreased. Considered together as the ratio of carboxypeptidase B/carboxypeptidase A2, pancreatic cancer cases were almost completely separated from colorectal cancer and healthy control groups. Median ratios were 0.9, 0.2, and 0.3, respectively. At a specificity cut-off for the carboxypeptidase B/A2 ratio at 100% (i.e., ratios from normal control and colorectal cancer stools all below cut-off), sensitivity for pancreatic cancer was 86 percent (FIG. 2). Only two pancreatic cancers were misclassified.

These results demonstrate that a stool assay of polypeptide markers can be a feasible non-invasive approach to the detection pancreatic cancer. These results also demonstrate that multivariable analysis of specific polypeptide ratios can be used.

In addition, polypeptide markers unique to colorectal neoplasms were identified (Table 5). For example, serotransferrin was found in stools from patients with colorectal cancer but not in those with pancreatic cancer. These markers when considered as part of a matrix panel contribute both to overall sensitivity for tumor detection and help discriminate colorectal from pancreatic cancer.

TABLE 5

Positive Stool Findings.

| | Carboxypeptidase B/A2* | Serotransferrin |
|---|---|---|
| Colorectal Cancer | 0 | 60% |
| Pancreatic Cancer | 86% | 0 |
| Normal controls | 0 | 0 |

*ratio > 0.75 considered positive

Another polypeptide in stool that is pancreatic cancer specific is elastase 3A. Methods and Results demonstrating this are as follows:

Stool Preparation

Samples were collected in phosphate buffered saline and either dropped off in clinic or mailed in collection tub. Samples were homogenized and frozen within 72 hours after receipt. Frozen stools were diluted 1:3 w:v in PBS (Roche, Cat #1666789). Diluted stools were stomached in a filter bag (Brinkman, BA6041/STR 177×305 mm) for 60 seconds on control setting and spun at 10,000 rpms for 30 minutes. Following an additional 10 minute spin at 14,000 rpm, the supernatant was filtered through a 0.45-μm syringe filter and analyzed. Total protein present in stool was quantitated using a Bradford Protein Assay kit (Pierce).

1-Dimensional Electrophoresis

Stool supernatants were diluted 1:1 in Leammli-BME buffer and run on a 10.5-14% gradient gel. Vertical slices were cut from 250 kDa to 15 kDa and in-gel digested using methods described elsewhere (e.g., Wilm et al., *Nature*, 379:466-469 (1996)). Bands were destained, dehydrated, digested in trypsin, extracted, and lyophilized for MS analysis.

Mass Spectrometry

Lyophilized samples were reconstituted and injected with a flow of 500 nL/min and a 75 minute gradient from 5-90% 98% acetonitrile. MS was performed in data dependent mode to switch automatically between MS and $MS^2$ acquisition on the three most abundant ions. Survey scans were acquired with resolution r=60,000 at 40 m/z using FWHM with a target accumulation of $10^6$ counts. An isolation width of 2.5 m/z was applied. Exclusion mass width was 0.6 m/z on low end and 1.5 m/x on high end. All acquisition and method development was performed using Xcaliber version 2.0.

Database Searching all ms/ms

Samples were analyzed using Mascot (Matrix Science, London, UK; version 2.1.03), Saltiest (ThermoFinnigan, San Jose, CA; version 27, rev. 12) and X! Tandem (World Wide Web at "thegpm.org"; version 2006.09.15.3). Mascot and X! Tandem were searched with a fragment ion mass tolerance of 0.80 Da and a parent ion tolerance of 10.0 PPM. Sequest was searched with a fragment ion mass tolerance of 1.00 Da. Nitration of tyrosine was specified in Mascot as a variable modification.

Criteria the Polypeptide Identification

Scaffold (version Scaffold-01_06_06, Proteome Software Inc., Portland, OR) was used to validate MS/MS based polypeptide identifications. Peptide identifications were accepted if they could be established at greater than 95.0% probability as specified by the Peptide Prophet algorithm (Keller et al, *Anal. Chem.*, 74(20):5383-92 (2002)). Polypeptide identifications were accepted if they could be established at greater than 99.0 percent probability and contained at least two identified peptides. Polypeptide probabilities were assigned by the Protein Prophet algorithm (Nesvizlaskii, *Anal. Chem.*, 75(17):4646-58 (2003)). Polypeptides that contained similar peptides and could not be differentiated based on MS/MS analysis alone were grouped to satisfy the principles of parsimony.

Specific to Elastase SA Ratio Determination

Ratios of elastase 3A were determined using spectral counts for each polypeptide. Ratios were determined by dividing the number of unique peptides of elastase 3A (determined using a composite ID from database search modules Mascot, XTandem, and Seaquest and compiled in Scaffold) by the number of unique peptides from another polypeptide such as pancreatic alpha-amylase.

Results

Figure 3:
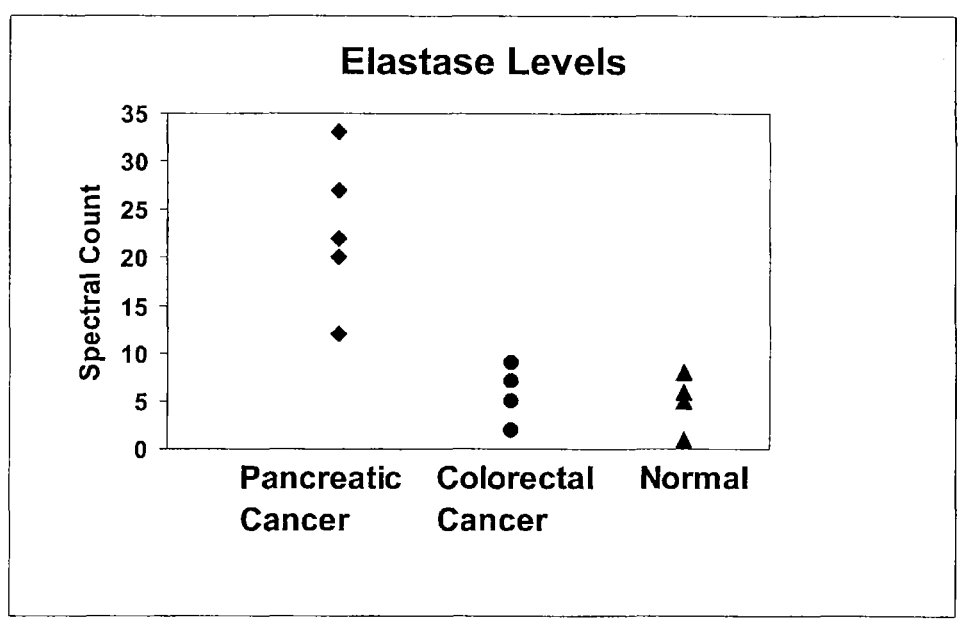
FIG. 3: Elastase levels quantified in stools from patients with pancreatic cancer, patients with colorectal cancer, and healthy controls.
Figure 4:
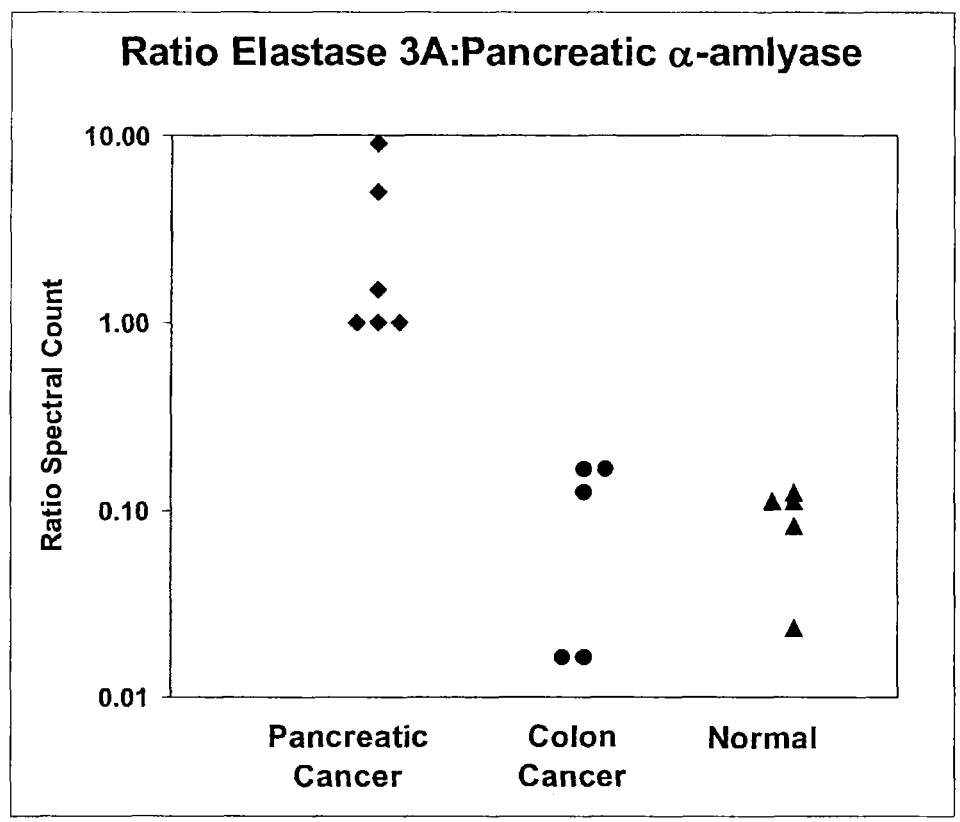
FIG. 4: Ratio of elastase 3A: pancreatic alpha amylase differentiates patients with pancreatic cancer from patients with colorectal cancer and from healthy controls.

The concentration of a specific pancreatic enzyme, elastase 3A, was consistently found to be elevated in the fecal supernatant of patients with pancreatic cancer as compared to normal controls or patients with non-pancreatic cancer (FIG. 3). These finding indicate that fecal concentration of elastase 3A is an accurate marker for pancreatic cancer. In addition, the ratio of elastase 3A against other pancreatic enzymes (or other stable fecal polypeptides) was found to be especially discriminant for pancreatic cancer and obviates the need to determine absolute elastase 3A concentrations (FIG. 4). While mass spectrometry was used to make these observations, elastase 3A levels and ratios including elastase 3A can be measured using other methods as well.

Example 3

Digital Melt Curve Assay for Scanning Mutations

Figure 5:
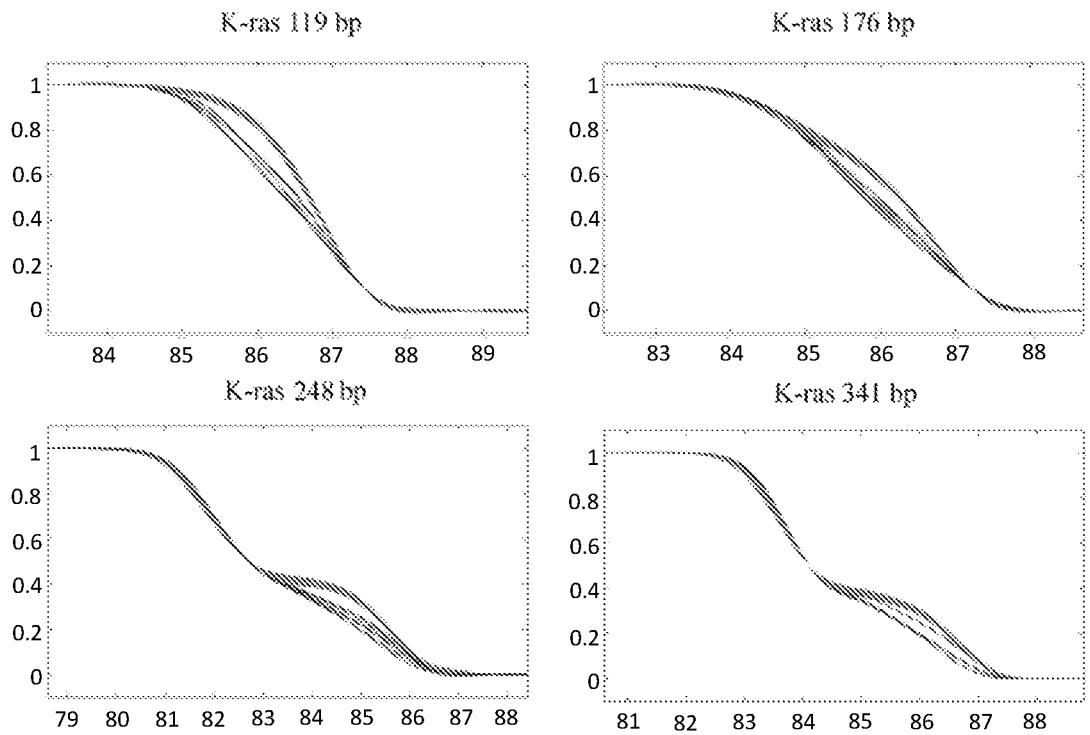
FIG. 5: Digital Melt Curve to detect mutations by targeted gene scanning (temperature (x-axis) v. temperature-normalized fluorescence (y-axis)). Eight pairs of primers, which amplify 100-350 bp gene fragments, were used to scan K-ras and APC genes and detect mutations (substitution and deletion mutations, respectively) at 1% mutant/wild type ratio.
Figure 5:
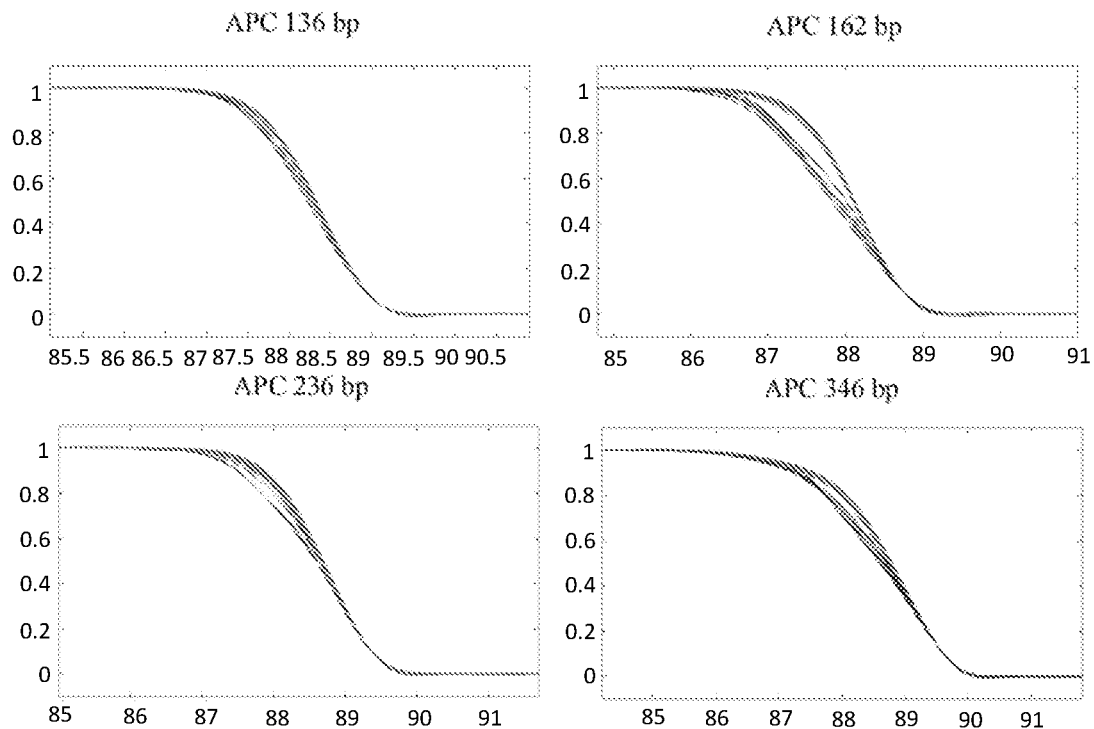
Figure 6:
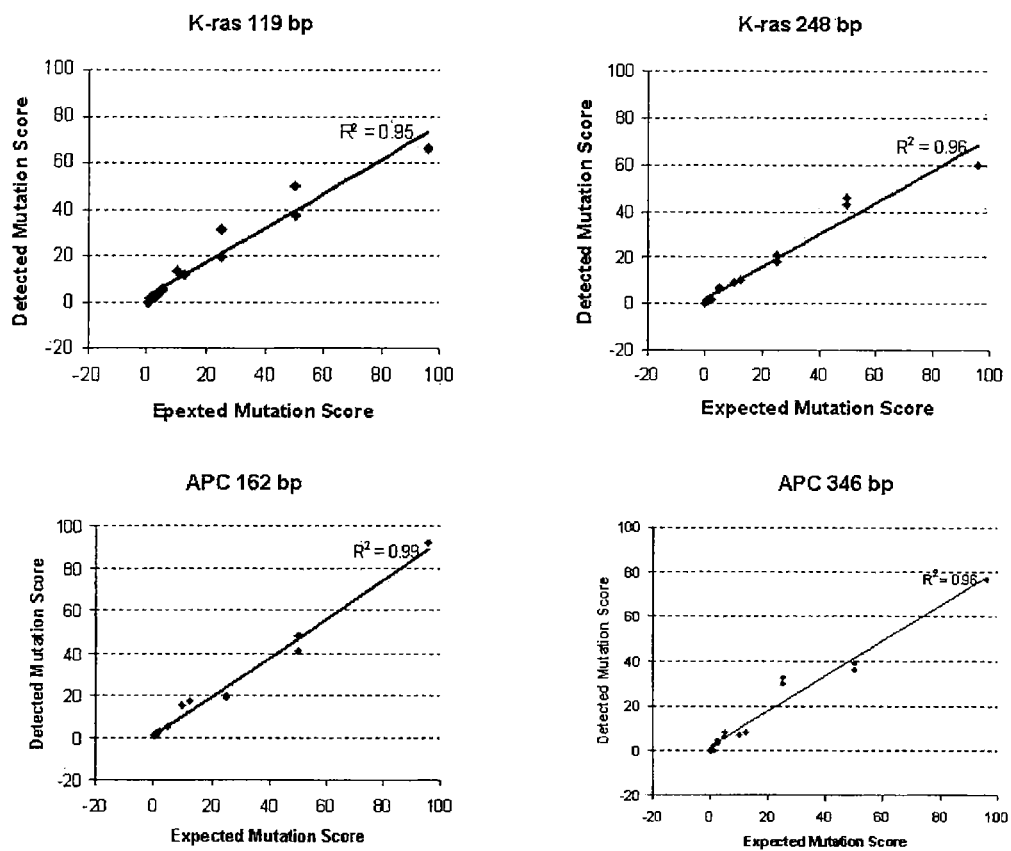
FIG. 6: Quantitive detection of low abundance mutations by Digital Melt Curve Assay. Varying Mutant: Wild-type ratios of K-ras and APC gene mixtures were prepared and assayed blindly by Digital Melt Curve.

A sensitive, rapid, and affordable method for scanning mutations in bodily fluids at high-throughput was developed. A melt curve assay is a post-PCR technique that can be used to scan for mutations in PCR amplicons. Mutations in PCR products can be detected by changes in the shape of the melting curve (heterozygote from mutant sample) compared to a reference sample (homozygote from wild-type sample) (FIG. 5). Melt curve assay can scan all mutations in a DNA fragment <400 bp in less than 10 minutes, rather than individually targeting single mutations. Regular melt curve assays can detect mutations down to a limit of 5% mutant: wild-type and, thus, are not sensitive enough to detect mutations in many biological samples. For instance, in stool, an analytical sensitivity of 1% or less is required in order to detect precancerous polyps or small early stage cancers. Importantly, a quantitative score can be given to density of target mutations (FIG. 6).

Digital PCR can augment the sensitivity of PCR to detect low abundance mutations. Gene copies can be diluted and distributed into 96 wells of a plate to increase the percentage of mutant copy to wild-type copies in certain wells. For example, if a stool DNA sample contains only 1% of mutant BRAF copies compared to wild-type copies, distributing 300 copies of BRAF gene into a 96-well plate can lead to three wells with an average mutant ratio of 33 percent (1:3). After PCR amplification, these three wells with mutant copies can be detected by sequencing or other approaches. Since digital PCR requires PCR on a whole 96-well plate and 96 sequencings (or other approaches) for each target, it can be slow and costly.

The concept of digital melt curve assay is to combine the scanning ability and speed of high resolution melt curve assay with the sensitivity of digital PCR. Miniaturizing and automating this technology dramatically lowers per assay cost and achieves high-throughput necessary for population screening.

The following procedure was used to perform a digital melt curve assay. To prepare a DNA sample, gene target fragments (e.g., BRAF, K-ras, APC, p16, etc.) were captured from stool DNA using a sequence-specific capture method and were quantified with real-time PCR. About 200 to 2000 gene copies were mixed in tube with all PCR reagents. An average of 2 to 20 copies (variable) were distributed to each well of a 96-well plate. PCR amplification was performed using specific primers on the plate (e.g., one target per plate). Final concentrations of PCR mastermix for Digital Melt Curve assays in a 96-well plate (500 µL dispersed to 96 wells with each well containing 5 µL)were as follows: 2×pfx amplification buffer (Invitrogen), 0.3 mM each dNTP, 200 nM forward primer, 200 nM reverse primer, 1 mM MgSO$_4$, 0.02 unit/µL Platinum® pfx polymerase (Invitrogen), and 0.1 unit/µL LcGreen+ dye (Idaho Tech). A high resolution melt curve assay was used to identify the wells with mutant copies. Sequencing was optionally performed to confirm 1 to 2 representative wells.

In some cases, emulsion PCR can be used in place of digital PCR. In such cases, each lipid drop can become a tiny PCR reactor of one single molecule of gene.

TABLE 6

Sequence Specific Capture Probes and DNA Primer

| Gene | Target Region | Capture Probe/Primer | Oligo Sequence (5'→3') | SEQ ID No. |
|---|---|---|---|---|
| KRAS | Condons 12/13 | Probe | GTGGACGAATATGATCCAACAATAGAGGTAAATCTTG | 1 |
| | Condons 12/13 | Primer 1 | AGGCCTGCTGAAAATGACTG | 2 |
| | | | TTGTTGGATCATATTCGTCCAC | 3 |
| | Condons 12/13 | Primer 2 | TAAGGCCTGCTGAAAATGAC | 4 |
| | | | ATCAAAGAATGGTCCTGCAC | 5 |
| | Condons 12/13 | Primer 3 | CGTCTGCAGTCAACTGGAATTT | 6 |
| | | | TGTATCGTCAAGGCACTCTTGC | 7 |
| | Condons 12/13 | Primer 4 | CTTAAGCGTCGATGGAGGAG | 8 |
| | | | TTGTTGGATCATATTCGTCCAC | 3 |
| BRAF | V600E | Probe | CCAGACAACTGTTCAAACTGATGGGACCCACTCCATC | 9 |
| | V600E | Primer | CCACAAAATGGATCCAGACA | 10 |
| | | | TGCTTGCTCTGATAGGAAAATG | 11 |
| APC | MCR | Probe 1 | CAGATAGCCCTGGACAAACCATGCCACCAAGCAGAAG | 12 |
| | MCR | Probe 2 | TTCCAGCAGTGTCACAGCACCCTAGAACCAAATCCAG | 13 |
| | MCR | Probe 3 | ATGACAATGGGAATGAAACAGAATCAGAGCAGCCTAAAG | 14 |
| | Condons 1286-1346 | Primer 1 | TTCATTATCATCTTTGTCATCAGC | 15 |
| | | | CGCTCCTGAAGAAAATTCAA | 16 |
| | Condons 1346-1367 | Primer 2 | TGCAGGGTTCTAGTTTATCTTCA | 17 |
| | | | CTGGCAATCGAACGACTCTC | 18 |
| | Condons 1394-1480 | Primer 3 | CAGGAGACCCCACTCATGTT | 19 |
| | | | TGGCAAAATGTAATAAAGTATCAGC | 20 |
| | Condons 1450-1489 | Primer 4 | CATGCCACCAAGCAGAAGTA | 21 |
| | | | CACTCAGGCTGGATGAACAA | 22 |
| | Condon 1554 | Primer 5 | GAGCCTCGATGAGCCATTTA | 23 |
| | | | TCAATATCATCATCATCTGAATCATC | 24 |
| | 102457delC | Primer 6 | GTGAACCATGCAGTGGAATG | 25 |
| | | | ACTTCTCGCTTGGTTTGAGC | 26 |
| | 102457delC | Primer 7 | CAGGAGACCCCACTCATGTT | 19 |
| | | | CATGGTTTGTCCAGGGCTAT | 27 |
| | 102457delC | Primer 8 | GTGAACCATGCAGTGGAATG | 25 |
| | | | AGCATCTGGAAGAACCTGGA | 28 |
| TP53 | Exon 4 | Probe | AAGACCCAGGTCCAGATGAAGCTCCCAGAATGCCAGA | 29 |
| | Exon 4 | Primer | CCCTTCCCAGAAAACCTACC | 30 |
| | | | GCCAGGCATTGAAGTCTCAT | 31 |
| | Exon 5 | Probe | CATGGCCATCTACAAGCAGTCACAGCACATGACGGAG | 32 |
| | Exon 5 | Primer | CACTTGTGCCCTGACTTTCA | 33 |
| | | | AACCAGCCCTGTCGTCTCT | 34 |
| | Exon 6 | Probe | AGTGGAAGGAAATTTGCGTGTGGAGTATTTGGATGAC | 35 |
| | Exon 6 | Primer | CAGGCCTCTGATTCCTCACT | 36 |
| | | | CTTAACCCCTCCTCCCAGAG | 37 |
| | Exon 7 | Probe | ATGTGTAACAGTTCCTGCATGGGCGGCATGAACCGGA | 38 |
| | Exon 7 | Primer | CTTGGGCCTGTGTTATCCC | 39 |
| | | | GGGTCAGAGGCAAGCAGA | 40 |
| | Exon 8 | Probe | CGCACAGAGGAAGAGAATCTCCGCAAGAAAGGGGAGC | 41 |
| | Exon 8 | Primer | GGGAGTAGATGGAGCCTGGT | 42 |
| | | | GCTTCTTGTCCTGCTTGCTT | 43 |

Example 4

Sensitive Detection of Mutations Using a Digital Melt Curve Assay

The following was performed to develop a quantitative method for scanning gene mutations and to evaluate the sensitivity of the quantitative method for detecting target mutations in stool. A digital melt curve assay was designed by combining digital PCR to a modified melt curve assay. Target genes in low concentration were PCR amplified with a saturated DNA dye, LcGreen+, in a 96-well plate. Each well contained a small number of gene copies, which allowed high mutation/wild-type ratios in some wells that were then detected by melt curve scanning using a LightScanner. Mutations were scored based on the number of wells containing mutant copies in a 96-well plate. To test sensitivity, mutant genes were spiked into a wild-type pool at 0.1, 0.5, 1, 5, and 10% dilutions, and analyzed using digital melt curve assay with 250-1000 gene copies per 96-well plate. This method was then applied in the stool detection of APC, p53, K-ras, and BRAF mutations from 48 patients known to have mutations in one of these genes in matched tumor tissue. Subjects included 9 patients with pancreatic cancer, 31 with colorectal cancer, and 8 with colorectal adenoma >1 cm. All mutations detected by digital melt curve were further confirmed by Sanger sequencing.

Figure 7:
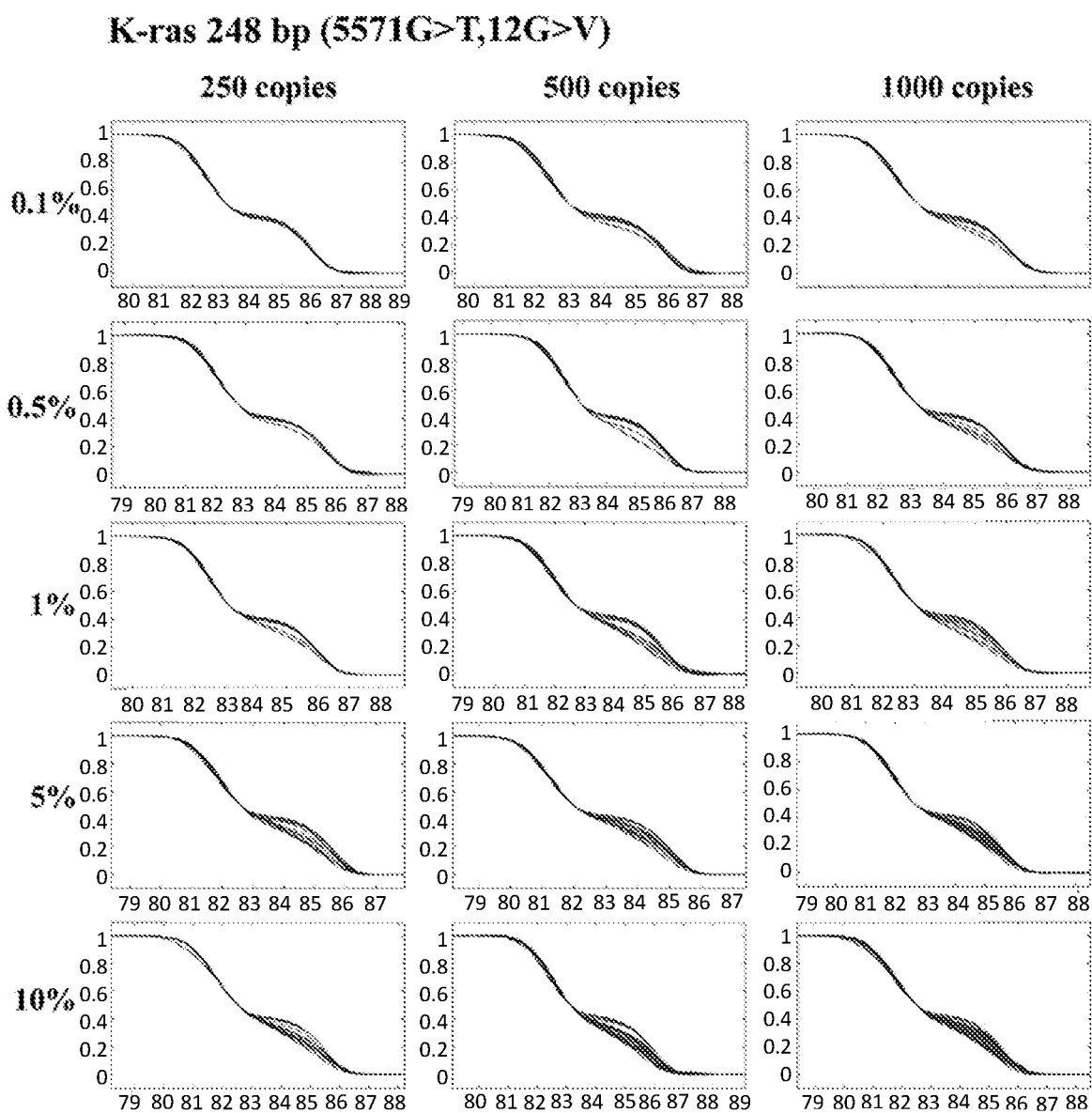
FIG. 7: High analytical sensitivity by Digital Melt Curve (temperature (x-axis) v. temperature-normalized fluorescence (y-axis)). To test the detection limit of digital melt curve (DMC) assay, mutant copies were spiked in wild-type copies at 0.1, 0.5, 1, 5, and 10% dilutions. DMC could detect up to 0.1% mutant/wild-type level when 1000 copies were dispersed to one 96-well plate. The numbers of positive wells increased proportionally when spiked mutant copies were increased. A pair of primers that amplify 248 by K-ras gene fragment were used as an example here. Primers that amplify 119 bp K-ras gene, 162 bp APC gene, and 346 bp APC genes were also used to test the detection limit and quantitative property of DMC.

The digital melt curve assay detected as few as 0.1% mutant copies for amplicons <350 bp using one 96-well plate (FIG. 7), compared to the detection limit for regular melt curve of ≥5 percent. Each mutation scanning took 8-10 minutes with this manual approach. Mutations of APC, p53, K-ras, and BRAF genes were all successfully scanned with digital melt curve in quantitative fashion. Tissue-confirmed mutations were detected from matched stools in 88 percent (42/48) of patients with gastrointestinal neoplasms, including 89 percent with pancreatic cancer, 90 percent with colorectal cancer, and 75 percent with colorectal adenoma >1 cm.

These results demonstrate that a digital melt curve assay can be a highly sensitive approach for detecting mutations in stool, and that it has potential for diagnostic application with both upper and lower gastrointestinal neoplasms.

Example 5

Using a Digital Melt Curve Assay to Detect Adenomas

Archived stools were used to evaluate a digital melt curve assay of DNA markers for detection of advanced adenomas and to compare the accuracy of the digital melt curve assay with that of occult blood testing and a commercial DNA marker assay method (EXACT Sciences). Average risk subjects collected stools without a preservative buffer and mailed them to central processing laboratories for banking and blinded stool testing by Hemoccult, HemoccultSENSA, and DNA marker assay. All subjects underwent a colonoscopy, and tissue from advanced adenomas was archived. Archival stools were selected from the 27 patients with a colorectal adenoma >1 cm found to harbor mutant K-ras on tissue analyses and from the first 25 age and gender matched subjects with normal colonoscopy. Standard methods were used to extract crude DNA from fecal aliquots, and K-ras gene was enriched by sequence capture. Mutations in the K-ras gene were quantified by a digital melt curve assay based on the number of wells containing mutant gene copies in a 96-well plate and confirmed by sequencing.

Figure 8:
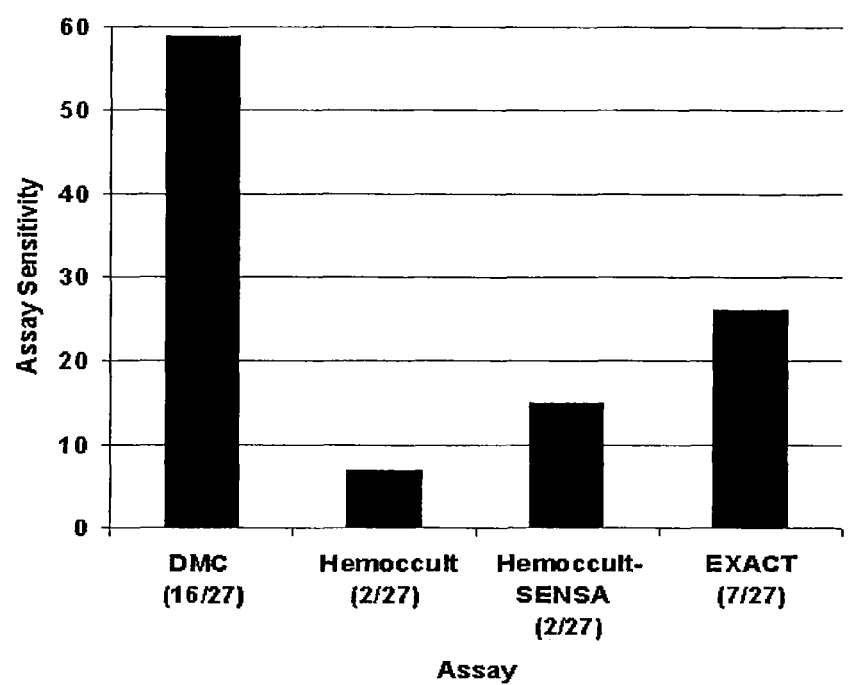
FIG. 8: Superior screen detection of colorectal precancerous polyps by Digital Melt Curve (DMC). Histogram compares sensitivity by DMC with that by common fecal occult blood tests (Hemoccult and HemoccultSENSA) and by the commercial stool DNA test (PreGenPlus, Exact Sciences). Detection by DMC was significantly better than by any other test ($p<0.05$).

Median age with adenomas was 67 and controls 71; and males/females were 12/15 and 13/14, respectively. Median adenoma size was 1.5 cm (range 1-3 cm). Based on a cut-off of >3 wells with mutant K-ras, the digital melt curve assay yielded an overall sensitivity of 59 percent for adenomas with a specificity of 92 percent; sensitivity for adenomas >2 cm was 80 percent (8/10) and for those <2 cm was 47 percent (8/17), p=0.1. In these same stools, overall adenoma detection rates were 7 percent by Hemoccult, 15 percent by HemoccultSENSA, and 26 percent by the EXACT Sciences K-ras assay (p<0.05 for each vs. digital melt curve) (FIG. 8). Respective specificities were 92 percent, 92 percent, and 100 percent.

These results demonstrate that an analytically-sensitive digital melt curve assay method can be used to detect a majority of advanced colorectal adenomas and improve yield over current stool test approaches.

Example 6

Short DNA as a Cancer Marker

Free human DNA is present in all human stools and arises from cells shed (exfoliated) from the normal surface (mucosa) of the aero-digestive tract (mouth/throat, lungs, and all digestive organs) and from tumors or other lesions that may be present. It has been generally accepted that "long DNA" in stool reflects that presence of colorectal and other aero-digestive tumors, in that cells exfoliated from cancers do not undergo typical cell death (apoptosis) which would shorten DNA. Specifically, because DNA from apoptotic cells would be broken down to fragment lengths shorter than 100 bp, long DNA was defined as being longer than 100 bp. Indeed, levels of long DNA were elevated in stools from patients with colorectal and other cancers as compared to those from healthy controls (Zou et al., *Cancer Epidemiol. Biomarkers Prev.*, 15: 115 (2006); Ahlquist et al., *Gastroenterology*, 119:1219 (2000); and Boynton et al, *Clin. Chem.*, 49:1058 (2003)). As such, long DNA in stool can serve as a marker for colorectal and other tumors.

Figure 9:
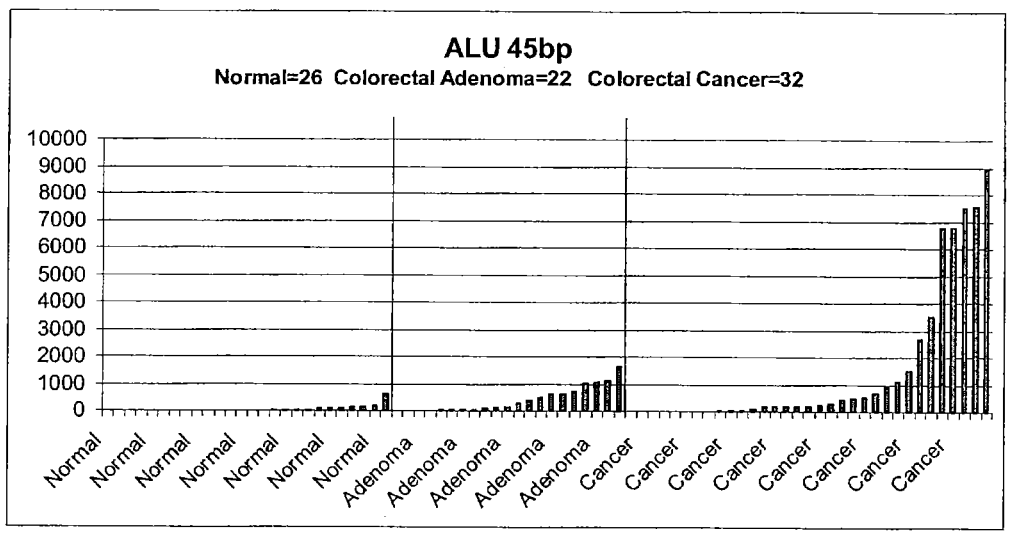
FIG. 9: Distributions of short fragment human DNA (short DNA) and long fragment human DNA (long DNA) in stools from patients with normal colonoscopy, large precancerous adenomas, and colorectal cancer. Human DNA quantified by an assay of Alu repeats. Short DNA represents 45 bp fragment amplification products, and long DNA represents 245 bp amplification products.
Figure 9:
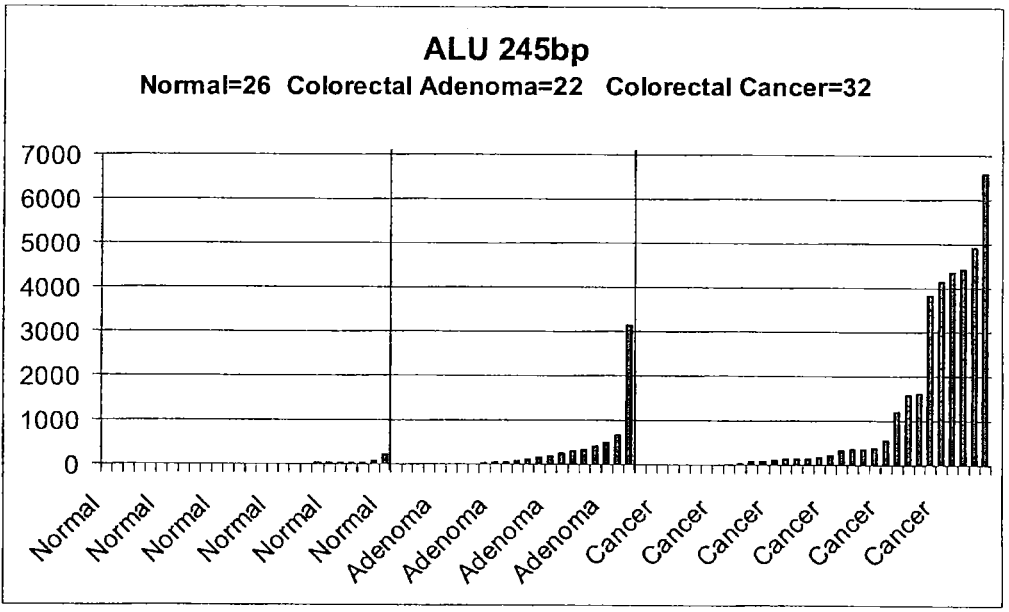
Figure 10:
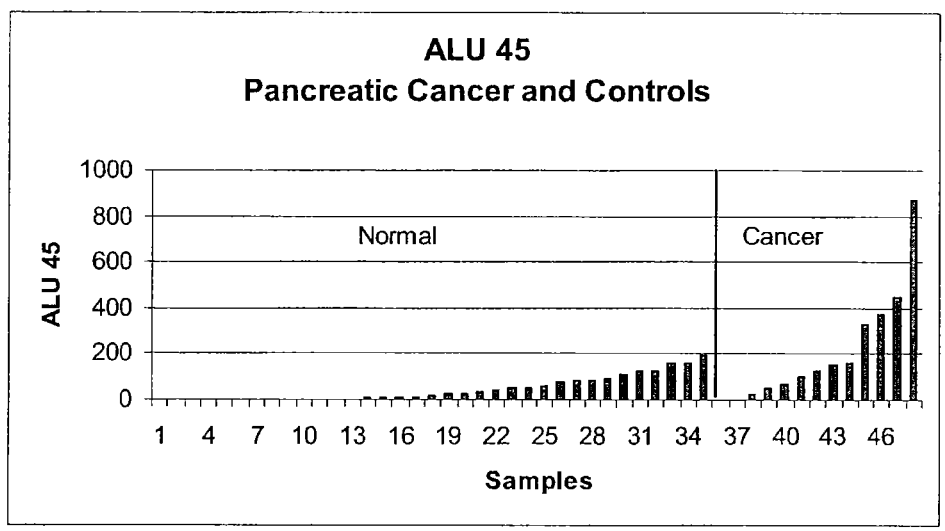
FIG. 10: Stool distributions of short and long DNA in patients with pancreatic cancer and in healthy controls. Short DNA represents 45 bp fragment amplification products, and long DNA represents 245 bp amplification products.
Figure 10:
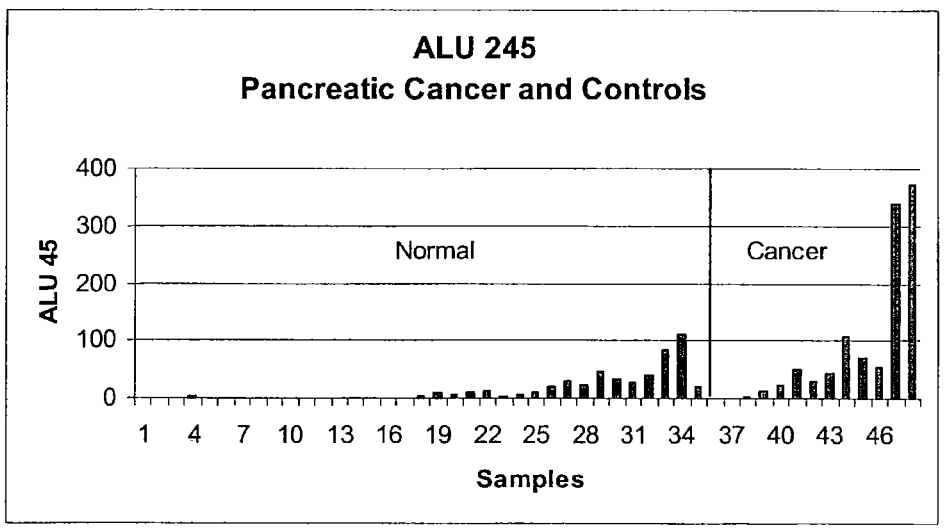

"Short DNA" (i.e., <100 bp in length), however, was found to be as or more discriminant than long DNA as a tumor marker in stool for detection of both colorectal (FIG. 9) and pancreatic (FIG. 10) neoplasia.

Briefly, methods and materials similar to those described elsewhere were used to detect short DNA present in stool samples (Zou et al., *Cancer Epidemiol. Biomarkers Prev.*, 15(6): 1115 (2006)). Total DNA was extracted by isopropanol precipitation from 19 blinded stool samples: 9 pancreatic adenocarcinoma, and 10 age/gender matched normals. The DNA pellets were taken up in 8 mL of 10-fold diluted TE, pH 8. The Alu sequence consists of conserved regions and variable regions. In the putative consensus Alu sequence, the conserved regions are the 25-bp span between nucleotide positions 23 and 47 and the 16-bp span between nucleotide positions 245 and 260. Although primers can be designed in any part of the Alu sequences, for more effectively amplifying Alu sequences, the PCR primers are preferably completely or partially (at least the 3'-regions of the primers) located in the conserved regions. Primers specific for the human Alu sequences were used to amplify fragments of differing lengths inside Alu repeats. The sequences were as follows:

| Amplicon size | Primer Sequences |
|---|---|
| 245 bp | Forward Primer: 5'-ACGCCTGTAATCCCAGCACTT-3' (SEQ ID NO: 44)<br>Reverse Primer: 5'-TCGCCCAGGCTGGAGTGCA-3' (SEQ ID NO: 45) |
| 130 bp | Forward Primer: 5'-TGGTGAAACCCCGTCTCTAC-3' (SEQ ID NO: 46)<br>Reverse Primer: 5'-CTCACTGCAACCTCCACCTC-3' (SEQ ID NO: 47) |
| 45 bp | Forward Primer: 5'-TGGTGAAACCCCGTCTCTAC-3' (SEQ ID NO: 46)<br>Reverse Primer: 5'-CGCccGGCTAATTTTTGTAT-3' (SEQ ID No: 48) |

Stool DNA was diluted 1:5 with 1×Tris-EDTA buffer (pH 7.5) for PCR amplification. Tris-EDTA buffer-diluted stool DNA (1 µL) was amplified in a total volume of 25 µL containing 1×iQ SYBR Green Supermix (Bio-Rad, Hercules, CA), 200 nmol/L each primer under the following conditions: 95° C. for 3 minutes followed by 40 cycles of 95° C., 60° C., and 72° C. for 30 seconds each. A standard curve was created for each plate by amplifying 10-fold serially diluted human genomic DNA samples (Novagen, Madison, WI). Melting curve analysis was made after each PCR to guarantee that only one product was amplified for all samples.

Amplification was carried out in 96-well plates in an iCycler (Bio-Rad). Each plate consisted of stool DNA samples and multiple positive and negative controls. Each assay was done in duplicate.

The following was performed to compare DNA (245 bp) and short (45 bp) human DNA in stool for detection of upper and lower GI neoplasms, and to assess the effect of GI tumor site on human DNA levels in stool. Subjects included 33 patients with colorectal cancer, 20 with colorectal adenomas >1 cm, 13 with pancreatic cancer, and 33 colonoscopically-normal controls. Subjects added a preservative buffer to stools at time of collection to prevent post-defecation bacterial metabolism of DNA, and stools were frozen within 8 hours at −80° C. Using a validated quantitative assay for human DNA (Zou et al. *Epidemiol. Biomarkers Prev.*, 15:1115 (2006)), 245 bp and 45 bp Alu sequences were amplified from all stools in blinded fashion. Sensitivities for long and short DNA were based on 97 percent specificity cut-offs.

Age medians were 60, 66, 69, and 62 for colorectal cancer, colorectal adenoma, pancreatic cancer, and control groups, respectively; and male/female distributions were 22/11, 9/11, 9/4, 11/21, respectively. In stools from neoplasm. and control groups, amplification products were quantitatively greater for short DNA versus long DNA. Respective sensitivities by long and short DNA were 66 percent and 62 percent with the 29 distal colorectal neoplasms, 46 percent and 46 percent with the 24 proximal colorectal neoplasms, and 15 percent and 31 percent (p=0.16) with the 13 pancreatic cancers. By Wilcoxan Rank-Sum test, effect of neoplasm site on detection rates was significant for both long DNA (p=0.004) and short DNA (p=0.02). Among colorectal neoplasms, respective sensitivities by long and short DNA were 48 percent and 52 percent with lesions <3 cm, 63 percent and 63 percent with those >3 cm, 64 percent and 61 percent with cancers, and 35 percent and 45 percent with adenomas.

These results demonstrate that short and long DNA can be comparably sensitive for stool detection of GI neoplasms. However, detection rates vary with tumor site, being greatest with the most distal lesions and lowest with the most proximal ones. These results were consistent with substantial luminal degradation of DNA exfoliated from more proximal GI neoplasms.

It was also demonstrated that mutant gene markers in stool can be detected to a greater extent if amplicon size is less than 70 bp, consistent with luminal degradation. Thus, short DNA can serve as a marker per se and as the target size for imitation detection.

Example 7

Use of Fecal Methylated BMP3 as a Neoplasia Marker

Figure 11:
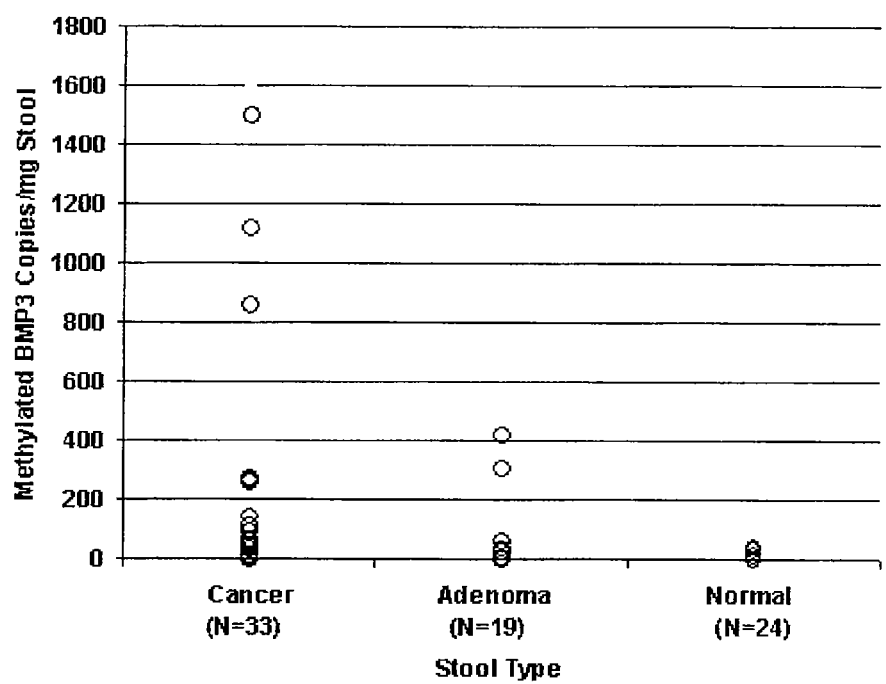
FIG. 11: Methylated BMP3 gene in stool for detection of colorectal neoplasia. Methylated BMP3 was blindly quantified in stools from patients with colorectal cancers, precancerous adenomas, and normal individuals with real-time methylation-specific PCR. Each circle represents a stool sample.

Stools from patients with colorectal tumors were found to contain significantly elevated amounts of methylated BMP3 gene copies, but those from normal individuals were found to contain none or only trace amounts. When fecal methylated BMP3 was assayed with an appropriate amplification method, colorectal cancers and premalignant adenomas were specifically detected (FIG. 11). Fecal methylated BMP3 detected a higher percentage of proximal colon tumors than distal tumors, so it can be combined with markers for distal colorectal tumors to create complementary marker panels. Fecal methylated BMP3 was very specific with few false-positive reactions.

Similar results can be obtained using other genes and methods such as those described elsewhere (Zou et al., *Cancer Epidemiol. Biomarkers Prev.*, 16(12):2686 (2007)).

Example 8

Detecting Aero-Digestive Cancers by Stool DNA Testing

Tissue samples from patients with confirmed aero-digestive tumors were extracted and sequenced to assess the presence or absence of somatic gene alterations. Germline DNA from the same patients were used as controls. Once an alteration was confirmed, a matched stool sample was tested for that alteration. Two separate methods were utilized to detect the mutation in stool: Allele specific PCR and digital melt curve analysis. For both methods, we focused on amplifying the shortest fragments possible (>100 bp) that have been shown to contain higher levels of the mutant sequence.

Digital Melt Curve (DMC)

We studied 138 patients (69 cases with a GI neoplasm and 69 age/sex-matched asymptomatic controls with normal colonoscopy) by first, identifying a mutation in neoplasm tissue, and then determining if that specific mutation could be detected in stool from that individual. Stools were collected with a stability buffer and frozen at −80° C. until assayed.

Genes commonly mutated in GI neoplasms (TP3, KRAS, APC, CDH1, CTNNB1, BRAF, SMAD4, and P16) were sequenced from DNA extracted from tumor tissue, to identify a target mutation for each case. Target genes were isolated by hybrid capture (Table 7) and the tissue-confirmed somatic mutations were assayed in stool by the digital melt curve method, as described in Example 1. Mutations detected in stool were confirmed by sequencing. Assays were performed blinded.

TABLE 7

Sequence Specific Capture Probes and Primers for AD Cancer Mutation Detection

| MUTATION IN TISSUE | CAPTURE PROBE | SEQ ID No. | SENSE PRIMER 1 (5' TO 3') | SEQ ID No. | ANTISENSE PRIMER 2 (5' TO 3) | SEQ ID No. |
|---|---|---|---|---|---|---|
| 12487C > CT:167Q > Q/X | ATGGCCATTCACAAGCAGTCATAGCACATGACGGAGGTTGT | 49 | AGTACTCCCCTGCCCTCAAC | 128 | CTCACAACCTCCGTCATGTG | 169 |
| 102447_102450het_delTGGT | AGAGTGAACCATGCAGTCGAGTGGAAAAGTGGCATTATAAGCCC | 50 | TTTGAGAGTCGTTCGATTGC | 129 | CATGGTTTGTCCAGGGCTAT | 27 |
| 12410G > GA, 141C > C/Y | TTTGCCAACTGCCAAGACCTACCCTGTGCAGTCTGTG | 51 | AGTACTCCCCTGCCCTCAAC | 128 | CTCCGTCATGTGTCTGACT | 170 |
| 102678het_delA | CAGATGCTGATACTTTATTACTTTTGCCACGAAAGTACT | 52 | TCCAGGTTCTTCCAGATGCT | 130 | CACTCAGGCTGGATGAACAA | 22 |
| 102594_102598het_delAGAGA | AAAGCACCTACTGCTGAAAGAGAGTGGACCTAAGCAAG | 53 | AGCTCAAACCAAGCGAGAAG | 131 | AGCATCTGAAGAACCTGA | 28 |
| 102644_102646het_insG | ATGCTGCAGTTCAGAGGGGTCCAGTTCTTCCAGATGC | 54 | GGACCTAAGCAAGCTGCAGTA | 132 | CACTCAGGCTGGATGAACAA | 22 |
| 102594_102595het_delAG | TAAAGCACCTACTGCTGAAAAGAGGAGAGTGGACCTAAGCAAG | 55 | AGCTCAAACCAAGCGAGAAG | 131 | AGCATCTGAAGAACCTGA | 28 |
| 102106het_delT | CACAGGAAGCAGATTCTGCAATACCCTGCAAATAGCA | 56 | CAGACGACACAGGAAGCAGA | 133 | TGCTGGATTTGGTTCTAGGG | 171 |
| 102442het_delT | TTCAGAGTGAACCATGCAGGGAATGGTAAGTGGCATTAT | 57 | TTTGAGAGTCGTTCGATTGC | 129 | CATGGTTTGTCCAGGGCTAT | 27 |
| apc 102494C > CT; 142Q > Q/X | TCCAGATAGCCCTGATAAACCATGCCACCAAG | 58 | GTGAACCATGCAGTGGAATG | 25 | AGCTGTTTGAGGAGGTGGTG | 172 |
| apc 102557C > CT; 1450R > R/X | CTCAAACAGCTCAAACCAGTGAAGTACCTAAAAAT AAA | 59 | ACCACCTCCTCAAACAGCTC | 134 | GCAGCTTGCTTAGTCCACT | 173 |
| apc 102140het_delA | AGCAGAAATAAAAGAAAAGTTGGAACTAGGTCAGCTGA | 60 | CAGACGACACAGGAAGCAGA | 133 | TGCTGGATTTGGTTCTAGGG | 171 |
| apc 102494C > CT; 142Q > Q/X | TCCAGATAGCCCTGATAAACCATGCCACCAAG | 58 | GTGAACCATGCAGTGGAATG | 25 | AGCTGTTTGAGGAGGTGGTG | 172 |
| apc 102554het_delA | CTCAAACAGCTCAAACCAGCGAGAAGTACCTAAA | 61 | CATGCCACCAAGCGAGAAGTA | 21 | GCAGCTTGCTTAGTCCACT | 173 |
| tp53 E5 12647A > AG: 193H > H/R | TCTGCCCCTCCCTCAGCGTCTTATCGAGTGGAAG | 62 | CAGGCCTCTGATTCCTCACT | 36 | ACACGCAAATTCTTCCAC | 174 |
| tp53 E5 12742G > GA | CCTATGAGCGCCTGGAGATCTGGTTTGCAACTGGG | 63 | CATAGTGTGGTGGTGCCCTA | 135 | AACCACCCTTAACCCCTCCT | 175 |
| tp53 E5 12706C > CT:213R > R/X | ATGCAGAAACACTTTTGGACATAGTGTGGTGGTG | 64 | GTGGAAGGAAATTTGCGTGT | 136 | CAGTTGCAAACCAGACCTCA | 176 |
| tp53 E4 12712A > AG:215S > S/G | GAAACACTTTTCGACATGTGTTGCCAACTGGCCAAG | 65 | GTGGAAGGAAATTTGCGTGT | 136 | CAGTTGCAAACCAGACCTCA | 176 |
| tp53 E4 12388T > TC:134F > F/L | CTGCCCTCAACAGATGCTTTGCCACAGTCAGTTGCCCTGAGGG | 66 | TGTTCACTTGTGCCCTGACT | 137 | GCAGGTCTTGGCCAGTTG | 177 |
| tp53 E3 11606G > GA:125T > T/T | AAGTCTGTGACTTGCACAGTCAGTTGCCTTGCATTCT | 67 | GTCTGGGCTTCTTGCATTCT | 138 | GCCAGGCATTGAAGTCTCAT | 31 |
| tp53 E6 13379C > CT:248R > R/W | GCATGGGCGGCATGAACTGGAGGCCCATCCTCACC | 68 | TGGCTCTGACTGTACCACCA | 139 | CCAGTGTGATGATGTGAGG | 178 |

TABLE 7-continued

Sequence Specific Capture Probes and Primers for AD Cancer Mutation Detection

| MUTATION IN TISSUE | CAPTURE PROBE | SEQ ID No. | SENSE PRIMER 1 (5' TO 3') | SEQ ID No. | ANTISENSE PRIMER 2 (5' TO 3) | SEQ ID No. |
|---|---|---|---|---|---|---|
| tp53 12E3 11326A > AC (splice site) | TCTTTTCACCCATCTACCCCCTTGCCGTCCC | 69 | ACCTGGTCCTCTGACTGCTC | 140 | GGGGACAGCATCAAATCATC | 179 |
| tp53 E6 13412G > GT:259D > D/Y | CCATCATCACACTGGAATATCCAGGTCAGGAGCC | 70 | CCTCACCATCATCACACTGG | 141 | GGGTCAGAGGCAAGCAGA | 40 |
| tp53 E4 12449G > GT:154G > G/V | ACCCCCGCCCGTCACCCGCGTCC | 71 | GTGCAGCTGTGGGTTGATT | 142 | CTCCGTCATGTGCTGTGACT | 170 |
| tp53 E7 13872G > GT,298E > E/X | GGAACAGCTTTGAGGTGTGTTTGTGCCTGTCCT | 72 | GGAAGAGAATCCGCAAGA | 143 | GCTTCTTGTCCTGCTTGCTT | 43 |
| APC 102843C > CG:1545S > S/X | TCAGAGCAGCCTAAAGAATGTTTTCCAAGTTGAAAACCAAGAGAAA | 73 | ATGCCTCCAGTTCAGGAAAA | 144 | TTTTTCTGCCTCTTTTCTTGG | 180 |
| tp53 E4 12392G > GT, 135C > C/F | CCTCAACAAGATGTTTTTCCAACTGGCCAAGACCT | 74 | TGCCCTGACTTTCAACTCTGT | 145 | CTGCACAGGGCAGGTCTT | 181 |
| APC 102557C > CT: 1450R > R/X | CTCAAAACAGCTCAAACCAGTGAGAAGTACCTAAAAATAAA | 59 | ACCACCTTCCTCAAACAGCTC | 134 | GCAGCTTGCTTAGTTCCACT | 173 |
| tp53 E7 13819G > T:280R > I | CCTGTCCTGGGATAGACCGGCGAC | 75 | CTACTGGGACGGAACAGCTT | 146 | GCGGAGATTCTCTTCCTCTG | 182 |
| tp53 13E4 113326A > AC (splice site) | TCTTTTCACCCATCTACCCCCTTGCCGTCCC | 69 | ACCTGGTCCTCTGACTGCTC | 140 | GGGGACACAGCATCAAATCATC | 179 |
| tp53 E7 13412G > GT:259D > D/Y | CCATCATCACACTGGAATATCCAGGTCAGGAGCC | 70 | CCTCACCATCATCACACTGG | 41 | GGGTCAGAGGCAAGCAGA | 40 |
| tp53 E5 12449G > GT:154G > G/V | ACCCCCGCCCGTCACCCGCGTCC | 71 | GTGCAGCTGTGGGTTGATT | 142 | CTCCGTCATGTGCTGTGACT | 170 |
| tp53 E8 13872G > GT, 298E > E/X | GGAGCCTCACCACTAGCTGCCCCAGG | 76 | GGAAGAGAATCCGCAAGA | 143 | GCTTCTTGTCCTGCTTGCTT | 43 |
| tp53 E8 13813C > CG:278P > P/R | GTGTTTGCTGTCGTGGGAGAGACCGGCG | 77 | CTACTGGGACGGAACAGCTT | 146 | GCGGAGATTCTCTTCCTCTG | 182 |
| tp53 E8 13851A > AT,291K > K/X | GGAAGAGAATCTCCCCTAGAAAGGGGAGCCTCA | 78 | GCCACACAGAGGAAGAGAATC | 147 | TTCTTGTCCTGCTTGCTTACC | 183 |
| smad4 E2 19049G > GA, 18118A > A/A | GTTAAATATTGTCAGTATGCATTTGACTTAAAATGTGATAG | 79 | AGGTGGGCCTGATCTTCACAA | 148 | TGGATTCACACAGACACTATCACA | 184 |
| tp53 E8 137770 > GA. 266G > G/E | TAGTGGTAATCTACTGGAACGGAACAGCTTTGAGGTG | 80 | TTTTCCTTACTGCCTCTTTGCTTC | 149 | CACAAACACGCACCTCAAAG | 185 |
| tp53 E6 12653T > TC:195I > I/T | CCTCCTCAGCATCTTACCCGAGTGGAAGGAAAT | 81 | CAGGCCTCTGATTCCTCACT | 36 | ACACGCAAATTTCCTTCCAC | 174 |
| tp53 E7 133790 > CT:248R > R/W | GCATGGGCGGCATGAACTGAGGCCCATCCTCACC | 68 | TGGCTCTGACTGTACCACCA | 139 | CCAGTGTGATGATGGTGAGG | 178 |
| tp53 E6 12647A > AG:193H > H/R | TCTGGCCCTCCTCAGCGTCTTATCCGAGTGGAAG | 62 | CAGGCCCTCTGATTCCTCACT | 36 | ACACGCAAATTTCCTTCCAC | 174 |
| tp53 E6 12712A > AG:215S > S/G | GAAACACTTTTCGACATGGTGTGTGGTGCCTGT | 65 | GTGGAAGGAAATTTGCGTGT | 136 | CAGTTGCAAACCAGACCTCA | 76 |
| tp53 E8 13872G > GT:298E > E/X | GGAGCCTCACCACTAGCTGCCCCAGG | 76 | GGAAGAGAATCCGCAAGA | 143 | GCTTCTTGTCCTGCTTGCTT | 43 |

TABLE 7-continued

Sequence Specific Capture Probes and Primers for AD Cancer Mutation Detection

| MUTATION IN TISSUE | CAPTURE PROBE | SEQ ID No. | SENSE PRIMER 1 (5' TO 3') | SEQ ID No. | ANTISENSE PRIMER 2 (5' TO 3') | SEQ ID No. |
|---|---|---|---|---|---|---|
| tp53 e7 13370G > GA:245G > G/S | AGTTCCTGCATGGGCAGCATGAACCGGAGGC | 82 | TGGCTCTGACTGTACCACCA | 139 | CCAGTGTGATGATGGTGAAGG | 178 |
| tp53 e4 11580het_delG | CTGGGCTTCTTGCATTCTGACACAGCCAAGTCTGTGA | 83 | CCCTTCCCAGAAAACCTACC | 30 | ACTGACCCGTGCAAGTCACAG | 186 |
| tp53 E5 12524A > AG, 179H > H/R | TGCCCCCACCGTGAGCGCTGC | 84 | TGCCATCTACAAGCAGTCA | 150 | CTGCTCACCATCGCTATCTG | 187 |
| tp53 E6 12661G > GT,198E > E/X | TCAGCATCTTATCCGAGTGTAAGAAATTTGCGTGTGGA | 85 | CAGGCCTCTGATTCCTCACT | 36 | CCAAATACTCCACACGCAAA | 188 |
| tp53 E8 13872G > GT 298E > E/X | GGAGCCTCACCACTAGCTGCCCCAGG | 76 | GGAAGAGAATCTCCGCAAGA | 143 | GCTTCTTGTCCTGCTTGCTT | 43 |
| apc 102494C > CT: 14290 > Q/X | TCCAGATAGCCCTGATAAACCATGCCACCAAG | 58 | CAGGAGACCCCACTCATGTT | 19 | TGGCAAAATGTAATAAAGTATCAGC | 20 |
| apc 102557C > CT;1450R > R/X | CTCAAACAGTCAAACCAAGTGAGAAGTACTAAAAATAAA | 59 | CAGGAGACCCCACTCATGTT | 19 | TGGCAAAATGTAATAAAGTATCAGC | 20 |
| apc 102140het_delA | AGCAGAAATAAAGAAAGTTGGAACTAGTCAGCTGA | 60 | TTCATTATCATCTTTGTCATCAGC | 15 | CGCTCCTGAAGAAATTCAA | 16 |
| apc 102494C > CT;14290 > Q/X | TCCAGATAGCCCTGATAAACCATGCCACCAAG | 58 | CAGGAGACCCCACTCATGTT | 19 | TGGCAAAATGTAATAAAGTATCAGC | 20 |
| apc 102134G > GT: 1309E > B/X | TGCAAATAGCAGAAATAAAATAAAGATTGGAACTAGG | 86 | TTCATTATCATCTTTGTCATCAGC | 15 | CGCTCCTGAAGAAATTCAA | 16 |
| apc 102554het_delA | CTCAAACAGTCAAACCAGCGAGAAGTACTAAA | 61 | CAGGAGACCCCACTCATGTT | 19 | TGGCAAAATGTAATAAAGTATCAGC | 20 |
| apc 102852bet_insA | CTAAAGAATCAAATGAAAAACCAAGAGAGAAGAGGCAGAA | 87 | GAGGCCTCGATGAGGCCATTTA | 23 | TCAATATCATCATCTGAATCATC | 24 |
| Kras 5571G > GA: 12G > G/D | GTGGTAGTTGGAGCTGATGCGTAGGCAAGAGT | 88 | AGGCCTCTGAAAATGACTG | 2 | TTGTTGGATCATATTCGTCCAC | 3 |
| tp53 E4 12392G > GA; 135C > C/Y | CCTCAACAAGATGTTTTACCAACTGGCCAAGACCT | 89 | TGTTCACTTGTGCCCTGACT | 137 | GCAGGTCTTGGCCAGTTG | 177 |
| tp53 E5 12655C > CT; 196R > R/X | CCTCCTCAGCATCTTATCTGAGTGGAAGGAAATTTGC | 90 | CAGGCCTCTGATTCCTCACT | 36 | ACACGCAAATTTCCTTCCAC | 174 |
| tp53 E6 13350G > GA; 238C > C/Y | TCCACTACAACTACATGTATAACAGTTCCTGCATGGG | 91 | TGGCTCTGACTGTACCACCA | 139 | CCAGTGTGATGATGGTGAAGG | 178 |
| tp53 E6 13420G > GA | CACTGGAAGACTCCAGATCAGGAGCCACTTGCC | 92 | CCTCCACCATCATCACACTGG | 141 | GGGTCAGAGAGGCAAGCAGA | 40 |
| tp53 E5 12712A > AG; 215S>S/G | GAAACACTTTTTGACATGGTGTGGTGCCCTAT | 65 | GTGAAGGAAATTTGCGTGT | 136 | CAGTTGCAAACCAGACCTCA | 176 |
| Kras 5571IG > GA; 12G > G/D | GTGGTAGTTGGAGCTGATGCGTAGGCAAGAGT | 88 | AGGCCTCTGAAAATGACTG | 2 | TTGTTGGATCATATTCGTCCAC | 3 |

TABLE 7-continued

Sequence Specific Capture Probes and Primers for AD Cancer Mutation Detection

| MUTATION IN TISSUE | CAPTURE PROBE | SEQ ID No. | SENSE PRIMER 1 (5' TO 3') | SEQ ID No. | ANTISENSE PRIMER 2 (5' TO 3) | SEQ ID No. |
|---|---|---|---|---|---|---|
| P16 (ink4a) E1 19638A > AT | GGAGAGGGGAGTGCAGGCAGCGGG | 93 | AGCCAGTCAGCCGAAGG | 151 | GAGGGGCTGGCTGGTC | 189 |
| P16 (ink4a) E2 23353G > GT; 447D > DY | CCCAACTGCGCCTACCCCGCCACTC | 94 | CACCCTGGCTCTGACCAT | 152 | GGGTGGGTGAGAGTGG | 190 |
| P16 (ink4a) E1 19638A > AT | GGAGAGGGGAGTGCAGGCAGCGGG | 93 | AGCCAGTCAGCCGAAGG | 151 | GAGGGGCTGGCTGGTC | 189 |
| p16(ink4a) E2 23402het_delT_ | GCCCCGGGAGGGCTCCTGGACACGCTG | 95 | GACCCCGCCACTCTCAC | 153 | CAGTCCTCCAGCCAGGTC | 191 |
| p16(ink4a) E2 23403C > CA; 484F > F/ | GCCCCGGGAGGGCTTACTGGACACGCTGGT | 96 | GACCCCGCCACTCTCAC | 153 | CAGTCCTCCAGCCAGGTC | 191 |
| ctnnb1 2541het_delT | CAATGGGTCTATATCACAGATTCTTTTTTTAAATTAAA GTAACA | 97 | ATATTTCAATGGGTCATATCA CAG | 154 | TCAAATCAGCTATAAATAC GAAACA | 192 |
| cdh 1 E9 7643het_delA | TCTTATCTCAAAAGAACAACAAAAAAAGAGGAATCCTT TAG | 98 | GCCATGATCGCTCAAATACA | 155 | TCTCAGGGGCTAAAGGATT | 193 |
| cdh1 E1 743_744het_insAGCCCTGCGCCCA | GCGCCCAGCCCTGCGCCCATTCCTC | 99 | ACTTGCGAGGACGCATT | 156 | GAAGAAGGGAAGCGGTGAC | 194 |
| cdh 1 E13 868536854het_insA | AAGTAAGTCCAGCTGGCAAAGTCAGCCTTTGACTT | 100 | CATTCTGGGGATTCTTGAAG | 157 | GGAAATAAACCTCCTCCA TTTTT | 195 |
| cdh 1 E14 91472C>CT; 751N>N/N | AGGATGACACCCGGGACAATGTTTATTACTATGATGAAG | 101 | CTGTTTCTTCGGAGGAGAGC | 158 | CCGCCTCCTCTTCTTCATCATA | 196 |
| cdh 1 E 15 92868_92896het delTTGACTTGA GCCAGCTGCACAGGGCCTG | TTTTTTCTCCAAAGGACTGACGCTCGGCCTGAAGTG | 102 | TTCCTACTCTTCATTGTACTT CAACC | 159 | TGCAACGTCGTTACGAGTCA | 197 |
| cdh 1 E4 71669*het_delA | CAAGCAGAATTGCTCACTTTCCCAACTCCTCTCC | 103 | CGTTTCTGGAATCCAAGCAG | 160 | GCAGCTGATGGGGAGGAATAA | 198 |
| cdh 1 E7 74926G > GA; 289A > A/T | GGTCACAGCCACAGAGACACGGACGATGATGATGAA | 104 | CCAGGAACCTCTGTGATGA | 161 | TGAGGATGGTGTAAGCGATG | 199 |
| cdh 1 E1 736_742het_delTGCGCCC | AGCCCTGCGCCCCTTCCTCTCCG | 105 | ACTTGCGAGGACGCATT | 156 | GAAGAAGGGAAGCGGTGAC | 194 |
| p16(ink4a) E1 19638A > AT | GGAGAGGGGAGTGCAGGCAGCGGG | 93 | AGCCAGTCAGCCGAAGG | 151 | CTCACAACCTCCGTCATGTG | 169 |
| tp53 E4 12365A > AG; 126Y > Y/C | TTCCTCTTCCTACAGTGTCTCCCCTGCCTCAAC | 106 | CACTTGTGCCCTGACTTTCA | 33 | GCCAGTTGGCAAAACATCT | 200 |
| tp53 E4 12548G > GA | TGCTCAGATAGCGATGATGAGCAGCTGGGGCTG | 107 | CACATGACGGAGGTTGTGAG | 162 | AACCAGCCCTGTCGTCTCT | 34 |
| p16(ink4a) E1 19810T > TG; 491I > I/S | GGTCGGAGGGCCAGCCAGGTGGGTAGA | 108 | TTCCAATTCCCCTGCAAA | 163 | CCCAACGCACCGAATAGT | 201 |
| tp53 E7 13757G > GA | GCTTCTCTTTTCCTATCCTAAGTAGTAGTGTAATCTACTGG | 109 | GGGACAGGTAGGACCTGATTT | 164 | AGCTGTTCCGTCCCAGTAGA | 202 |

TABLE 7-continued

Sequence Specific Capture Probes and Primers for AD Cancer Mutation Detection

| MUTATION IN TISSUE | CAPTURE PROBE | SEQ ID No. | SENSE PRIMER 1 (5' TO 3') | SEQ ID No. | ANTISENSE PRIMER 2 (5' TO 3) | SEQ ID No. |
|---|---|---|---|---|---|---|
| tp53 E7 13815G > GC; 279G > G/R | TTGTGCCTGTCCTCGGAGAGACCGGCG | 110 | CTACTGGGACGGAACAGCTT | 146 | GCGGAGATTCTCTTCCTCTG | 182 |
| tp53 E7 13816G > GA; 279G > G/E | TGTGCCTGTCCTCGAGAGACCGGCGC | 111 | CTACTGGGACGGAACAGCTT | 146 | GCGGAGATTCTCTTCCTCTG | 182 |
| tp53 E5 12365A > AC, 126Y > Y/S | TTCCTCTTCTACAGTCCTCCCCTGCCCTCAAC | 112 | CACTTGCCCTGACTTTCA | 33 | GCCAGTTGGCAAAACATCT | 200 |
| tp53 E5 12491A > AT, 168H > HL | TCTACAAGCAGTCACAGCTCATGACGGAGGTTGTGGA | 113 | TGGCCATCTACAAGCAGTCA | 150 | CTGCTCACCATCGCTATCTG | 187 |
|  |  | 113 | TGGCCATCTACAAGCAGTCA | 150 | TCACCATCGCTATCTGAGCA | 203 |
|  |  | 113 | TGGCCATCTACAAGCAGTCA | 150 | AACCAGCCCTGTCTGTCTCT | 34 |
| kras 5570G > GC, 12G > G/R | GTGGTAGTTGGAGCTGATGGCGTAGGCAAGAGT | 88 | AGGCCTCTGCTGAAAATGACTG | 2 | TTGTTGGATCATATTCGTCCAC | 3 |
| tp53 E7 13370G > GA, 245G > G/S | AGTTCCTGCATGGGCAGCATGAACCGGAGGC | 82 | TGGCTCTGACTGTACCACCA | 139 | CCAGTGTGATGATGGTGAGG | 178 |
| apc 102864_102865het_delAG | AAATGAAAACCAAGAGAAGGCAGAAAAAACTATTGATTC | 114 | TGACAATGGGAATGAAACAGA | 165 | GGTCCTTTTCAGAATCAATAGTTTT | 204 |
| tp53 E5 12386T > TC, 133M > M/T | CCTGCCCTCAACACGTTTGCCAACTGGCC | 115 | TGTTCACTTGTGCCCTGACT | 137 | GCAGTCTCTGGCCAGTTG | 177 |
| cdh1 E15 93059G > GA | GCTCATCTCTTAAGCTCAGGAAGAGTTGTGTCAAAAATGAGA | 116 | CCAAAAGCATGGCTCATCTCTA | 205 | CTCAGGCAGCAGCTGAAAACAT | 206 |
| tp53 E8 13798G > GA:273R > R/H | CGGAACAGCTTTGAGGTGCATGTTTGTGCCTGTCCTGGG | 117 | CTACTGGGACGGAACAGCTT | 146 | GCGGAGATTCTCTTCCTCTG | 182 |
| p53 E6, 12698_12701het_delAC (1 or 2 AC repeats) | TGGAAGGAAATTTGCGTGTGTGGAGTATTGGATGACAG | 118 | GTGGAAGGAAATTTGCGTGT | 136 | AGCTGTTTGAGGAGGTGGTG | 172 |
| P53 E8, 13824C > CT, 282R > R/W | TGTCCTGGGAGAGACTGGCGCACAGAGGAAGAGAAT | 119 | CTACTGGGACGGAACAGCTT | 146 | GCGGAGATTCTCTTCCTCTG | 182 |
| APC 1021516 > GA, 1314R > R/R | AAGAAAAGATTGGAACTAGATCAGTGAGATCCTGTG | 120 | CAGAGCGACACAGAAGCAGA | 133 | GTGACACTGCTGGAACTTCG | 207 |
| PS3 E5 12457 G > G/T | CGCCCGGCACCCGCTTCCGCGCCATGGCCA | 121 | GTGCAGTGTGGGTTGATT | 142 | CTCCGTCATGTGCTGTGACT | 170 |
| p53 E8138I2C > CG, 278P > P/A | GTGTTTGTGCCTGTGCTGGGAGAGACCGGCG | 122 | CTACTGGGACGGAACAGCTT | 146 | GCGGAGATTCTCTTCCTCTG | 182 |
| APC 102686het_delA | AGGTTCTTCCAGATGCTGATACTTTATTACATTTTGC | 123 | CTGCAGTTCAGAGGGTCCAG | 210 | CACTCAGGCTGATGAACAA | 22 |
| APC het_delAG between 102594_102603 (1 of 5 AG repeats) | GCGAAGTACCTAAAAATAAAGCACCTACTGCTGAA | 124 | AGCTCAAACCAAGCGAGAAG | 131 | AGCATCTGAAGAACCTGGA | 28 |
| APC 102240C > CA, 13445 > S/X | CAGGGTTCTAGTTTATCTTAAGAATCAGCCAGGCACA | 125 | CCCTAGAACCAAATCCAGCA | 166 | TGTCTGAGCACCACTTTTGG | 208 |
| 102676102680delACATT | CCAGATGCTGATACTTTATTTTGCCACGAAAGTACTC | 126 | CTGCAGTTCAGAGGGTCCAG | 167 | CACTTCAGGCTGGATGAACAA | 22 |
| 12487C > CT:167Q > Q/X | ATGGCCATCTACAAGCAGTCAGTCATAGCACATGACGGAGGTTGT | 49 | AGTACTCCCCTGCCCCTCAAC | 128 | CTACAACCTCCGTCATGTG | 169 |

TABLE 7-continued

Sequence Specific Capture Probes and Primers for AD Cancer Mutation Detection

| MUTATION IN TISSUE | CAPTURE PROBE | SEQ ID No. | SENSE PRIMER 1 (5' TO 3') | SEQ ID No. | ANTISENSE PRIMER 2 (5' TO 3') | SEQ ID No. |
|---|---|---|---|---|---|---|
| 102447 102450het delTGGT | AGAGTGAACCATGCAGTGGAAAAGTGGCATTATAAGCCCC | 50 | TTTGAGAGTCGTTCGATTGC | 129 | CATGGTTTGTCCAGGGCTAT | 27 |
| 12410G > CA, 141C > C/Y | TTTGCCAACTGGCCAAGACCTACCCTGTGCAGCTGTG | 51 | AGTACTCCCCTGCCCTCAAC | 128 | CTCCGTCATGTGCTGTGACT | 170 |
| 10267Shet delA | CAGATGCTGATACTTTATTACTTTTGCCACGGAAAGTACT | 52 | TCCAGGTTCTTCCAGATGCT | 130 | CACTCAGGCTGGATGAACAA | 22 |
| 102594 102598het delAGAGA | AAAGCACCTACTGCTGAAAGAGAGTGGACCTAAGCAAG | 127 | AGCTCAAACCAGCAGCGAGAAG | 131 | AGCATCTGAAGAACCTGGA | 28 |
| 102776A > AT:1523R > R/X | ATGACAATGGGAATGAAACAGAATCAGAGCAGCCTAAAG | 14 | TTTGCCACGGAAAGTACTCC | 168 | TTTCCTGAACTGGAGGCATT | 209 |
| 102644 102645het_insG | ATGCTGCAGTTCAGAGGGGTCCAGGTTCTTCCAGATGC | 54 | GGACCTAAGCAAGCTGCAGTA | 132 | CACTCAGGCTGGATGAACAA | 22 |
| 102594 102595het_delAG | TAAAGCACCTACTGCTGAAAAGAGAGAGTGGACCTAAG CAAG | 55 | AGCTCAAACCAGCGAGAAG | 131 | AGCATCTGAAGAACCTGGA | 28 |
| 102106het delT | CACAGGAAGCAGATTCTGCAATACCCTGCAAATAGCA | 56 | CAGACGACACAGGAAGCAGA | 133 | TGCTGGATTTGGTTCTAGGG | 171 |
| 102442het_delT | TTCAGAGTGAACCATGCAGGGAATGGTAAGTGGCATTAT | 57 | TTTGAGAGTCGTTCGATTGC | 129 | CATGGTTTGTCCAGGGCTAT | 27 |
| apc 102494C > CT: 1429Q > Q/X | TCCAGATAGCCCTGATAAACCATGCCACCAAG | 58 | GTGAACCATGCAGTGGAATG | 25 | AGTTGTTGAGGAGGTGGTG | 172 |
| apc 102140het_delA | AGCAGAAATAAAAGAAAAGTTGGAACTAGTCAGTGA | 60 | CAGACGACACAGGAAGCAGA | 133 | TGCTGGATTTGGTTCTAGGG | 171 |
| apc 102554het_delA | CTCAAACAGCTCAAACCAGCGAGAAGTACCTAAA | 61 | CATGCCACCAAGCAGAAGTA | 21 | GCAGCTTGCTTAGTGTCCACT | 173 |

Target mutations were not detected in control stools. Target mutations were detected in stools from 68% (47/69) of patients with a GI neoplasm. Specifically, target mutations were detected in stools from 71% (36/51) of patients with cancer [40% (2/5) with oropharyngeal, 65% (11/17) with esophageal, 100% (4/4) with gastric, 55% (6/11) with pancreatic, 75% (3/4) with biliary or gallbladder, and 100% (10/10) with colorectal] and from 61% (11/18) with precancers [100% (2/2) with pancreatic intraductular papillary mucinous neoplasia and 56% (9/16) with colorectal advanced adenoma]. Mutant copies in genes recovered from stool averaged 0.4% (range 0.05-13.4%) for supracolonic and 1.4% (0.1-15.6%) for colorectal neoplasms, p=0.004 (Table 8).

TABLE 8

Digital Melt Curve Detection of Validated Mutations in AD Cancer Patient Stool

| # | ID | Site | Age | Gender | Tissue Mutation | | | Stool Detection | Mutation Frequency % | Normal Control |
|---|---|---|---|---|---|---|---|---|---|---|
| 1 | 1163 | Head/Neck(pharynx) | 73 | M | tp53 | | | YES | 0.8 | Neg |
| 2 | 1250 | Head/Neck(pharynx) | 49 | M | tp53 | | | NO | | Neg |
| 3 | 1295 | Head/Neck(pharynx) | 47 | F | tp53 | | | NO | | Neg |
| 4 | 1391 | Head/Neck | 65 | M | tp53 | TP53 | | NO (both) | | Neg |
| 5 | 1427 | Head/Neck | 60 | M | tp53 | tp53 | | YES(p53-1), No (p53-2) | 0.05 | Neg |
| 1 | 745 | Esophagus | 84 | F | tp53 | | | YES | 0.4 | Neg |
| 2 | 769 | Esophagus | 56 | F | tp53 | | | YES | 0.4 | Neg |
| 3 | 782 | Esophagus | 55 | M | tp53 | | | NO | | Neg |
| 4 | 789 | Esophagus | 61 | M | tp53 | | | YES | 1.6 | Neg |
| 5 | 819 | Esophagus | 53 | M | tp53 | | | YES | 0.2 | Neg |
| 6 | 873 | Esophagus | 61 | M | tp53 | | | YES | 0.2 | Neg |
| 7 | 906 | Esophagus | 55 | M | APC | | | YES | 0.8 | Neg |
| 8 | 1049 | Esophagus | 57 | M | tp53 | | | NO | | Neg |
| 9 | 1064 | Esophagus | 72 | F | tp53 | | | NO | | Neg |
| 10 | 1067 | Esophagus | 72 | M | tp53 | | | YES | 0.7 | Neg |
| 11 | 1103 | Esophagus | 78 | M | tp53 | | | NO | | Neg |
| 12 | 1199 | Esophagus | 66 | M | tp53 | | | YES | 0.5 | NEG |
| 13 | 1307 | Esophagus | 51 | M | tp53 | | | NO | | NEG |
| 14 | 1373 | Esophagus | 76 | M | tp53 | | | YES | 0.5 | NEG |
| 15 | 1414 | Esophagus | 66 | M | tp53 | | | YES | 0.1 | NEG |
| 16 | 1448 | Esophagus | 82 | M | tp53 | | | NO | | NEG |
| 17 | 1072 | Esophagus | | | tp53 | | | YES | 0.4 | NEG |
| 1 | 798 | Stomach | 81 | M | cdh1 | | | YES | 13.2 | NEG |
| 3 | 1221 | Stomach | 55 | M | cdh1 | cdh1 | | YES(both) | 8, 1.3 | NEG |
| 4 | 1224 | Stomach | 75 | F | smad4 | cdh1 | | YES(smad4), No(CDH1) | 0.2 | |
| 5 | 1402 | Stomach | 56 | M | APC | tp53 | | YES (p53) | 0.1 | NEG |
| 1 | 848 | Gall Bladder | 67 | M | tp53 | | | YES | 0.1 | NEG |
| 2 | 1315 | Gall Bladder | 57 | F | tp53 | | | YES | 1.4 | NEG |
| 1 | 1043 | Bile Duct | 51 | F | APC | | | NO | | NEG |
| 2 | 1554 | Bile Duct | 77 | M | cdh1 | | | YES | 13.4 | NEG |
| 1 | 757 | Pancreatic Cancer in situ | 78 | M | K-ras | | | YES | 0.2 | NEG |
| 2 | 1349 | Pancreatic Cancer in situ | 64 | M | K-ras | | | YES | 0.2 | NEG |
| 1 | 839 | Pancreas | 69 | F | tp53 | | | YES | 0.2 | NEG |
| 2 | 1204 | Pancreas | 65 | F | | p16 | | NO | | NEG |
| 3 | 1253 | Pancreas | 63 | F | K-ras | | tp53 | Yes(k-ras), No(p53) | 2 | NEG |
| 4 | 1400 | Pancreas | 71 | F | tp53 | K-ras | | No(both) | | NEG |
| 5 | 1547 | Pancreas | 77 | F | tp53 | | | NO | | NEG |
| 6 | 1217 | Pancreas | | | K-ras | | | NO | | NEG |
| 7 | 1073 | Pancreas | | | K-ras | | | NO | | NEG |
| 8 | 532 | Pancreas | | | K-ras | | | YES | 1 | NEG |
| 9 | 1592 | Pancreas | | | K-ras | P53 | | YES (both) | 0.3 | NEG |
| 10 | 1695 | Pancreas | | | K-ras | | | YES | 0.2 | NEG |
| 11 | 1058 | Pancreas | | | K-ras | P53 | APC | YES(K-ras) | 0.2 | NEG |
| 1 | 438 | Colorectal Cancer | 78 | F | | APC | | YES | 1.2 | NEG |
| 2 | 446 | Colorectal Cancer | 74 | M | BRAF | | | YES | 0.4 | NEG |
| 3 | 529 | Colorectal Cancer | 46 | M | K-RAS | | | YES | 1 | NEG |
| 4 | 489 | Colorectal Cancer | 73 | M | K-RAS | | | YES | 2.6 | NEG |
| 5 | 549 | Colorectal Cancer | 79 | M | BRAF | | | YES | 1.6 | NEG |
| 6 | 551 | Colorectal Cancer | 69 | M | K-RAS | | | YES | 5.8 | NEG |
| 7 | 584 | Colorectal Cancer | 68 | M | K-RAS | | | YES | 1.4 | NEG |
| 8 | 894 | Colorectal Cancer | 57 | M | P53 | APC | | YES(p53, APC) | 1.6, 5 | NEG |

TABLE 8-continued

Digital Melt Curve Detection of Validated Mutations in AD Cancer Patient Stool

| # | ID | Site | Age | Gender | Tissue Mutation | | Stool Detection | Mutation Frequency % | Normal Control |
|---|------|---------------------|-----|--------|------|-------|--------------------|------|-----|
| 9 | 998 | Colorectal Cancer | 45 | F | APC | KRAS | YES(K-ras, APC) | 0.6, 0.8 | NEG |
| 10 | 1009 | Colorectal Adenoma | 65 | F | P53 | | YES | 12.9 | NEG |
| 1 | 513 | Colorectal Adenoma | 65 | F | APC | | YES | 0.1 | NEG |
| 2 | 546 | Colorectal Adenoma | 61 | M | APC | | NO | | NEG |
| 3 | 547 | Colorectal Adenoma | 52 | F | APC | | NO | | NEG |
| 4 | 568 | Colorectal Adenoma | 52 | M | APC | | YES | 7.8 | NEG |
| 5 | 578 | Colorectal Adenoma | 71 | F | APC | | NO | | NEG |
| 6 | 590 | Colorectal Adenoma | 54 | F | APC | | YES | 3.2 | NEG |
| 7 | 701 | Colorectal Adenoma | 72 | F | APC | | NO | | NEG |
| 8 | 855 | Colorectal Adenoma | 75 | M | K-RAS | | YES | 0.4 | NEG |
| 9 | 860 | Colorectal Adenoma | 53 | M | APC | | YES | 15.6 | NEG |
| 10 | 900 | Colorectal Adenoma | 64 | F | APC | K-RAS | No(both) | | NEG |
| 11 | 962 | Colorectal Adenoma | 56 | M | K-RAS | | Yes | 1 | NEG |
| 12 | 965 | Colorectal Adenoma | 82 | M | APC | K-RAS | No (both) | | NEG |
| 13 | 991 | Colorectal Adenoma | 79 | M | APC | K-RAS | YES(K-ras), No(APC) | 0.2 | NEG |
| 14 | 1135 | Colorectal Adenoma | 59 | M | K-RAS | | YES | 13 | NEG |
| 15 | 1231 | Colorectal Adenoma | 50 | M | APC | | NO | | NEG |
| 16 | 1559 | Colorectal Adenoma | | | K-RAS | | YES | 1 | NEG |

We also performed an initial pilot study with 10 stool samples from patients with confirmed bile duct cancers to determine if DMC technology could detect mutations in k-ras, a well characterized gene known be mutated in this population. K-ras mutations were detected in stools for 3/10 or 4/10 bile duct cancers (depending on mutation score of 5 or 3, respectively) (Table 9). As K-ras is mutant in 30-40% of bile duct cancers, these results indicate that the detection assay is picking up the appropriate proportion of cancer samples.

TABLE 9

K-ras mutation scores for patients with bile duct cancer.

| Sample # | Pathology | K-ras Mutation Score | Mutation Detected A | B |
|---|---|---|---|---|
| 520 | BD Cancer | 0 | | |
| 528 | BD Cancer | 0 | | |
| 559 | BD Cancer | 0 | | |
| 558 | BD Cancer | 1 | Codon 12 GAT | |
| 515 | BD Cancer | 2 | Codon 12 GAT | |
| 543 | BD Cancer | 2 | Codon 13 GAC | |
| 806 | BD Cancer | 3 | Codon 12 TGT | |
| 539 | BD Cancer | 5 | Codon 12 GAT | Codon 13 GGA |
| 512 | BD Cancer | 6 | Codon 12 GAT | Codon 12 GAT |
| 725 | BD Cancer | 25 | Codon 13 GAC | Codon 12 GAT; Codon 12 GTT |

Allele Specific PCR

The allele specific-PCR assay was a modified version of a previously published method (e.g., Cha et al., Mismatch Amplification Mutation Assay (MAMA): Application to the c-H-ras Gene PCR Methods and Applications, 2:14-20 (1992) Cold Spring Harbor Laboratory). TP53 gene fragments were captured from stool DNA samples with probes specific to mutations identified in the matched tissue (Table 7). Copy numbers were assessed by qPCR. Samples were adjusted to 10,000 fragments each and amplified with allele specific primer sets.

| Sample | F Primer | R Primer |
|---|---|---|
| A745 | GACAGAAACACTTTAT (SEQ ID No: 211) | CGGCTCATAGGG (SEQ ID NO: 217) |
| A848 | ACACTTTTCGACAAG (SEQ ID No: 212) | AAACCAGACCTCAG (SEQ ID No: 218) |
| A789 | CCTCAACAAGATAC (SEQ ID No: 213) | CAGCTGCACAGG (SEQ ID) NO: 219) |
| A782 | GCCGCCTGAAA (SEQ ID No: 214) | AGACCOCAGITGC (SEQ ID No: 220) |
| A873 | GCGGCATGAAAT (SEQ ID No: 215) | TTCCAGTGTGATGAT (SEQ ID NO: 221) |
| A769 | CCCCICCTCAGAG (SEQ ID No: 216) | CITCCACTCGGATAA (SEQ ID No: 222) |

The forward primer in each case is specific for each TP53 mutation.

Esophagus and Stomach

Targeting mutations found in esophageal cancers or those from gastroesophageal junction (on p53, APC, or K-ras), the same mutation was detected by allele-specific PCR in matched stools from five of five (100%) cancers but in none of the controls (Table 10). The threshold cycle (Ct), designates the PCR cycle at which the product enters the exponential phase of amplification.

Gallbladder

Targeting a mutation confirmed in a gallbladder cancer, the same mutation was found in the matched stool from that patient using allele-specific PCR (Table 10).

TABLE 10

Quantitative Mutant Allele Specific-PCR Results for Matched Aero-digestive Cancers

| Sample | Gene | # fragments | Ct |
|---|---|---|---|
| A769 | esophageal/gastric cancer | p53 | 10K | 71 |
| N | normal | p53 | 10K | >80 |
| A782 | esophageal/gastric cancer | p53 | 10K | 38.8 |
| N | normal | p53 | 10K | 44.1 |
| A745 | esophageal/gastric cancer | p53 | 30K | 42.5 |
| N | normal | p53 | 30K | 45.6 |
| A873 | esophageal/gastric cancer | p53 | 30K | 37.8 |
| N | normal | p53 | 30K | 40.4 |
| A848 | gall bladder cancer | p53 | 10K | 22.4 |
| N | normal | p53 | 10K | 36.3 |
| A789 | esophageal/gastric cancer | p53 | 10K | 25.9 |
| N | normal | p53 | 10K | 28.7 |

Example 9

Candidate Stool Polypeptide Markers Identified for Colorectal Cancer and Precancerous Adenomas The following list of polypeptides were identified by a statistical analysis model using all data generated from mass spectral of fecal protein extracts: β2-macroglobulin, compliment C3 protein, serotransferrin, haptoglobin, carbonic anhydrase 1, xaa-pro dipeptidase, leukocyte elastase inhibitor, hemoglobin, glucose-6-phosphate, and catalase. This list of polypeptides is in order of difference from normal. Thus, the mean spectral abundance for β2-macroglobulin is most different from normal for cancer and adenoma.

The statistical significance of relative polypeptide abundance between normal, adenoma, and colorectal cancer (CRC) was obtained using normalized spectral count data from a zero inflated poisson regression model as an offset term in the protein specific differential expression analysis. The differential expression analysis also incorporated the zero inflated poisson regression model. Polypeptides were then ranked according to their statistical significance and whether the expression profile followed the clinically relevant pattern of Normal<Adenoma<CRC. Using a rule that a positive test required that any three of top six markers be positive, the sensitivity and specificity of this panel were both 100% in a training set.

The listed polypeptides can be used individually or in any combination to detect colorectal cancer or precancerous adenomas.

Example 10

Identification of Polypeptide Markers for Pancreatic Cancer

Potential polypeptide markers for pancreatic cancer prediction were identified. Utilizing a Scaffold (Proteome Software) side-by-side comparison of spectral abundances, ratios of the spectral counts of carboxypeptidase B (CBPB1_HUMAN) and Carboxypeptidase A1 (CBPA1_HUMAN) were compared. A value for carboxypeptidase B/A1 of 0.7 or higher was predictive of pancreatic cancer (in normal stools, an average ratio of 2:3 B/A1 was observed). Specificity for training data was 100% with a sensitivity of 88%, while sensitivity from a validation set was 82% at the same specificity.

Example 11

Use of Fecal Methylated ALX4 as a Neoplasia Marker

Stools from patients with colorectal tumors were found to contain significantly elevated amounts of methylated ALX4 gene copies, but those from normal individuals were found to contain none or only trace amounts. When fecal methylated ALX4 was assayed with an appropriate amplification method, colorectal cancers and premalignant adenomas were specifically detected. At 90% specificity, fecal methylated ALX4 detected 59% colorectal cancer and 54% premalignant adenomas, allowing for the detection of both colorectal cancer and premalignant adenomas.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method comprising:
   (a) obtaining a stool sample from a subject that has or is suspected of having colorectal cancer;
   (b) extracting genomic DNA from the stool sample; and
   (c) using the extracted genomic DNA from the stool sample to determine a K-ras mutation score and BMP methylation status.

2. The method of claim 1, wherein the K-ras mutation score is determined using digital melt curve analysis.

3. The method of claim 1, wherein the K-ras mutation score is determined using quantitative allele-specific PCR.

4. The method of claim 1, wherein the K-ras mutation score is determined by amplifying a region of the extracted genomic DNA using primers specific for one or more K-ras mutations.

5. The method of claim 4, wherein the primers specific for one or more K-ras mutations are selected from SEQ ID NOs: 2, 3, 4, 5, 6, 7, and 8.

6. The method of claim 4, wherein the primers detect a K-ras mutation corresponding to amino acid number 12.

7. The method of claim 1, wherein the BMP methylation status is determined by measuring a methylation level of one or more CpG sites in BMP3.

8. The method of claim 7, wherein measuring a methylation level of one or more CpG sites in BMP3 comprises using one or more of methylation-specific PCR, quantitative methylation-specific PCR, methylation-sensitive DNA restriction enzyme analysis, quantitative bisulfite pyrosequencing, and bisulfite genomic sequencing PCR.

9. The method of claim 1, wherein the BMP methylation status is determined by treating the extracted genomic DNA with a bisulfite reagent.

10. The method of claim 9, wherein the bisulfite reagent is sodium bisulfite.

11. The method of claim 9, wherein the BMP methylation status is determined by amplifying a region of the extracted bisulfite-treated genomic DNA using primers specific for one or more CpG sites in BMP3.

12. The method of claim 1, wherein extracting the genomic DNA from the stool sample comprises using a DNA stabilization buffer.

13. The method of claim 1, wherein extracting the genomic DNA from the stool sample comprises using DNA extraction reagents.

* * * * *